US008460669B2

(12) United States Patent
Hsieh et al.

(10) Patent No.: US 8,460,669 B2
(45) Date of Patent: *Jun. 11, 2013

(54) COMPOSITIONS AND METHODS FOR IDENTIFYING RESPONSE TARGETS AND TREATING FLAVIVIRUS INFECTION RESPONSES

(75) Inventors: Shie-Liang Hsieh, Taipei (TW); Chi-Huey Wong, Rancho Santa Fe, CA (US); Tsui-Ling Hsu, Taipei (TW); Szu-Ting Chen, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/106,046

(22) Filed: May 12, 2011

(65) Prior Publication Data
US 2012/0213770 A1    Aug. 23, 2012

Related U.S. Application Data

(60) Division of application No. 12/079,576, filed on Mar. 27, 2008, now Pat. No. 7,943,134, which is a continuation-in-part of application No. 11/469,270, filed on Aug. 31, 2006, now abandoned.

(60) Provisional application No. 60/713,463, filed on Aug. 31, 2005.

(51) Int. Cl.
*A61K 39/395* (2006.01)
*A61K 39/285* (2006.01)

(52) U.S. Cl.
USPC ............... 424/143.1; 424/130.1; 424/141.1; 424/184.1; 424/218.1; 424/278.1; 435/235.1; 530/387.1; 530/388.1; 530/388.15; 530/388.22

(58) Field of Classification Search
None
See application file for complete search history.

(56) References Cited

U.S. PATENT DOCUMENTS

| | | | |
|---|---|---|---|
| 4,186,183 A | 1/1980 | Steck et al. |
| 4,217,344 A | 8/1980 | Vanlenberghe et al. |
| 4,235,871 A | 11/1980 | Papahadjopoulos et al. |
| 4,261,975 A | 4/1981 | Fullerton et al. |
| 4,485,054 A | 11/1984 | Mezei et al. |
| 4,501,728 A | 2/1985 | Geho et al. |
| 4,774,085 A | 9/1988 | Fidler |
| 4,837,028 A | 6/1989 | Allen |
| 4,946,787 A | 8/1990 | Eppstein et al. |
| 5,010,175 A | 4/1991 | Rutter et al. |
| 5,270,163 A | 12/1993 | Gold et al. |
| 5,288,514 A | 2/1994 | Ellman |
| 5,328,470 A | 7/1994 | Nabel et al. |
| 5,506,337 A | 4/1996 | Summerton et al. |
| 5,519,134 A | 5/1996 | Acevedo et al. |
| 5,525,735 A | 6/1996 | Gallop et al. |
| 5,539,083 A | 7/1996 | Cook et al. |
| 5,549,974 A | 8/1996 | Holmes |
| 5,569,588 A | 10/1996 | Ashby et al. |
| 5,593,853 A | 1/1997 | Chen et al. |
| 5,811,097 A | 9/1998 | Allison et al. |
| 6,416,973 B1 | 7/2002 | Bakker |
| 7,022,828 B2 | 4/2006 | McSwiggen |
| 7,319,140 B2 | 1/2008 | Bakker et al. |
| 7,332,574 B2 | 2/2008 | Bakker et al. |
| 7,998,482 B2 * | 8/2011 | Wong et al. ................ 424/143.1 |
| 2004/0126372 A1 | 7/2004 | Banerjee et al. |
| 2006/0099144 A1 | 5/2006 | McClanahan |
| 2006/0134100 A1 | 6/2006 | Amara |
| 2007/0072247 A1 | 3/2007 | Wong |

FOREIGN PATENT DOCUMENTS

| | | |
|---|---|---|
| WO | WO91/06309 | 5/1991 |
| WO | WO91/19735 | 12/1991 |
| WO | WO92/00091 | 1/1992 |
| WO | WO93/20242 | 10/1993 |
| WO | WO96/10390 | 4/1996 |
| WO | WO96/10391 | 4/1996 |
| WO | WO96/10392 | 4/1996 |
| WO | WO96/40281 A1 | 12/1996 |
| WO | WO96/40281 A2 | 12/1996 |
| WO | WO96/40281 A3 | 12/1996 |
| WO | WO97/00271 | 1/1997 |
| WO | WO02/096945 | 12/2002 |
| WO | WO03/007971 | 1/2003 |
| WO | WO2007/088051 | 8/2007 |

OTHER PUBLICATIONS

Chen et al., CLEC5A Regulates Japanese Encephalitis Virus-Induced Neuroinflammation and Lethality, 2012, PLoS Pathogens, vol. 8, No. 4, pp. 1-18.*
Nature, vol. 453, No. 7195, Epub May 21, 2008, Chen Szu-Ting, et al., "CLEC5A is critical for dengue-virus-induced legal disease".
The Journal of Infectious Diseases, vol. 197, No. 6, Mar. 2008, M. Mezger et al., "Proinflammatory response of immature human dendritic cells is mediated by dectin-1 after exposure to *Aspergillus fumigates* germ tubes".

(Continued)

*Primary Examiner* — Benjamin P Blumel
(74) *Attorney, Agent, or Firm* — Occhiuti Rohlicek & Tsao LLP

(57) ABSTRACT

Cellular receptors are identified that induce plasma leakage and other negative effects when infected with flaviviruses, such as dengue virus or Japanese encephamyelitis virus. Using fusion proteins disclosed herein, the receptors to which a pathogen, such as flavivirus, binds via glycan binding are determined. Once the receptors are determined, the effect of binding to a particular receptor may be determined, wherein targeting of the receptors causing a particular symptom may be targ

OTHER PUBLICATIONS

Autoimmunity Reviews, vol. 6, No. 5, Apr. 2007, M. Ejrnaes, et al., "Cure of chronic viral infection by neutralizing antibody treatment."
Aderam, Alan et al, "Toll-like receptors in the inducstion of the innate immune response," 406 Nature-Insight Review Articles, 782-787 (2000).
Ahmad, Imran and Allen, Theresa M., "Antibody-mediated Specific Binding and Cytotoxicity of Liposome-entrapped Doxorubicin to Lung Cancer Cells in Vitro," Cancer Research, vol. 52, Sep. 1, 1992, pp. 4817-4820.
Akira et al, Toll-like Receptor Signalling, Nature Reviews, Immunology, 2004, vol. 4, pp. 499-511.
Aldrian-Herrada et al, "A peptide nucleic acid (PNA) is more rapidly internalized in cultured neurons when coupled to a retro-inverso delivery peptice. The antisense activity depresses the target mRNA and protein in magnocellular oxytocin neurons," Nucleic Acids Research, 1998, vol. 26, No. 21, pp. 4910-4916.
Arrighi, J.F., et al., "Lentivirus-Mediated RNA Interference of DC-SIGN Expression Inhibits Human Immunodeficiency Virus Transmission from Dendritic Cells to T Cells," Journal of Virology, Oct. 2004, vol. 78, pp. 10848-10855.
Athman et al, "Innate immunity via Toll-like receptors and Nod proteins," Current Opinion on Microbiology, 1996, pgs/units. 9.10-9.14.
Bakker, Alexander B.H., et al, "Meyloid DAP12-associating lectin 9MDL)-1 is a cell surface receptor involved in the activation of myeloid cells," Immunology, 1999, vol. 96, pp. 9792-9796.
Bao, Xing-Feng, et al, "Structural features of immunologically active polysaccharides from Gandoderma lucidum," Phytochemistry 59, (2002), p. 175-181.
Balon, Thomas W. et al., "A Fermentation Products of Cordyceps sinensis Increases Whole-Body Insulin Sensitivity in Rats," The Journal of Alternative and Complementary Medicine, 2002, vol. 8—No. 3, pp. 315-323.
Bartunek, Petr et al, "Avian Stem Cell Factor (SCF): Production and Characterization of the Recombinant HIS-Tagged SCF of Chicken and Its Neutralizing Antibody," Cytokine, Jan. 1996, vol. 8—No. 1, pp. 14-20.
Baum, Rudy M., "Fullerenes Broaden Scientists' View of Molecular Structure," Chemical and Engineering News, Jan. 4, 1993, pp. 29-34.
Behr, Jean-Paul, "Gene Transfer with Synthetic Catonic Amphiphiles: Prospects for Gene Therapy," Bioconjugate Chemistry, 1994, vol. 5, pp. 382-389.
Berkner, Kathleen, "Development of adenovirus vectors for the expression of heterologous genes," BioTechniques, 1988, vol. 6—No. 7, pp. 616-629.
Blaese, M. et al, "Vectors in cancer therapy: how will they deliver?" Cancer Gene Therapy, 1995, vol. 2—No. 4, pp. 291-297.
Boado, Ruben J. et al, "Drug Delivery of Antisense Molecules to the Brain for Treatment of Alzheimer's Disease and Cerebral AIDS," Journal of Pharmaceutical Sciences, Nov. 11, 1998, vol. 87, pp. 1308-1315.
Bouchon, et al., "Cutting Edge: Inflammatory Responses Can Be Triggered by TREM-1, a Novel Receptor Expressed on Neutrophils and Monocytes," Journal of Immunology, 2000, vol. 164, pp. 4991-4995.
Brown and Gordon, "A bird's-eye view of the health of coral reefs," Nature, vol. 413, Sep. 6, 2001, pp. 36-37.
Brown, Gordon D., et al, "Dectin-1 Mediates the Biological Effects of β-Glucans," J. Exp. Med, vol. 197, 2003, pp. 1119-1124.
Brummelkamp, Thijn R., et al, "A system for Stable Expression of Short Interfering RNAs in Mammalian Cells," Science, vol. 296, Issue: 5567, pp. 550-553.
Buenz, E.J., et al., "The traditional Chinese medicine Cordyceps sinensis and its effects on apoptotic homeostasis," Journal of Ethnopharmacology, 2005, vol. 96, pp. 19-29.
Carr, Jillian M., et al, "Supernatants From Dengue Virus Type-w Infected Macrophages Induce Permeability changes in Endothelial Cell Monolayers," Journal of Medical Virology, 69, (2003), pp. 521-528.
Cambi, Alessandra, et al, "Dual function of C-type lectin-like receptors in the immune system," Current Opinion in Cell Biology, vol. 15, 2003, pp. 539-546.
Campbell, David A., "Phosphonate Ester Synthesis Using a Modified Mitsunobu Condensation," Journal of Organic Chemistry, vol. 59, 1994, pp. 658-660.
Carlson Noel G., et al, "Identification of Amino Acids in the Glutamate Receptor, GluR3, Important for Antibody-binding and Receptor-specific Activation," The Journal of Biological Chemistry, vol. 272, No. 17, Apr. 25, 1997, pp. 11295-11301.
Chien, Chichen M., et al, "Polysaccharides of Ganoderma lucidum alter cell immunophenotypic expression and enhance CD56+ NK-cell cytotoxicity in cord blood," Bioorganic & Medicinal Chemistry, 12, (2004), pp. 5603-5609.
Cho, Charles Y., et al, "An Unnatural Biopolymer," Science, 261, (1993), pp. 1303-1305.
Cook, Donald N., et al. "Toll-like receptors in the pathogenesis of human disease," Nature Immunology, 5 (2004), pp. 975-979.
Crystal, Ronald G., "Transfer of Genes to Humans: Early Lessons and Obstacles to Success," Science, 270, (1995), pp. 404-410.
Chang, Yung-Chi, et al, "Modulation of macrophage differentiation and activation by decoy receptor 3," Journal of Leukocyte Biology, 75, (2004), pp. 486-494.
Chen, Hung-Sen, et al, "Studies on the immuno-modulating and anti-tumor activities of Ganoderma lucidum (Reishi) polysaccharides," Bioorganic & Medicinal Chemistry, 12, (2004), pp. 5595-5601.
Chen, Yun-Chi, et al, "Activation of Terminally Differentiated Human Monocytes/Macrophages by Dengue Virus: Productive Infection, Hierarchical Production of Innate Cytokines and Chemokines, and the Synergistic Effect of Lipopolysaccharide," Journal of Virology, 76-19, (2002), pp. 9877-9887.
Chen, Zhong, et al, "Effects of Interleukin-1a, Interleukin-1 Receptor Antagonist, and Neutralizing Antibody on Proinflammatory Cytokine expression by Human Squamous Cell Carcinoma Lines" Cancer Research, 58, (1998), pp. 3668-3676.
Chen, Chixu, et al, "'Analogous' Organic Synthesis of Small-Compound Libraries: Validation of Combinatorial Chemistry in Small-Molecule Synthesis," Journal of the American Chemical Society, 116, (1994) pp. 2661-2662.
Chen, Shu-Hsia, et al, "Gene therapy for brain tumors: Regression of experimental gliomas by adenovirus-mediated gene transfer in vivo," Medical Sciences, 91, (1994) pp. 3054-3057.
Daws, Michael R., et al, "Pattern Recognition by TREM-2: Binding of Anionic Ligans," The Journal of Immunology, 171, (2003), pp. 594-599.
Deng, Bijia, et al, "An Agonist Monoclonal Antibody to the Human c-Mpl Receptor Stimulates Megakaryocytopoiesis," Blood, 92, (1998), pp. 1981-1988.
Durbin, Joan E., et al, "Targeted Disruption of the Mouse Stat1 Gene Results in Compromised Innate Immunity to Viral Disease," Cell, 84, (1996), pp. 443-450.
Emerich, Dwaine F., et al, "Biocompatibility of Poly (DL-Lactide-co-Glycolide) Microspheres Implanted Into the Brain," Cell Transplantation, 8, (1999), pp. 47-58.
Fadden, Andrew J., et al, "Molecular characterization of the rat Kupffer cell glycoprotein receptor," Glycobiology, 13, (2003) pp. 529-537.
Furka, Arpad, et al, "General method for rapid synthesis of multicomponent peptide mixtures," Int J Peptide Res, 37, (1991), pp. 487-493.
Gao, X, et al, "Cationic liposome-mediated gene transfer," Gene Therapy, 2, (1995), pp. 710-722.
Goncalvez, Ana P., et al, "Monoclonal antibody-mediated enhancement of dengue virus infection in vitro and in vivo and strategies for prevention," PNAS, vol. 104, No. 22, May 29, 2007, pp. 9422-9427.
Green, Sharone, et al, "Immunopathological mechanisms in dengue and dengue hemorrhagic fever," Current Opinion in Infectious Diseases, 19, (2006), pp. 429-436.
Guo, Yuan, et al, "Structural basis for distinct ligand-binding and targeting properties of the receptors DC-SIGN and DC-SIGNR," Nature Structural & Molecular Biology, 11-7, (2004), pp. 591-598.

Hagihara, Masahiko, et al, "Vinylogous Polypeptides: An Alternative Peptide Backbone," Journal of American Chemical Society, 114, (1992), pp. 6568-6570.

Haj-Ahmad, Yousef, et al, "Development of a Helper-Independent Human Adenovirus Vector and Its Use in the Transfer of the Herpes Simplex Virus Thymidine Kinase Gene," Journal of Virology, 57, (1986), pp. 267-274.

Halstead, S.B., et al, "Dengue Viruses and Mononuclear Phagocytes," The Journal of Experimental Medicine, 146, (1977), pp. 201-217.

Hammerling, et al., "Monoclonal and T-Cell Hybridomas," (1981), pp. 563-587.

Harrop, Jeremy, et al. "Antibodies to TR2 (Herpesvirus Entry Mediator), a New Member of the TNF Receptor Superfamily, Block T Cell Proliferation, Expression of Activation Markers, and Production of Cytokines," The Journal of Immunology, 161, (1998), pp. 1786-1794.

He, Xianguo, "Chemical Analysis as a Quality Control Method for Medicinal Mushroom and Fungi Extracts," International Journal of Medicinal Mushrooms, 6, (2004), pp. 253-261.

Herre, Jurgen, et al, "Dectin-1 and its role in the recognition of β-glucans by macrophages," Molecular Immunology, 40, (2004), pp. 869-876.

Hirschmann, Ralph, et al, "Nonpeptidal Peptidomimetics with a β-Glucose Scaffolding. A Partial Somatostatin Agonist Bearing a Close Structural Relationship to a Potent, Selective Substance P Antagonist," Journal of American Chemical Society, 114, (1992), pp. 9217-9218.

Dewitt, Sheila Dewitt, et al, "'Diversomers': An approach to nonpeptide, nonoligomeric chemical diversity," Chemistry 90, (1993), pp. 6909-6913.

Hoyle, Gary, et al., "Molecular Cloning and Sequencing of a cDNA for a Carbohydrate Binding Receptor Unique to Rat Kupffer Cells," The Journal of Biological Chemistry, 263, (1988), pp. 7487-7492.

Houghten, Richard, et al., "Generation and use of synthetic peptide combinatorial libraries for basic research and drug discovery," Nature, 354, (1991), pp. 84-88.

Hsu, Hsien-Yeh, et al., "Extract of Reishi Polysaccharides Induces Cytokine Expression via TLR4-Modulated Protein Kinase Signaling Pathways," The Journal of Immunology, 173, (2004), pp. 5989-5999.

Hsu, Tsui-Ling, et al, "Modulation of Dendritic Cell Differentiation and Maturation by Decoy Receptor 3," The Journal of Immunology, 168, (2002), pp. 4846-4853.

Huang, Kao-Jean, et al, "The Dual-Specific Binding of Dengue Virus and Target Cells for the Antibody-Dependent Enhancement of Dengue Virus Infection," The Journal of Immunology, 176, (2006), pp. 2825-2832.

Ishiwata, Hideki, et al., "Physical-Chemistry Characteristics and Biodistribution of Poly(ethylene glycol)-Coated Liposomes Using Poly(oxyethylene) Cholesteryl Ether," Chemical Pharmaceutical Bulletin, 43, (1995), pp. 1005-1011.

Janeway Jr., C.A., "Approaching the Asymptote? Evolution and Revolution in Immunology," Cold Spring Harbor Symposia on Quantitative Biology vol. 54, (1989), pp. 1-13.

Jolliet-Riant, Pascale, et al., "Drug transfer across the blood-brain barrier and improvement of brain delivery," Fundamental Clinical Pharmacology, 13, (1999), pp. 16-26.

Klesney-Tait et al., "The TREM receptor family and signal integration," Nature Immunology, vol. 7 No. 12, Dec. 2006, pp. 1266-1273.

Kuan, Yu-Hsiang, "Artocarpol A stimulation of superoxide anion generation in neutrophils involved the activation of PLC, PKC and p38 mitogen-activated PK signaling pathways," British Journal of Pharmacology, 145, (2005), pp. 460-468.

Liang, Rui, et al, "Parallel Synthesis and Screening of a Solid Phase Carbohydrate Library," Science, 274, (1996), pp. 1520-1522.

Liautard, Janny, et al., "Specific Inhibition of IL-6 Signaling with Monoclonal Antibodies against the gp130 Receptor," Cytokine, 9, (1997), pp. 233-241.

Lien, Eric, "Fungal metabolites and Chinese herbal medicine as immunostimulants," Progress in Drug Research, 34, (1990), pp. 395-420.

Lin, Yi-Ling, et al., "Study of Dengue Virus Infection in SCID Mice Engrafted with Human K562 Cells," Journal of Virology, 72, (1998) pp. 9729-9737.

Liu, Yong, et al, "Cationic Liposome-mediated Intravenous Gene Delivery," The Journal of Biological Chemistry, 270, (1995), pp. 24864-24870.

Liu, Chao, et al., "Peptidoglycan Recognition Proteins," The Journal of Biological Chemistry, 276, (2001), pp. 34686-34694.

Lozach, Pierre-Yves, et al., "Dendritic Cell-specific Intercellular Adhesion Molecule 3-grabbing Non-integrin (DC-SIGN)-mediated Enhancement of Dengue Virus Infection is Independent of DC-SIGN Internalization Signals," The Journal of Biological Chemistry, 280, (2005), pp. 23698-23708.

Lanier, Lewis, et al, "Immunoreceptor DAP12 bearing a tyrosine-based activation motif is involved in activating NK cells," Nature, 391, (1998), pp. 703-707.

Lasic, Danilo, et al, "Liposomes Revisited," Science, vol. 267., Issue 5202, pp. 1275-1276.

Lasic, Danilo, et al, "The 'Stealth' Liposome: A Prototypical Biomaterial," Chemical Reviews, 95, (1995), pp. 2601-2627.

Lehrman, Mark, et al., "The Binding of Fucose-containing Glycoproteins by Hepatic Lectins," The Journal of Biological Chemistry, 261, (1986), pp. 7426-7432.

Leteux, Christine, et al., "The Cysteine-rich Domain of the Macrophage Mannose Receptor Is a Multispecific Lectin That Recognizes Chondroitin Sulfates A and B and Sulfated Oligosaccharides of Blood Group Lewis$^a$ and Lewis$^x$ Types in Addition to the Sulfated $N$-Glycans of Lutropin," Journal of Experimental Medicine, 191, (2000), pp. 1117-1126.

Mackenzie, John S., et al, "Emerging flaviviruses: the spread and resurgence of Japanese encephalitis, West Nile and dengue viruses," Nature Medicine Supplement, 10-12, (2004), pp. S98-S109.

McDonald, Christine, et al., "Peptidoglycan Signaling in Innate Immunity and Inflammatory Disease," The Journal of Biological Chemistry, 280-21, (2005), pp. 20177-20180.

Miller, A. Dusty, "Progress Toward Human Gene Therapy," The Journal of the American Society of Hematology, 76, (1990), pp. 271-278.

Michell, Daniel A., et al., "A Novel Mechanism of Carbohydrate Recognition by the C-type Lectins DC-SIGN and DC-SGNR," The Journal of Biological Chemistry, 276, (2001), pp. 28939-28945.

Miyazaki, Toshio, "Structural examination of an alkali-extracted, water-soluble heteroglycan of the fungus *Gandoerma ludicum*," Carbohydrate Research, 109 (1982) pp. 290-294.

Mizuno et al., "Gioma, Interferon, Gene therapy, Liposome, Transfection," Sinkei Geka, 20, (1992), pp. 547-551.

Modis, Yorgo, et al., "Variable Surface Epitopes in the Crystal Structure of Dengue Virus Type 3 Envelope Glycoprotein," Journal of Virology, 79-2, (2005), pp. 1223-1231.

Muller, Yves, et al, "VEGF and the Fab fragment of a humanized neutralizing antibody: crystal structure of the complex at 2.4 A resolution and mutational analysis of the interface," Structure, 6, (1998), pp. 1153-1167.

Navarro-Sanchez, Erika, et al., "Dendritic-cell-specific ICAM#-grabbing non-integrin is essential for the productive infection of human dendritic cells by mosquito-cell-derived dengue viruses," European Molecular Biology Organization Reports, 4-7, (2003), pp. 723-728.

Oko, Naoto, et al, "Real-time analysis of liposomal trafficking in tumor-bearing mice by use of positron emission tomography, "Biochimica et Biophysica Acta 1238 (1995), pp. 86-90.

Palma, Angelina S., et al., "Ligands for the β-Glucan Receptor, Dectin-1, Assigned Using "Designer" Microarrays of Oligosaccharide Probes (Neoglycolipids) Generated from Glucan Polysaccharides," The Journal of Biological Chemistry, 281, (2006), pp. 5771-5779.

Palmer, Dupeh R., et al., "Differential Effects of Dengue Virus on Infected and Bystander Dendritic Cells," Journal of Virology, 79-4, (2005), pp. 2432-2439.

Palucka, Anna K., "Dengue Virus and dendritic cells," Nature Medicine, 6-7, (2000), pp. 748-749.

Pang, Tikki, et al., "Of cascades and perfect storms: the immunopathogenesis of dengue haemorrhagic fever-dengue shock syndrome (DHF/DSS)," Immunology and Cell Biology, 85, (2007), pp. 43-45.

Pardridge, William M., et al., "Vector-mediated delivery of polyamide ("peptide") nucleic acid analogue through the blood-brain barrier in vivo," Pharmacology, 91, (1995), pp. 5592-5596.

Pitard, Vincent, et al., "Production and characterization of monoclonal antibodies against the leukemia inhibitory factor low affinity receptor, gp190," Journal of Immunological Methods, 205, (1997), pp. 177-190.

Pokidysheva, Elena, et al., "Cryo-EM Reconstruction of Dengue Virus in Complex with the Carbohydrate Recognition Domain of DC-SIGN," Cell, 124, (2006), pp. 485-493.

Prat, Maria, et al. "Agonistic monoclonal antibodies against the Met receptor dissect the biological responses to HGF," Journal of Cell Science, 111, (1998), pp. 237-247.

Remy, Jean-Serge, et al. "Gene Transfer with a Series of Lipophilic DNA-Binding Molecules," Bioconjugate Chern. 5 (1994). pp. 647-654.

Robinson, Matthew J., et al., "Myeloid C-type lectins in innate immunity," Nature Immunology, 7-12, (2006), pp. 1258-2908.

Rosenfeld, Melissa A., et al., "Adenovirus-Mediated Transfer of a Recombinant α1-Antitrypsin Gene to the Lung Epithelium in Vivo," Science, 252, (1991), pp. 431-434.

Rosenfeld, Melissa A., et al., "In Vivo Transfer of the Human Cystic Fibrosis Transmembrane Conductance Regulator Gene to the Airway Epithelium," Cell, 68 (1992), pp. 143-155.

Rubinson, Douglas A., "A lentivirus-based system to functionally silence genes in primary mammalian cells, stem cells and transgenic mice by RNA interference," Nature Genetics, vol. 33, Mar. 2003, pp. 401-406.

Schroeder, Ulrike, et al., "Diffusion Enhancement of Drugs by Loaded Nanoparticles in Vitro," Prog. Neuro-Psychopharmacol & Biol. Psychiat., 23, (1999), pp. 941-949.

Shao, Bao-Mei, et al., "Immune receptors for polysaccharides from *Ganoderma lucidum*," Biochemical and Biophysical Research Communication, 323, (2004), pp. 133-141.

Shiao, Ming-Shi, "Natural Products of the Medicinal Fungus *Ganoderma lucidum*: Occurrence, Biological Activities, and Pharmacological Functions," The Chemical Record, 3, (2003), pp. 172-180.

Shresta, Sujan, et al., "Murine Model for Dengue Virus-Induced Lethal Disease with Increased Vascular Permeability," Journal of Virology, 80-20, (2006), pp. 10208-10217.

Shresta, Sujan, et al. "Critical Roles for Both STAT1-Dependent and STAT1-Independent Pathways in Control of Primary Dengur Virus Infection in Mice," The Journal of Immunology, 175, (2005), pp. 3946-3954.

Soilleux, Elizabeth J., et al., "Cutting Edge: DC-SIGN; a Related Gene, DC-SIGNR; and CD23 Form a Cluster on 19p13$^{1,2}$," The Journal of Immunology, 165, (2002), pp. 2937-2942.

Stahl, Philip D., "The Macrophage Mannose Receptor: Current Status," Am. J. Respir. Cell Mol. Biol., 2, (1990), pp. 317-318.

Stahl, Philip D., et al., "The mannose receptor is a pattern recognition receptor involved in host defense," Current Opinion in Immunology, 10, (1998), pp. 50-55.

Stambach, Nicola S., et al., "Characterization of carbohydrate recognition by langerin, a C-type lectin of Langerhans cells," Glvcobiology, 13-5, (2003), pp. 401-410.

Terryman, Roy E., et al., "Glutamate Receptor Antibodies Activate a Subset of Receptors and Reveal an Agonist Binding Site," Neuron, 14, (1995), pp. 755-762.

Tassaneetrithep, Boonrat, et al., "DC-SIGN (CD209) Mediates Dengue Virus Infection of Human Dendritic Cells," The Journal of Experimental Medicine, 197-7, (2003), pp. 823-829.

Trowsdale, John, et al., "The genomic context of natural killer receptor extended gene families," Immunological Reviews, 181, (2001), pp. 20-38.

Tyler, Beth M., et al., "Peptide nucleic acids targeted to the neurotensin receptor and administered I.P. cross the blood-brain barrier and specifically reduce gene expression," Neurobiology, 96, (1999), pp. 7053-7058.

Tyler, Beth M., et al., "Specific gene blockade shows that peptide nucleic acids readily enter neuronal cells in vivo," FEBS Letters, 421, (1998), pp. 280-284.

Usia, Taichi, et al., "Isolation and characterization of antitumor active β-D-glucans from the fruit bodies of *Ganoderma applanatum*," Carbohydrate Research, 115 (1983), pp. 273-280.

Van Liempt, Ellis et al., "Molecular Basis of the Differences in Binding Properties of the Highly Related C-type Lectins DC-SIGN and L-SIGN to Lewis X Trisaccharide and *Schistosoma mansoni* Egg Antigens," The Journal of Biological Chemistry, vol. 279, No. 32, (2004), pp. 33161-33167.

Vaughan, Tristan J., et al., "Human Antibodies with Sub-nanomolar Affinities Isolated from a Large Non-immunized Phage Display Library," Nature Biotechnology, 14, (1996), pp. 309-314.

Wahl, Richard L., et al., "Improved Radio imaging and Tumor Localization with Monoclonal f(ab')2," The Journal of Nuclear Medicine, 24, (1983), pp. 316-325.

Wang, Yuan-Yuan, et al., "Studies on the Immuno-Modulating and Antitumor Activities of *Ganoderma lucidum* (Reishi) Polysaccharides: Functional and Proteomic Analyses of a Fucose-Containing Glycoprotein Fraction Responsible for the Activities," Bioorganic & Medicinal Chemistry, 10, (2002), pp. 1057-1062.

Washington, A. Valance, et al., "A TREM family member, TLT-1, is found exclusively in the α-granules of megakaryocytes and platelets," Blood, 104-4, (2004), pp. 1042-1047.

Washington, A. Valance, et al., "Initial characterization of TREM-like transcript (TLT)-1: a putative inhibitory receptor within the TERM cluster," Blood, 100-10, (2002), pp. 3822-3824.

Wilder-Smith, Annelies, et al., "Dengue in Travelers," The New England Journal of Medicine, 353:9, (2005), pp. 924-932.

Willment, Janet A., et al., "Characterization of the Human β-Glucan receptor and Its Alternatively Spliced Isoforms," The Journal of Biological Chemistry, vol. 276, No. 47, (2001), pp. 43818-43823.

Wu, Shu-Fen, et al., "Antiviral Effects of an Iminosugar Derivative on Flavivirus Infections," Journal of Virology, 76-8, (2002), pp. 3596-3604.

Wu, Shuenn-Jue L., et al., "Human skin Langerhans cells are targets of dengue virus infection," Nature Medicine, 6, (2000), pp. 816-820.

Yoon, Do-Young, et al., "Antibodies to Domains II and III of the IL-1 Receptor Accessory Protein Inhibit IL-1β Activity But not Binding: Regulation of IL-1 Responses is Via Type I Receptor, Not the Accessory Protein," The Journal of Immunology, 160, (1998), pp. 3170-3179.

Zhu, Jia-Shi, et al., "The Scientific Rediscovery of a Precious Ancient Chinese Herbal Regimen: *Cordycepts sinensis* Part II," The Journal of Alternative and Complementary Medicine, 4-4, (1998), pp. 429-457.

Zhu, Zhenping, et al., "Inhibition of Vascular Endothelial Growth Factor-induced Receptor Activation with Anti-Kinase Insert Domain-containing Receptor Single-Chain Antibodies from a Phage Display Library," Cancer Research, 58, (1998), pp. 3209-3214.

Barber, D. L., et al., "Restoring function in exhausted CD8 T cells during chronic viral infection", Nature, vol. 439, (Feb. 9, 2006) pp. 682-687.

Boonak, K., et al, "Role of dendritic cells in antibody-dependent enhancement of Dengue virus infection," Journal of Virology, vol. 82(8), (Feb. 13, 2008), pp. 3939-3951.

Mohler et al., "Soluble Tumor Necrosis Factor (TNF) Receptors Are Effective Therapeutic Agents in Lethal Endotoxemia and Function Simultaneously as Both TNF Carriers and TNF Antagonists," The Journal of Immunology, vol. 151, No. 3, (1993) pp. 1548-1561.

Martinez-Pomares et al., "Potential role of the mannose receptor in antigen transport," Immunology Letters, vol. 65, (1999), pp. 9-13.

Linehan et al., "Endogenous ligands of carbohydrate recognition domains of the mannose receptor in murine macrophages, endothelial cells and secretory cells; potential relevance to inflammation and immunity," European Journal of Immunology, vol. 31, (2001), pp. 1857-1866.

Chazenbalk et al., "Interactions between the mannose receptor and thyroid autoantigens," Clinical and Experimental Immunology, vol. 139, (2005), pp. 216-224.

* cited by examiner

A.

B.

A.

B.

C.

D.

E.

| No | Probe | Binding with GLPS F3 | Binding with GLPS F3C |
|---|---|---|---|
| 1 | CLEC1A/CLEC-1 | - | - |
| 2 | CLEC2B/AICL | - | - |
| 3 | CLEC4A/DCIR | - | - |
| 4 | CLEC4C/BDCA-2 | - | - |
| 5 | CLEC4D/CLEC-6 | - | - |
| 6 | CLEC4E/MINCLE | - | - |
| 7 | CLEC4F/KCLR | +++ | +++ |
| 8 | CLEC4H2/HBVxAgBP | - | - |
| 9 | CLEC4K/Langerin | - | - |
| 10 | CLEC4L/DC-SIGN | - | - |
| 11 | CLEC4M/DC-SIGNR | ++++ | ++++ |
| 12 | CLEC5A/MDL1 | - | - |
| 13 | CLEC6A/Dectin-2 | - | - |
| 14 | CLEC7A/Dectin-1 | ++++ | ++++ |
| 15 | CLEC12A/CLL-1 | - | - |
| 16 | CLEC13A/BIMLEC | - | - |
| 17 | MAFAL | - | - |
| 18 | NKG2D | - | - |
| 19 | Siglec11 | - | - |
| 20 | TLT-1 | - | - |
| 21 | TLT-2 | +++++ | - |
| 22 | TREM-1 | - | - |
| 23 | TREM-2 | - | - |
| 24 | mTLT1 | - | - |
| 25 | mTLT4 | - | - |
| 26 | mTREM1 | - | - |
| 27 | mTREM2 | - | - |
| 28 | hIgG1 | - | - |

| No | Polysaccharides sample | Dectin-1.Fc | DC-SIGNR.Fc | mKCR.Fc | TLT-2.Fc | hIgG1 |
|---|---|---|---|---|---|---|
| 1 | F3 | +++++ | +++++ | +++++ | +++++ | - |
| 2 | Reishi 1 | +++ | + | - | - | - |
| 3 | Reishi 2 | +++ | ++ | + | - | - |
| 4 | Reishi 3 | + | + | + | ++ | - |
| 5 | Crude extract | ++ | + | - | - | - |
| 6 | *Dendrobiun huoshanense* polysaccharide | - | - | - | - | - |
| 7 | *Cordyceps sinensis* polysaccharide | ++++ | + | + | - | - |
| 8 | Mushroom polysaccharides L | + | +++ | - | - | - |
| 9 | Mushroom polysaccharides M | ++ | + | - | - | - |
| 10 | dH₂O | - | - | - | - | - |

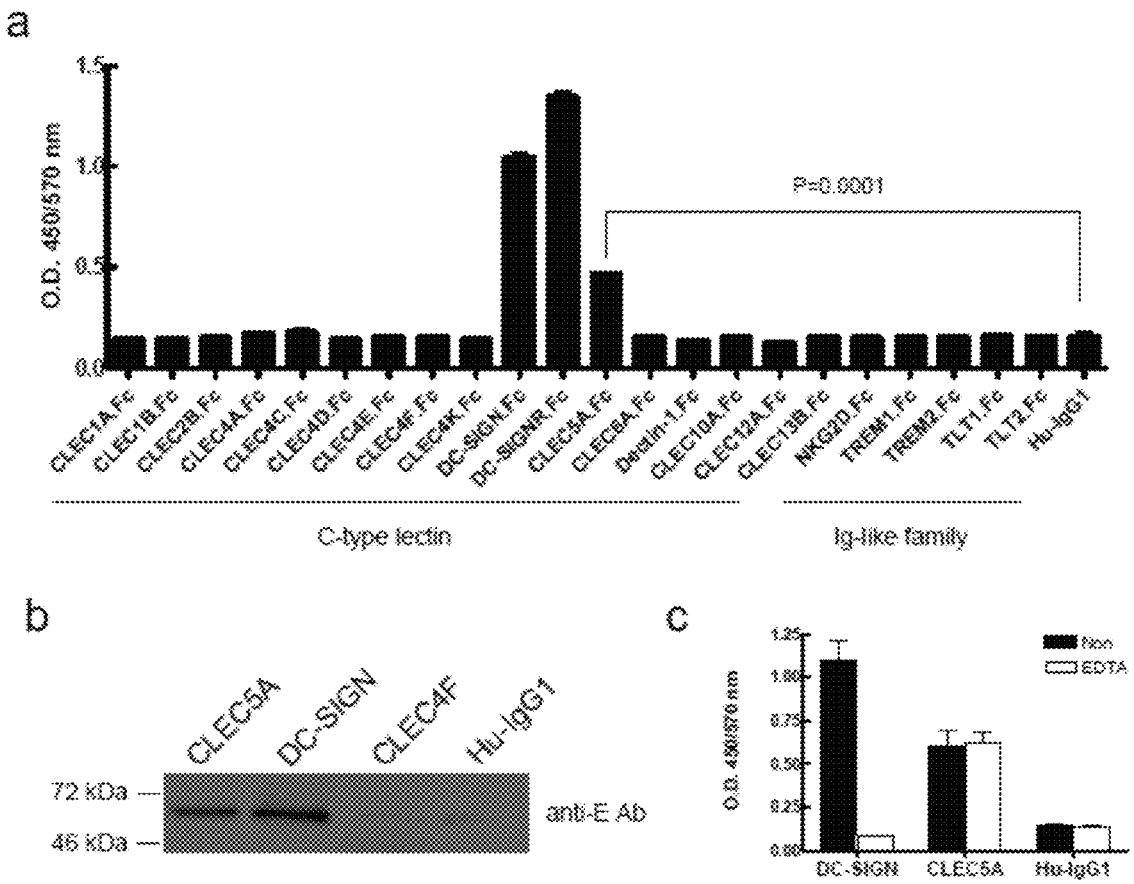
Figure 16 A-C

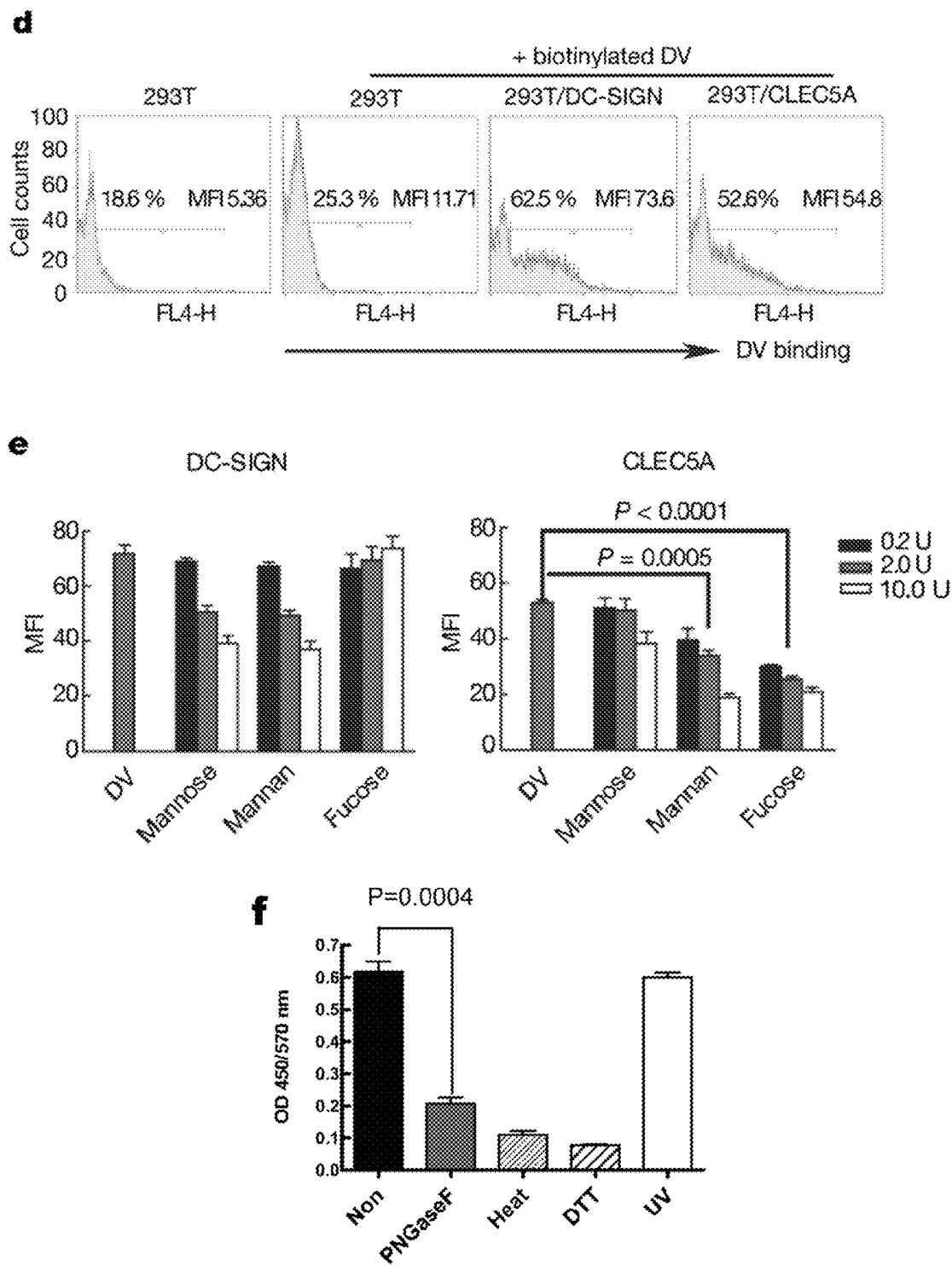
Figure 16 D-F

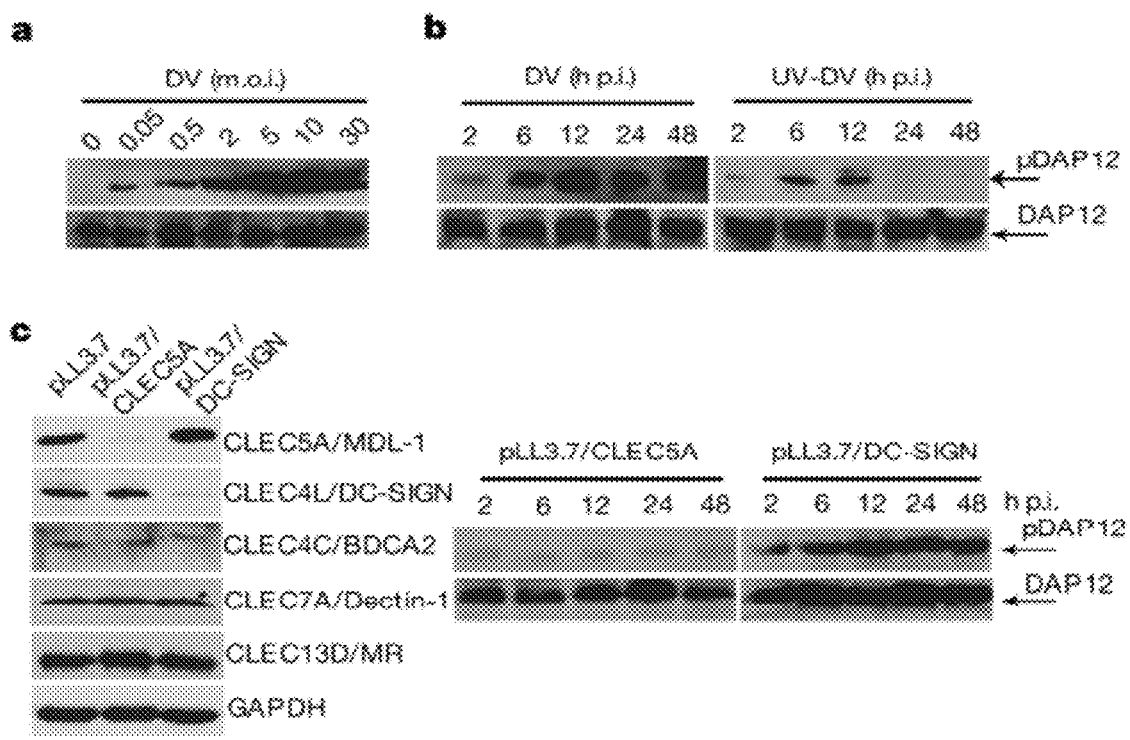
Figure 18 A-C

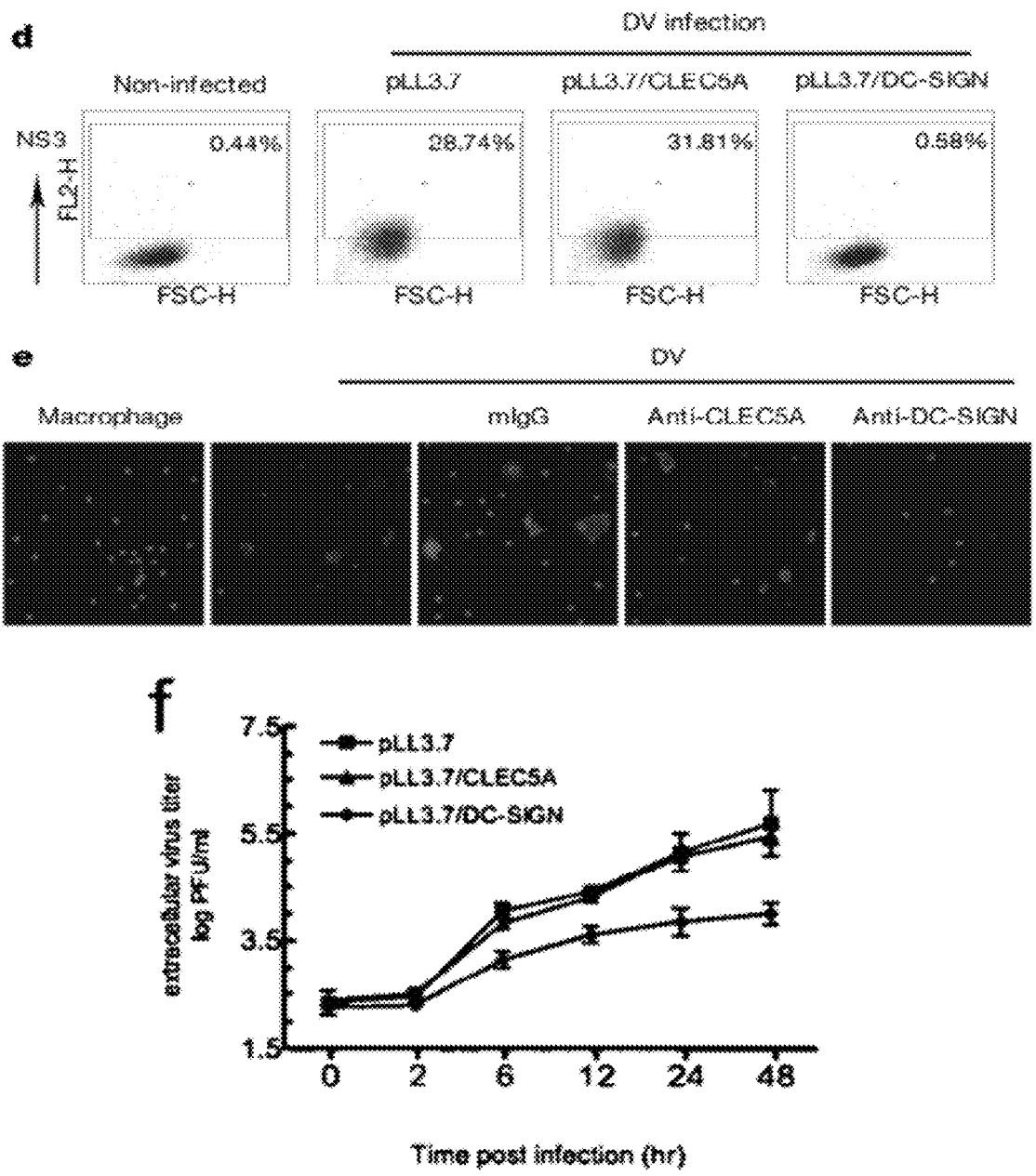
Figure 18 D-F

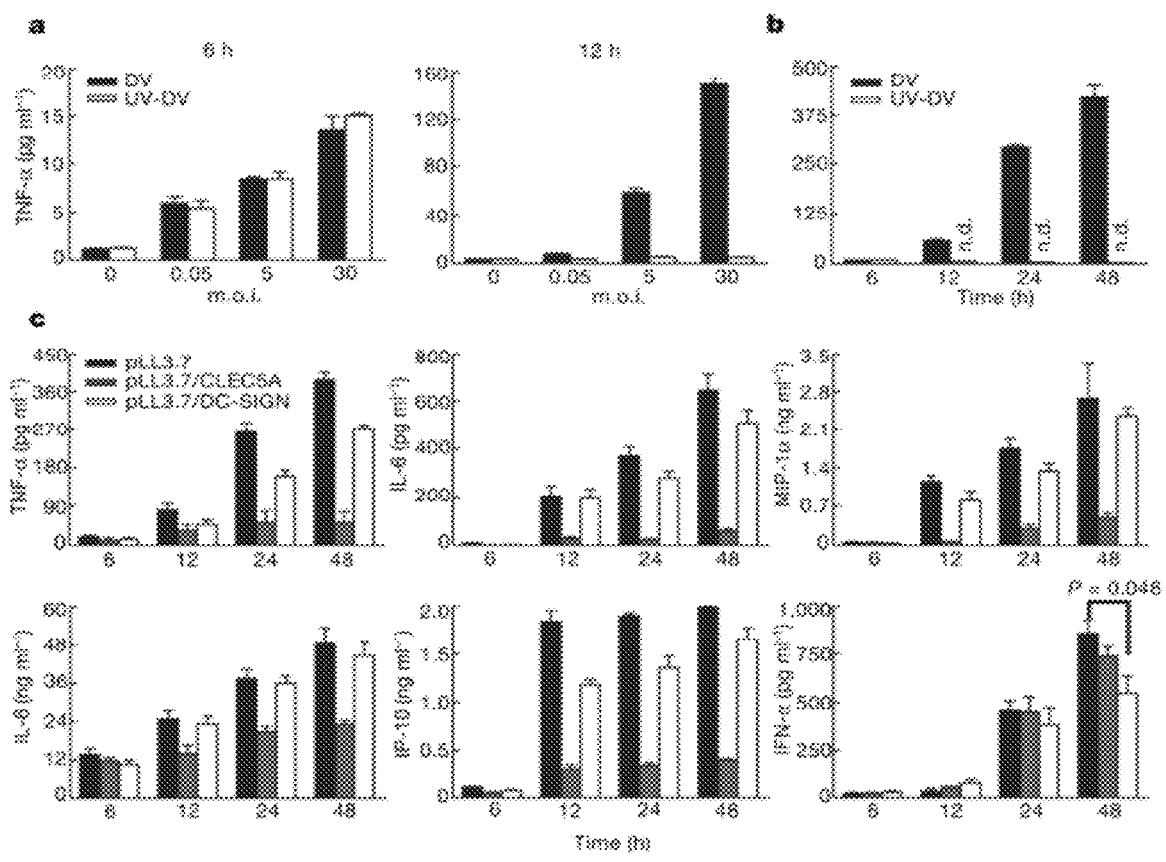
Figure 19 A-C

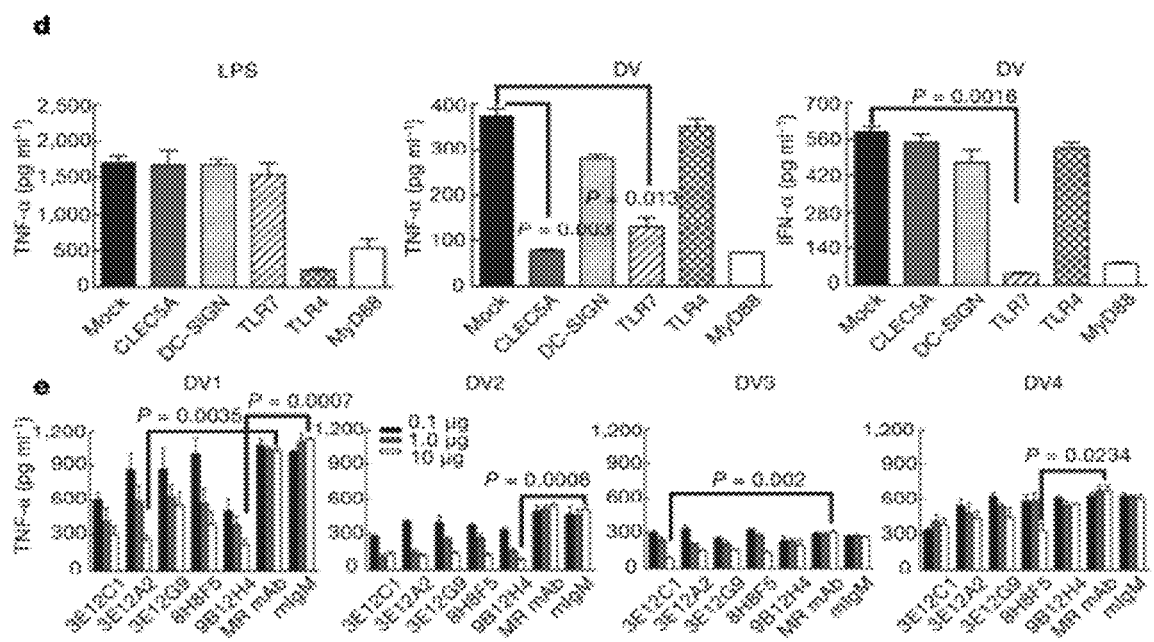
Figure 19 D-E

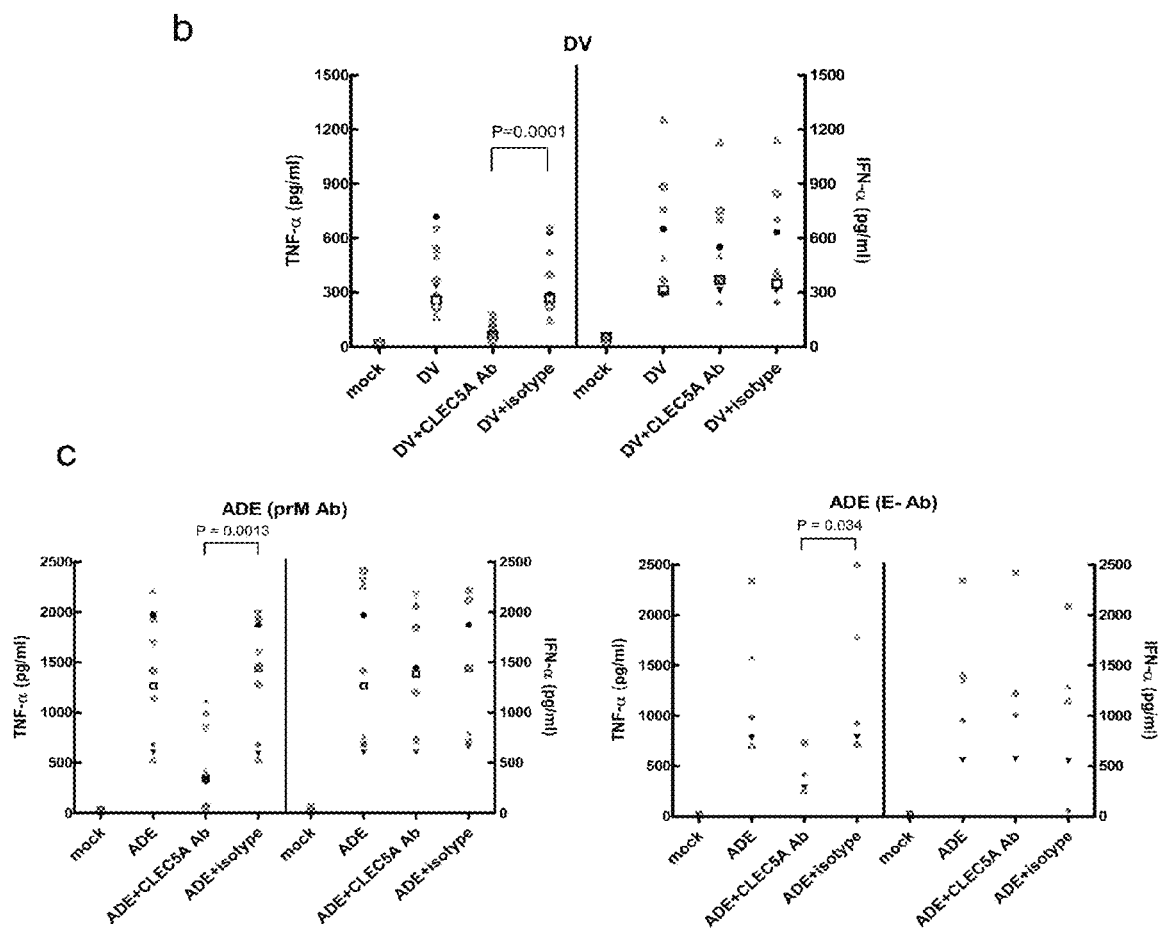
Figure 20 B-C

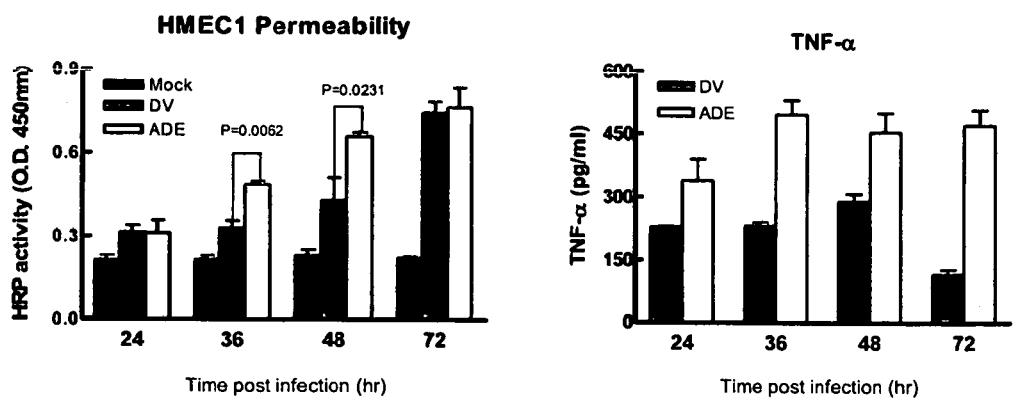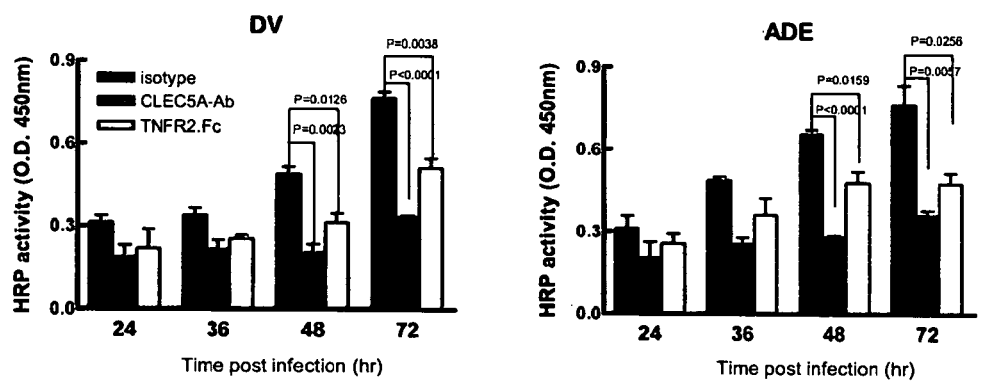
Figure 21 A-B a
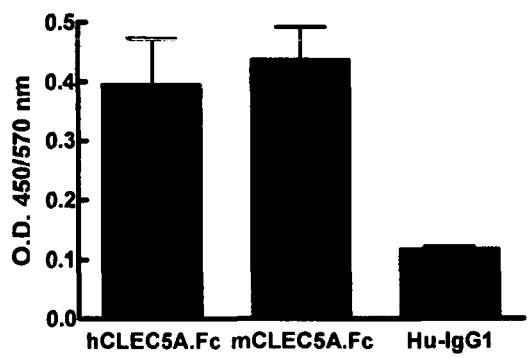
b
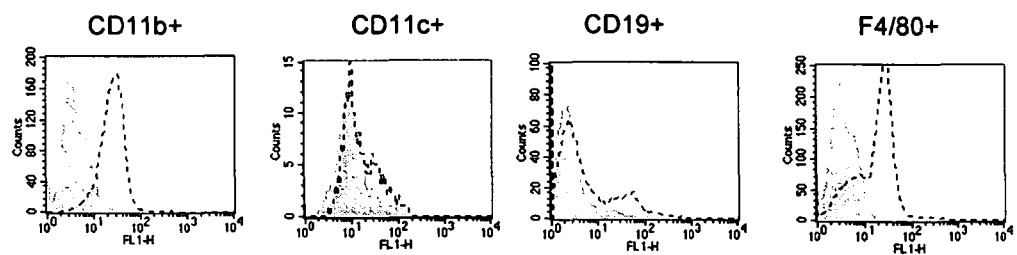
c
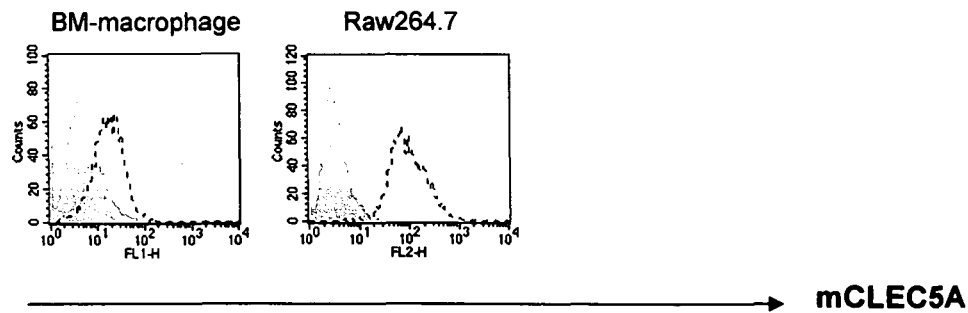
mCLEC5A
Figure 22 A-C

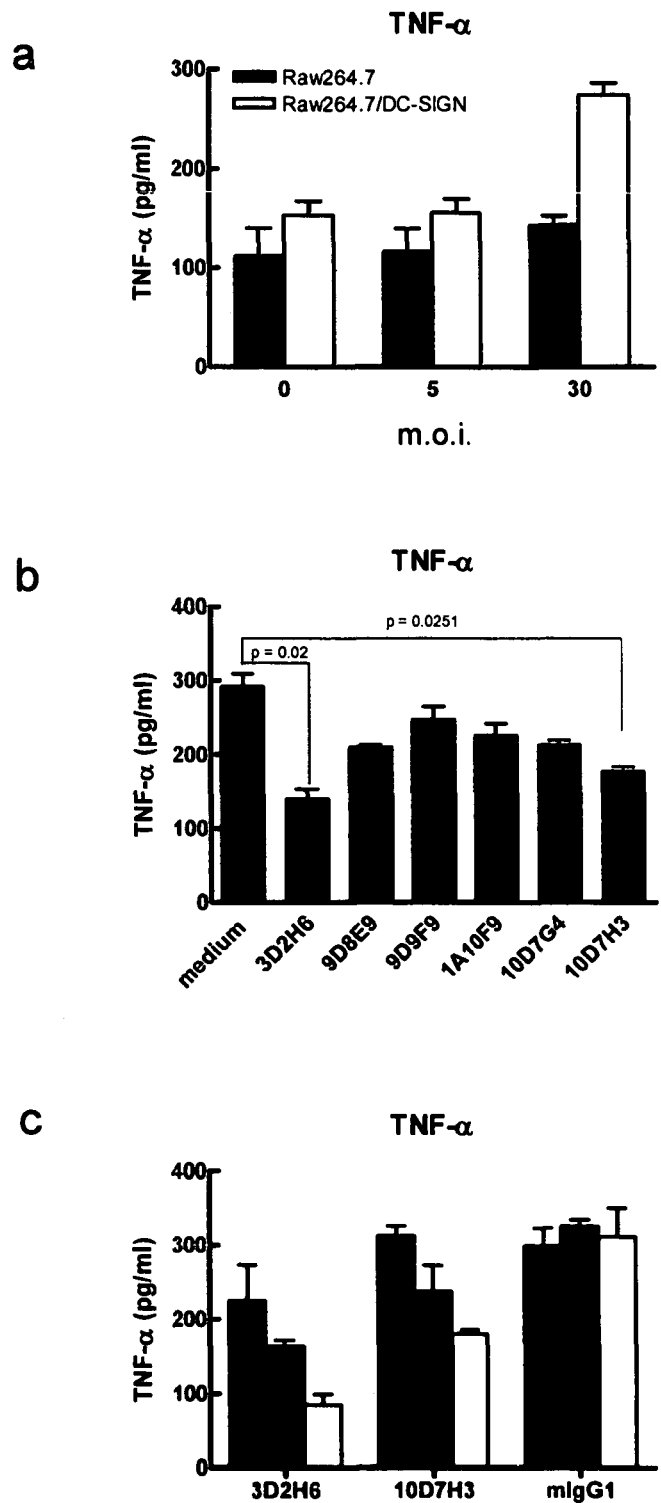
Figure 23 A-C

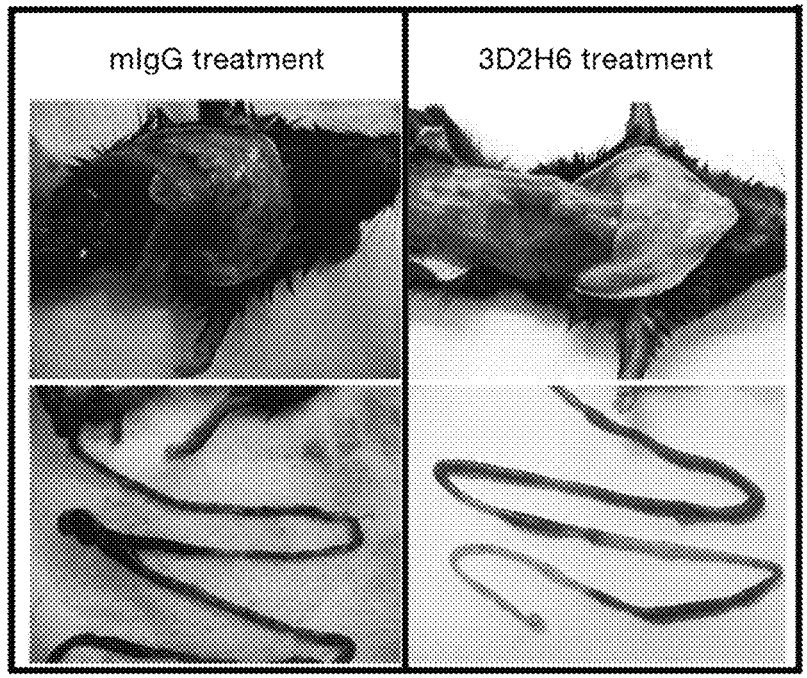
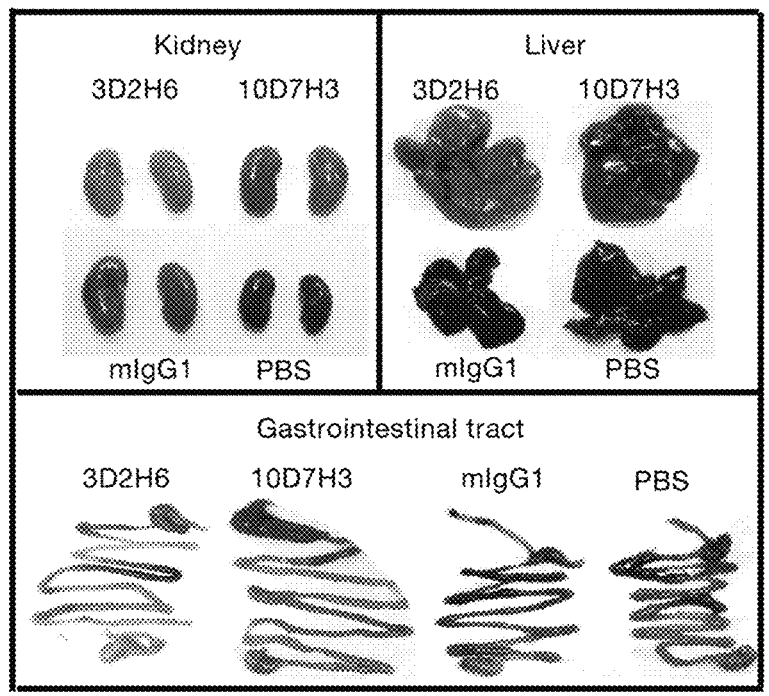
Figure 25 A-B

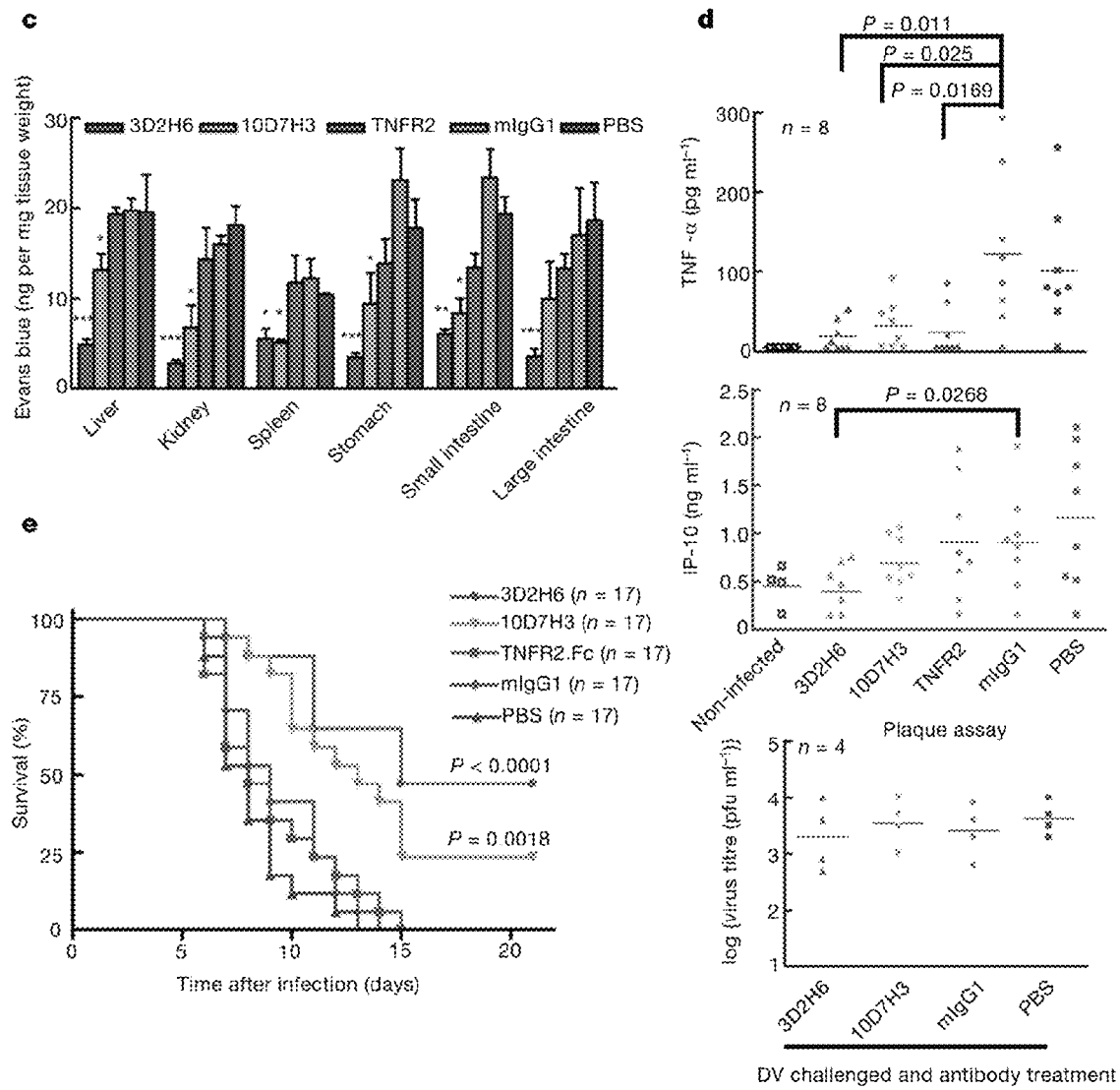
Figure 25 C-E

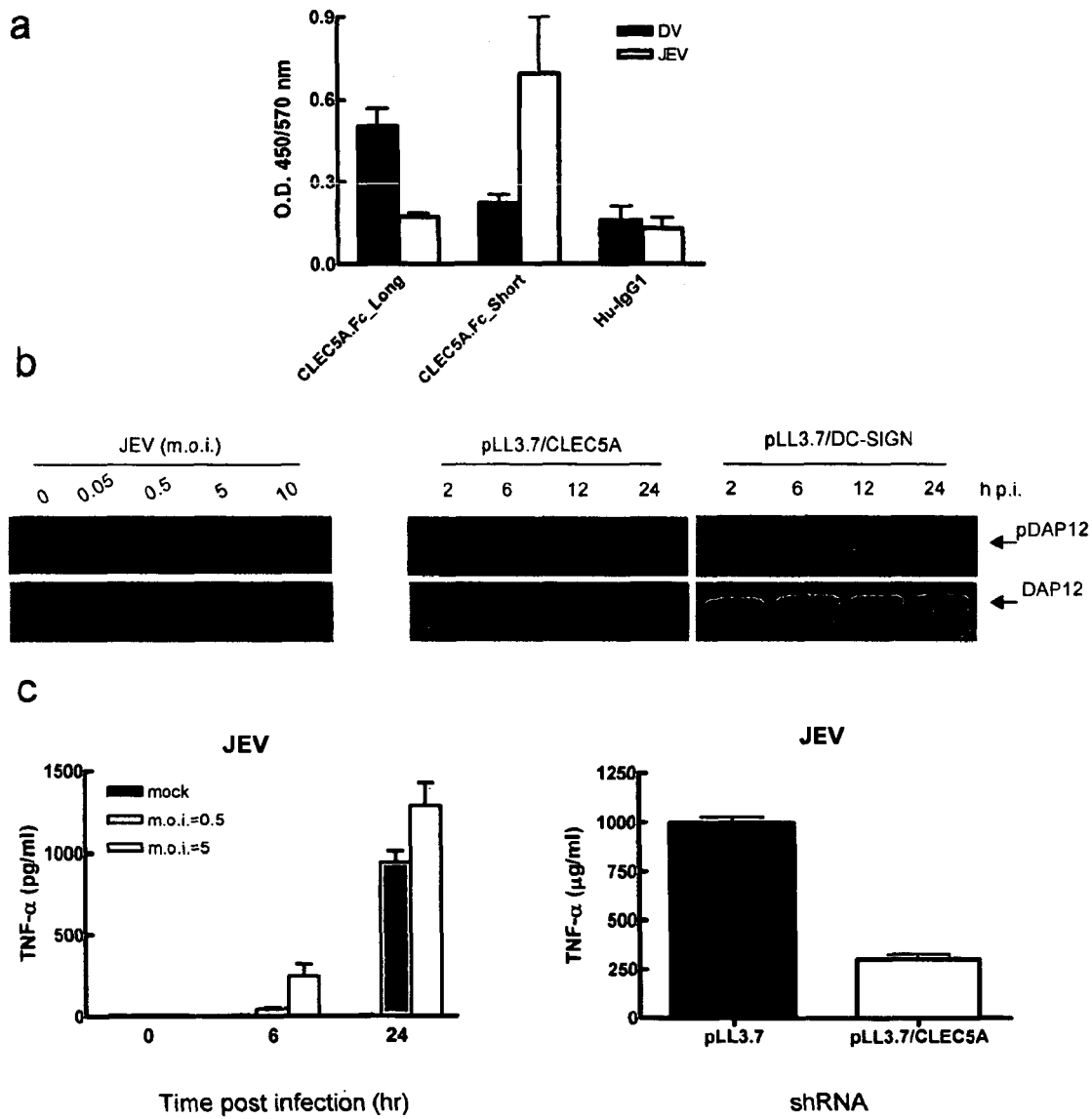
Figure 26 A-C

COMPOSITIONS AND METHODS FOR IDENTIFYING RESPONSE TARGETS AND TREATING FLAVIVIRUS INFECTION RESPONSES

This application is a divisional application of U.S. patent application Ser. No. 12/079,576, filed Mar. 27, 2008, which claims the Paris Convention priority and is a continuation-in-part of U.S. patent application Ser. No. 11/469,270, filed Aug. 31, 2006, which claims the Paris Convention priority of U.S. Provisional Patent Application Ser. No. 60/713,463, filed Aug. 31, 2005. The contents of all prior applications are incorporated herein by reference in their entirety.

This work was supported by grant 94F008-5, NSC 95-2320-B-010-010 and NSC 95-3112-B-010-017 from the National Sciences Council, Taiwan. This work was also supported by grant 94M002-1 from the Academia Sinica, Taiwan, and by grant 95A-CT8G02 from the National Yang-Ming University.

BACKGROUND

Citation to any reference in this specification is not, and should not be taken as, an acknowledgment or any form of suggestion that this reference forms part of the common general knowledge or of the prior art in any country. All references cited herein are specifically incorporated herein by reference in their entirety.

The immune system enables a host organism to discriminate self from non-self antigens, as well as to recognize and eradicate invasive pathogens. The adaptive immunity system relies on highly polymorphic molecules, such as class I and class II antigens of the major histocompatibility complex (MHC), T cell receptors, and B cell receptors, to present antigens to T cells and B cells, thus leading to the activation of immune system. The mechanism by which the innate immunity system can recognize these diverse antigens remained unsolved until the emergence of the concept of 'pattern recognition receptors (PPRs)' proposed by Janeway (Janeway, 1989, Cold Spring Harb Symp Quant Biol 54 Pt 1, 1-13). This hypothesis was later proved correct by the identification of pathogen-associated molecular patterns (PAMPs) which are recognized by TOLL-like receptors (Aderem and Ulevitch, 2000 Nature 406, 782-7; Akira and Takeda, 2004, Nat Rev Immunol 4, 499-511; Athman and Philpott, 2004, Curr Opin Microbiol 7, 25-32), lectin receptors (Cambi and Figdor, 2003, Curr Opin Cell Biol 15, 539-46), immunoglobulin-like (Ig-like) receptors (Daws et al., 2003, J Immunol 171, 594-9), and NOD proteins (Athman and Philpott, 2004, Curr Opin Microbiol 7, 25-32), and others (Liu et al., 2001, J Biol Chem 276, 34686-94; McDonald et al., 2005, J Biol Chem 280, 20177-80).

In addition to the well characterized PAMPs recognized by TOLL-like receptors (Akira and Takeda, 2004, Nat Rev Immunol 4, 499-511), recent study indicates that the host immune system can recognize invasive pathogens through specific carbohydrate antigens. For example, mannose receptors can recognize the high mannose sugar moiety expressed on the surface of pathogens (Stahl and Ezekowitz, 1998, Curr Opin Immunol 10, 50-5), while the Dectin-1 receptor can bind specifically to β-glucan, the major backbone of polysaccharides on fungus walls (Brown and Gordon, 2001, Nature 413, 36-7; Herre et al., 2004, Mol Immunol 40, 869-76). These results suggest that the carbohydrate structures associated with pathogens are one of the targets recognized by the innate immunity receptors of immune cells.

The funguses species *Ganoderma* and *Cordyceps* are the most popular herbal drugs taken in China to medicinal purposes. Polysaccharides extracted from *Ganoderma lucidum* (also known as Ling zhi, *Reishi*) have been used in traditional Chinese medicine as anti-tumor agents and as immuno-modulating agents (Lien, 1990, Prog Drug Res 34, 395-420; Wang et al., 2002, Bioorg Med Chem 10, 1057-62; Shiao, 2003, Chem Rec 3, 172-80), while those extracted from *Cordyceps sinensis* (*Cordyceps*, Caterpillar fungus) have been shown to alter apoptotic homeostasis, and to improve respiratory, renal, and cardiovascular functions (Buenz et al., 2005, J Ethnopharmacol 96, 19-29; Zhu et al., 1998, J Altern Complement Med 4, 289-303; Zhu et al., 1998, J Altern Complement Med 4, 429-57), as well as to increase whole body sensitivity to insulin (Balon et al., 2002, J Altern Complement Med 8, 315-23). However, the polysaccharide composition of the extracts vary when they the polysaccharides are extracted from different sources, from different strains, and under different growing conditions.

Analytical methods relying on high-performance liquid chromatography (HPLC) and proton-nuclear magnetic resonance have been applied to investigate the components of polysaccharides isolated from *Ganoderma lucidum* and *Cordyceps sinensis* (He and Seleen, 2004, Int. J. Med. Mushrooms 6, 253). However, the HPLC chromatogram is based on the comparison with ganoderic acid A and C (two major triterpenes of *Ganoderma lucidum*) or adenosine. It is still difficult to know whether the extracts contain the active components of polysaccharides based on the mass spectrum.

Cellular receptors are identified that induce plasma leakage and other negative effects when infected with flaviviruses, such as dengue virus or Japanese encephamyelitis virus. Using fusion proteins disclosed herein, the receptors to which a pathogen, such as flavivirus, binds via glycan binding are determined. Once the receptors are determined, the effect of binding to a particular receptor may be determined, wherein targeting of the receptors causing a particular symptom may be targeted by agents that interrupt binding of the pathogen to the receptor. Accordingly, in the case of dengue virus and Japanese encephamyelitis virus, TNF-α is released when the pathogen binds to the Dengue Virus Lectin Receptor 1 (DVLR1)/CLEC5A receptor. Interrupting the DVLR1/CLEC5A receptor with monoclonal antibodies reduced TNF-α secretion without affecting secretion of cytokines responsible for viral clearance thereby increasing survival rates in infected mice from nil to around 50%.

SUMMARY

According to a feature of the present disclosure, a method is disclosed comprising obtaining a complement of fusion proteins, each fusion protein comprising a binding domain of a receptor and a domain that provides for affixing to a substrate, contacting the fusion protein with a pathogen to determine if the pathogen binds to the binding domain of at least one fusion protein of the complement of fusion proteins, and detecting whether the pathogen is bound to the fusion protein. The complement of fusion proteins represents a plurality of different binding domains of at least one receptor.

According to a feature of the present disclosure, a method is disclosed comprising obtaining cells susceptible to a pathogen, knocking down at least one cellular receptor gene, contacting the cells with the pathogen, and measuring the level of cytokine secretion of the cells.

According to a feature of the present disclosure, a method is disclosed comprising identifying at least one cellular receptor that binds to a ligand displayed by a pathogen and administering an agent to an animal infected with the pathogen to interrupt binding of the ligand to the receptor to modulate an effect of the pathogen.

According to a feature of the present disclosure, a method is disclosed comprising providing an effective amount of an agent to modulate the effect of a pathogen infecting an animal to modulate the effect of the pathogen on the animal. The agent is directed to at least one cellular receptor of the animals native cells to prevent the receptor from binding to a ligand presented by the pathogen.

According to a feature of the present disclosure, a method is disclosed comprising providing an effective amount of an anti-DVLR1/CLEC5A antibody to an animal infected with dengue virus, wherein the anti-DVLR1/CLEC5A antibody prevents binding of a ligand presented by a dengue virus particle from binding to the DVLR1/CLEC5A receptor, wherein secretion of TNF-α is inhibited.

According to a feature of the present disclosure, a method is disclosed comprising providing an effective amount of an anti-DVLR1/CLEC5A antibody to an animal infected with Japanese encephamyelitis virus, wherein the anti-DLVR1/CLEC5A antibody prevents binding of a ligand presented by a Japanese encephalitis particle from binding to the DVLR1/CLEC5A receptor, wherein secretion of TNF-α is inhibited.

According to a feature of the present disclosure, a method is disclosed comprising providing to an animal infected with dengue virus an effective amount of an agent that at least partially inhibits the secretion of at least one pro-inflammatory cytokine without affecting the secretion of interferon-α.

According to a feature of the present disclosure, a mouse is disclosed comprising a mouse susceptible to dengue virus infection, and an sh-RNA particle to knock down the DLVR1/CLEC5A receptor in the mouse.

According to a feature of the present disclosure, a composition is disclosed comprising a pharmaceutical preparation containing an effective amount of an antibody directed against at least one cellular receptor of an animal to modulate the effects of a pathogen infection in the animal. The modulation comprises at least inhibition in pro-inflammatory cytokine secretion of the animals cells and does not affect secretion of cytokines that effect viral clearance.

According to a feature of the present disclosure, a composition is disclosed comprising a pharmaceutical preparation containing an effective amount of an antibody directed against the DLVR1/CLEC5A receptor of an animal infected with dengue virus to modulate the effects of the dengue virus infection in the animal. The modulation comprises at least inhibition in pro-inflammatory cytokine secretion the animals cells and does not affect secretion of cytokines that effect viral clearance.

BRIEF DESCRIPTION OF THE DRAWINGS

The patent or application contains at least one drawing executed in color. Copies of this patent or patent application publication with color drawings will be provided by the Office upon request and payment of the necessary fee. The above-mentioned features and objects of the present disclosure will become more apparent with reference to the following description taken in conjunction with the accompanying drawings wherein like reference numerals denote like elements and in which:

FIG. 1A shows DNA fragments of innate immunity receptors amplified by RT-PCR, then fractionated on 0.8% agarose and visualized by ethidium bromide staining. FIG. 1B shows the expressed recombinant receptor.Fc fusion proteins following electrophoresis on a 12% SDS-PAGE gel;

FIG. 2A shows a dot blot of membrane-immobilized biotinylated GLPS F3 contacted with streptavidin-conjugated horseradish peroxidase (HRP).

FIG. 2B shows a dot blot of membrane-immobilized non-biotinylated GLPS F3 contacted with a Dectin-1.Fc fusion protein, followed by incubation with goat HRP-conjugated anti IgG1 antibody. FIG. 2C shows a dot density analysis of the blot of FIG. 2B. FIG. 2D shows the effects on dot density of competitor β-glucan on the binding of Dectin-1.Fc to membrane-immobilized GLPS F3. FIG. 2E shows a dot blot of immobilized GLPS F3 contacted with Dectin-1.Fc fusion protein followed by incubation with goat HRP-conjugated anti IgG1 antibody in the presence varying amounts of competitor polysaccharides (β-glucan, D-glucose, and D-galactose);

FIG. 3 shows a semi-quantitative analysis of dot blots of membrane-immobilized GLPS F3 and GLPS F3C contacted with 27 different fusion proteins, each comprising the extracellular domain of the listed innate immunity receptor coupled to IgG1 Fc;

FIG. 4A shows a dot blot of membrane-immobilized GLPS F3 and GLPS F3C probed with the 27 fusion proteins listed in FIG. 3. FIG. 4B shows the effect of EDTA on the binding of Dectin-1.Fc, DC-SIGNR.Fc, KCR.Fc, and TLT-2.Fc to membrane immobilized GLPS F3. FIG. 4C shows a dot blot of membrane-immobilized β-glucan probed with Dectin-1.Fc, DC-SIGNR.Fc, KCR.Fc, and TLT-2.Fc fusion proteins;

FIG. 5A shows dot blots of polysaccharide samples probed with Dectin-1.Fc, DC-SIGNR.Fc, KCR.Fc, and TLT-2.Fc fusion proteins. FIG. 5B shows the identity of the sample numbers and provides the dot densities of FIG. 5A in semi-quantitative form;

FIG. 6A shows the amount of biotinylated GLPS-F3 coated onto a microtiter plate as measured using a peroxidase-conjugated avidin assay and reading at OD450 nm to detect the yellow-colored reaction product. FIG. 6B depicts in graphical form the affinity of various receptor.Fc fusion proteins for GLPS-F3 immobilized on a microtiter plate. The absolute binding of each receptor.Fc fusion protein is depicted on the left Y axis (as an OD450 nm reading) and the right Y axis depicts the relative binding in comparison to the binding of Dectin-1.Fc;

FIG. 7 illustrates graphically the percentage binding of various receptor.Fc fusion proteins to GLPS-F3 in a competition assay with the polysaccharides mannan and β-glucan, and with the monosaccharides D-mannose (Man), D-glucose (Glc), N-acetyl-glucosamine (GlcNAc), D-galactose (Gal), N-acetyl-galactosamine (GalNAc), L-fucose (Fuc) and sialic acid;

FIG. 8A shows graphically the binding of receptor.Fc fusion proteins to Dengue Virus, in comparison to a human IgG negative control. FIG. 8B shows a Western blot of immunocomplexes of Dengue Virus with three receptor.Fc fusion proteins and a human IgG negative control, probed with an antibody against the Dengue Virus E protein. FIG. 8C shows graphically that EDTA inhibits the binding of Dengue Virus to DC-SIGN.Fc fusion protein, but not the binding to DVLR1/CLEC5A.Fc fusion protein. FIG. 8D shows the binding of a DVLR1/CLEC5A.Fc fusion protein to Dengue Virus treated with PNGaseF, dithiothreitol (DTT), heat, or UV irradiation, and to untreated Dengue Virus (non);

FIG. 9A shows the expression of DVLR1/CLEC5A in various immune cell types by flow cytometry using an anti-DVLR1/CLEC5A antibody. Expression of DVLR1/CLEC5A is indicated where the DVLR1/CLEC5A profile (dotted line trace) does not match the antibody isotype control (shaded area).

FIG. 9B shows the expression of DC-SIGN in various immune cell types by flow cytometry using an anti-DC-SIGN antibody. Expression of DC-SIGN is indicated where the DC-SIGN profile (dotted line trace) does not match the antibody isotype control (shaded area);

FIG. 10A shows flow cytometry analysis of the expression of NS3 protein using an anti-NS3 antibody in CD14+ macrophages contacted with live or UV irradiated (UV-DV) Dengue Virus, in comparison to a matched antibody isotype control (shaded area). FIG. 10B shows graphically extracellular Dengue virus titers over time for CD14+ macrophages infected with Dengue Virus at different multiplicities of infection (MOI) or with UV irradiated Dengue Virus. FIG. 10C shows an immunoblot illustrating total DAP12 and phosphorylated DAP12 in CD14+ macrophages infected with Dengue virus at different MOIs. FIG. 10D shows an immunoblot illustrating total DAP12 and phosphorylated DAP12 in CD14+ macrophages infected with Dengue virus at different times following infection with live Dengue virus or UV irradiated Dengue virus at MOI=5;

FIG. 11 shows an immunoblot illustrating total DAP12 and phosphorylated DAP12 in CD14+ macrophages electroporated with pLL3.7 vector (control) or with DVLR1/CLEC5A-shRNA prior to infection with Dengue virus;

FIG. 12A shows the secretion of TNF-α at 6 hours after infection of CD14+ macrophages with live or UV-irradiated Dengue Virus at the specified MOIs. FIG. 12B shows the secretion of TNF-α at 12 hours after infection of CD14+ macrophages with live or UV-irradiated Dengue Virus at the specified MOIs. FIG. 12C shows time course measurements of the secretion of TNF-α following infection of CD14+ macrophages;

FIG. 13A shows the expression of DC-SIGN and DVLR1/CLEC5A by Western blot in CD14+ macrophages transfected with DC-SIGN-shRNA or DVLR1/CLEC5A-shRNA, or with vector controls (pWTSI and pLL3.7). FIG. 13B shows flow cytometry analysis of NS3 expression (using anti-NS3 antibody) in CD14+ macrophages electroporated with DC-SIGN-shRNA, DVLR1/CLEC5A-shRNA, or pLL3.7 vector control prior to infection with Dengue virus. The shaded area is an isotype control for the NS3 antibody. FIG. 13C illustrates a time course analysis of virus titer in the supernatant of CD14+ macrophages electroporated with DC-SIGN-shRNA, DVLR1/CLEC5A-shRNA, or vector controls, prior to infection with Dengue virus at t=0;

Figure 1A:
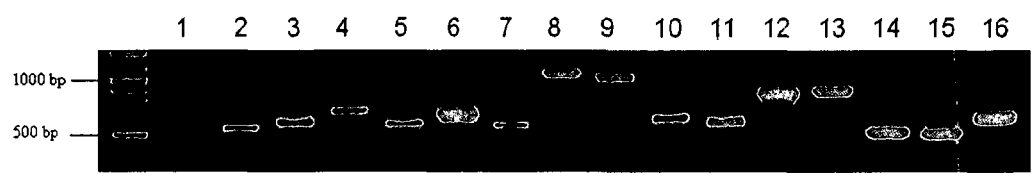
Figure 24:
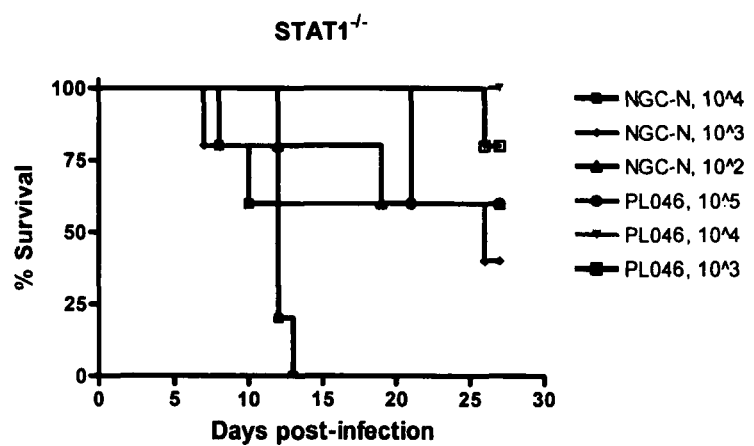

FIG. 16a illustrates graphically the binding of various receptor.Fc fusion proteins to Dengue virus. FIG. 16b shows a Western blot of immunocomplexes of Dengue virus with three receptor.Fc fusion proteins and a human IgG negative control, probed with an antibody against the Dengue Virus E protein. FIG. 16c shows graphically that EDTA inhibits the binding of Dengue Virus to DC-SIGN.Fc fusion protein, but not the binding to DLVR1/CLEC5A fusion protein. FIG. 16d shows the increase in Dengue Virus binding to human 293T cells with the addition of DC-SIGN.Fc and DLVR1/CLEC5A fusion proteins. FIG. 16e shows graphically that the addition of various sugars inhibits the binding of Dengue Virus to DC-SIGN.Fc fusion protein. FIG. 16f illustrates graphically the effect of PNGaseF on Dengue Virus binding to DLVR1/CLEC5A fusion protein;

FIG. 17a illustrates the expression pattern of DC-SIGN in human PBMCs. FIG. 17b illustrates the expression pattern of DLVR1/CLEC5A in human PBMCs;

FIG. 18a shows an immunoblot illustrating dengue virus-induced DAP12 phosphorylation (2 h p.i.) in human macrophages using antibodies to phosphotyrosine and DAP12. FIG. 18b shows immunoblots illustrating the kinetics of DAP12 phosphorylation induced by Dengue Virus and UV-inactivated Dengue Virus. FIG. 18c shows immunoblots illustrating the ability of shRNAs to knock down the expression of DLVR1/CLEC5A and DC-SIGN.Fc fusion proteins and to inhibit Dengue virus (m.o.i.=5)-mediated DAP12 phosphorylation. FIG. 18d shows the effects of shRNAs on Dengue Virus entry and replication in macrophages. FIG. 18e shows the effect of anti-DLVR1/CLEC5A mAb, anti-DCSIGN mAb and mouse IgG on the expression of nonstructural protein NS3. FIG. 18f illustrates graphically a time course analysis of the effect of shRNAs on the Dengue Virus titers of infected macrophages;

FIG. 19a illustrates graphically the dose-dependency of Dengue Virus and UV-inactivated Dengue Virus induced TNF-α secretion by machorphages. FIG. 19b illustrates graphically the kinetics of TNF-α expression after Dengue Virus infection (m.o.i.=5). FIG. 19c illustrates graphically the effects of DLVR1/CLEC5A and DC-SIGN shRNAs on the secretion of TNF-α, IL-6, MIP1-α, IL-8, IP-10, and IFN-α from Dengue Virus-infected macrophages (m.o.i.=5). FIG. 19d illustrates graphically the effects of knock-down experiments using specific shRNAs on the various secretion pathways for Dengue Virus-induced TNF-α and IFN-α secretion. FIG. 19e illustrates graphically the inhibition of TNF-α secretion in response to Dengue Virus serotypes 1-4 by antagonistic antiDVLR1/CLEC5A mAbs. M.R. mAb (anti-1-mannose receptor mAb, mIgG1) and murine IgM (mIgM) were used as negative controls;

FIG. 20a illustrates the expression of NS3 of macrophages infected with dengue virus, dengue virus/anti-E, and dengue virus/anti-prM immunocomplexes. FIG. 20b illustrates the level of TNF-α and IFN-α secretion of macrophages infected with DV2. FIG. 20c illustrates the level of TNF-α and IFN-α secretion of macrophages infected with anti-prM/dengue virus and anti-E/dengue virus immunocomplexes;

FIG. 21a illustrates graphically time course analysis of the permeability of HMEC-1 monolayers and TNF-α levels in the supernatants. FIG. 21b illustrates graphically the inhibitory effects of TNFR2.Fc and anti-DVLR1/CLEC5A on permeabilisation of endothelial monolayers;

FIG. 22a illustrates graphically the binding affinity of dengue virus with human and murine DLVR1/CLEC5A.Fc fusion protein. FIG. 22b shows the expression of mDVLR1/CLEC5A in murine splenocytes. FIG. 22c shows the expression of mDLVR1/CLEC5A in murine bone marrow (BM)-derived macrophage and the murine macrophage cell line Raw264.7;

FIG. 23a illustrates graphically a comparison of TNF-α release from binding of dengue virus to murine macrophage cell line Raw264.7 and Raw264.7 cells stably expressing human DC-SIGN. FIG. 23b illustrates graphically the secretion of TNF-α by Raw 264.7 cells stably expressing human DC-SIGN incubated with DV2 in the presence of mAbs. FIG. 23c illustrates graphically the inhibition of DV2-induced TNF-α release in a dose-dependent manner by anti-mDVLR1 CLEC5A mAbs (3D2H6 and 10D7H3);

FIG. 24 illustrates Kaplan-Meier survival curves of STAT$^{-/-}$ mice challenged with DV2/PL046 and DV2/NGC-C strains;

FIG. 25a illustrates the effect of mAb 3D2H6 and 10D7H3, raised against murine DVLR1/CLEC5A, towards subcutaneous and intestinal hemorrhaging of Dengue Virus-challenged STAT1$^{-/-}$ mice. FIG. 25b illustrates the effect of mAbs against DLVR1/CLEC5A (3D2H6 and 10D7H3) towards plasma leakage into the vital organs of Dengue Virus-challenged STAT1$^{-/-}$ mice. FIG. 25c illustrates graphically vascular permeability of vital organs by extraction of Evan blue from organs. FIG. 25d illustrates the serum levels of TNF-α and IP-10 and virus titers for Dengue Virus-challenged STAT1$^{-/-}$ mice in the presence or absence of anti-DVLR1/CLEC5A mAbs or TNFR2.Fc. FIG. 25e illustrates graphically the survival of STAT1-deficient mice challenged with DV2 in the presence of antagonistic anti-murine DVLR1/CLEC5A mAbs or TNFR2.Fc; and FIG. 26 illustrates that DLVR1/CLEC5A is involved in JEV-mediated DAP12 phosphorylation and TNF-α secretion from human macrophages. In FIG. 26a, interaction of DVLR1/CLEC5A.Fc (1 μg) with JEV and dengue virus (DV) (5×10$^6$ PFU), respectively, were determined by ELISA. DV interacts with human DVLR1/CLEC5A (188 amino acid in length), but not the alternatively spliced form sDVLR1/CLEC5A (aa 43-65 is deleted). In contrast, JEV only interacts with sDVLR1/CLEC5A, but not full length DVLR1/CLEC5A. In FIG. 26b, dengue virus induces DAP12 phosphorylation (at 2 h p.i.) in human macrophages. DAP12 in DV-infected macrophages were precipitated by anti-DAP12 mAb, blotted to nitrocellulose paper after fractionation on SDS-PAGE, followed by incubation with antibodies against phosphotyrosine and DAP12, respectively. JEV-induced DAP12 phosphorylation (m.o.i.=5) is inhibited by pLL3.7/DVLR1/CLEC5A. In FIG. 26c, kinetics of TNF-α secretion are shown from human macrophages in response to JEV infection (left). JEV-induced TNF-α secretion is inhibited by pLL3.5/DVLR1/CLEC5A mAb (right). Data are expressed as the mean±s.d. of three independent experiments.

DETAILED DESCRIPTION

In the following detailed description of embodiments of the invention, reference is made to the accompanying drawings in which like references indicate similar elements, and in which is shown by way of illustration specific embodiments in which the invention may be practiced. These embodiments are described in sufficient detail to enable those skilled in the art to practice the invention, and it is to be understood that other embodiments may be utilized and that logical, mechanical, biological, electrical, functional, and other changes may be made without departing from the scope of the present invention. The following detailed description is, therefore, not to be taken in a limiting sense, and the scope of the present invention is defined only by the appended claims. As used in the present disclosure, the term "or" shall be understood to be defined as a logical disjunction and shall not indicate an exclusive disjunction unless expressly indicated as such or notated as "xor."

In one implementation, the disclosure provides fusion proteins comprising a carbohydrate recognition domain of an innate immunity receptor and a heterologous polypeptide. By innate immunity receptor is meant:

1) receptors encoded by genes within the leukocyte receptor complex (LRC) and LRC-related genes on human chromosome 19, including, but not limited to, the CD66 family (CEACAM1 and PSG1), the SIGLEC family, NGK7, FCGRT, the ILT/LILRA/LILRB (CD85) family, the LAIR family, the KIR (CD158) family (including the KIR2DL subfamily, KIR2DS subfamily, and KIR3DL subfamily), FCAR (CD89), NKp46 (NCR1), and GPVI (GP6); and 2) receptors encoded by genes within the natural killer receptor complex (NKC) on human chromosome 12, including but not limited to MAFA-L (KLRG1), A2M, NKR-P1A (KLRB1), LLt1 (CLEC2D), CD69 (CLEC2C), KLRF1, AICL (CLEC2B), CLEC-2 (CLECFS2), Lox-1 (OLR1), CD94 (KLRD1), NKG2-D (KLRK1), NKG2-F (KLRC4), NKG2-E (KLRC3), NKG2-C (KLRC2), NKG2-A (KLRC1), Ly49L (KLRA1) and PRB3; and 3) all human and mouse C-type lectin (CLEC) family genes, all human Sialic Acid Binding Ig-Like (SIGLEC) genes, all human Triggering Receptor Expressed on Myeloid Cells (TREM) genes, all human TREM-like (TREML/TLT) genes, all human Toll-Like Receptor (TLR) genes, and all human Fc Receptor-like (including FCRL1 through FCLR6, and also FCLRM1 and FCLRM2) genes found on human chromosomes.

Additional genes within these groupings that may be used in the methods of the disclosure may be found using the Human Genome Organization (HUGO) search engine website. See also the locus descriptions in Immunological Reviews 2001 Vol. 181: 20-38, incorporated herein by reference in its entirety.

Orthologues of any of the aforementioned genes from non-human species may be also be used in the methods of the disclosure.

C-type lectin genes that are contemplated for use in the present disclosure include, but are not limited to the following human genes: ASGR1, ASGR2 (CLEC4H2), CD207 (CLEC4K/Langerin), CD209 (DC-SIGN/CLEC4L), CD302 (CLEC13A), CLEC1A, CLEC1B (CLEC-2), CLEC2A, CLEC2B, CD69, CLEC2D, CLEC2L, CLEC3A, CLEC3B, CLEC3O, CLEC3Q, CLEC4A, CLEC4C, CLEC4D (CLEC-6), CLEC4E, CLEC4F (KCLR), CLEC4G, CLEC4M (DC-SIGNR), CD209, DVLR1/CLEC5A, CLEC6A (Dectin-2), CLEC7A (Dectin-1), CLEC9A, CLEC10A, CLEC11A, CLEC12A, CLEC14A, FCER2, KLRB1, KLRF1, LY75 (DEC205), MRC1, MRC1L1, MRC2 (Endo180), OLR1, PLA2R1, DCAL1, and COLEC10. Homologues of any of these genes are also contemplated, as are orthologues from other animal species such as mice and rats. Homologues and orthologues may be 50%, 70%, 80%, 80.6%, 83%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to any of the enumerated C-type lectin genes. A specifically contemplated orthologue is the Kupffer Cell Receptor (mKCR) gene in mice (homologous to human CLEC4F).

TREM genes and TREML genes that are contemplated for use in the present disclosure include, but are not limited to the following human genes: CD300 Antigen Like Family Member B (CD300 LB), CD300 Antigen Like Family Member G (CD300LG), TREM1, TREM2, TREML1 (TLT1), TREML2 (TLT2), TREML3 (TLT3), and TREML4 (TLT4). Homologues of any of these genes are also contemplated, as are orthologues from other animal species such as mice and rats. Homologues and orthologues may be 50%, 70%, 80%, 80.6%, 83%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to any of these enumerated genes. Specifically contemplated orthologues include mTREM1, mTREM2, mTLT1, and mTLT4 from mouse.

TLR genes that are contemplated for use in the present disclosure include, but are not limited to, the following human genes: TLR1, TLR2, TLR3, TLR4, TLR5, TLR6, TLR7, TLR8, TLR9, TLR10, TLR11, TLR12, and TLR13. Homologues of any of these genes are also contemplated, as are orthologues from other animal species such as mice and rats. Homologues and orthologues may be 50%, 70%, 80%, 80.6%, 83%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to any of the enumerated TLR genes.

SIGLEC genes that are contemplated for use in the present disclosure include, but are not limited to, the following human genes: CD22, CD33, Myelin Associated Glycoprotein (MAG), SIGLEC5, SIGLEC6, SIGLEC7, SIGLEC8, SIGLEC9, SIGLEC10, SIGLEC11, SIGLEC12, SIGLEC13, and Sialoadhesin (SN). Homologues of any of these genes are also contemplated, as are orthologues from other animal species such as mice and rats. Homologues and orthologues may be 50%, 70%, 80%, 80.6%, 83%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to any of the enumerated SIGLEC genes.

Other innate immunity receptors suitable for use in the instant disclosure include those recited in the Examples below.

The fusion protein may comprise the entire extracellular domain of the innate immunity receptor, including a carbohydrate recognition domain, or it may comprise a portion of the extracellular domain, including a carbohydrate recognition domain, or it may comprise only a carbohydrate recognition domain.

The heterologous polypeptide may comprise any polypeptide to which a carbohydrate recognition domain of an innate immunity receptor may be fused such that the heterologous polypeptide does not interfere with the binding of a carbohydrate domain to its cognate specific carbohydrate, either in vivo or in vitro. Preferably, the heterologous polypeptide is an immunoglobulin, such as human IgG1, IgG2a, IgG2b, IgG3, IgG4, IgM, IgE, IgD, IgAa, and IgA2, or an immunoglobulin from other animal species. Preferably, a fragment of an immunoglobulin is used as the heterologous polypeptide, for example an Fc fragment of an IgG. In preferred embodiments, the heterologous polypeptide is an immunoglobulin variant that does not bind to human Fc receptors. Such variants are well known in the art. For example, a human IgG1 Fc variant comprising the following mutations may be used: L234A, L235E, G237A, and P331S.

The heterologous polypeptides may further comprise one or more functional domains that permit the fusion polypeptide to be immobilized on a solid support, or purified from a complex mixture. By way of example, the heterologous polypeptide may comprise a His6 tag to permit attachment of the fusion protein to a Ni-NTA solid support according to methods well known in the art. Also by way of example, the heterologous polypeptide may comprise a glutathione-S-transferase domain so that the resulting fusion protein can be adsorbed onto, for example, glutathione beads or glutathione derivatized microtiter plates.

The heterologous polypeptide may also comprise one or more biotins, or biotin derivatives. In this way, fusion proteins may be immobilized to streptavidin-conjugated solid supports, or a streptavidin-conjugated enzyme may be bound to the fusion protein.

The fusion protein may optionally further comprise a linker between the heterologous polypeptide and a carbohydrate recognition domain of the innate immunity receptor. The linker may be a peptide linker, or it may be a non-peptidic linker, such as a polyethylene glycol.

The carbohydrate recognition domain may be C-terminal relative to the heterologous polypeptide or it may be N-terminal relative to the heterologous polypeptide in the fusion protein.

The fusion proteins of the disclosure may be prepared by any method known in the art for the production of proteins. Preferably, the fusion proteins are prepared using recombinant DNA technology and protein expression technology well known in the art. For example, DNA encoding the carbohydrate recognition domain of an innate immunity receptor may be obtained by reverse-transcriptase PCR (RT-PCR) of mRNA using primers specific for the carbohydrate recognition domain of the particular innate immunity receptor of interest. The resulting DNA may then be cloned into an expression vector in frame with DNA encoding the heterologous polypeptide sequence. Expression vectors useful in the present disclosure typically contain an origin of replication, a promoter located 5' to (i.e., upstream of) and followed by the DNA sequence coding for the fusion protein, transcription termination sequence, and the remaining vector. The expression vectors may also include other DNA sequence known in the art, for example, stability leader sequences that provide for stability of the expression product, secretory leader sequences which provide for secretion of the expression product, and sequences which allow expression of the fusion protein to be modulated or induced. The expression vector may also contain viral sequences that allow the fusion protein to be expressed using a viral expression system, such as the baculovirus expression system well known in the art. The expression vector may be introduced into host cells, such as microbial cells, yeast cells, mammalian cells, or insect cells. The expression vector may be introduced into cells as naked DNA, or it may be encapsulated within a virus (such as a baculovirus). The expression vector may be maintained within the host cell, or it may integrate into the host cell genome.

Preferably, the expression vector comprises DNA sequence that lead to the addition of a secretory leader sequence on the fusion protein, thereby causing the fusion protein to be secreted into the medium surrounding the host cells. The fusion protein can then be purified from the medium using techniques known in the art. By way of example, if the fusion protein comprises IgG as the heterologous polypeptide, then a Protein A column may be used to bind to the fusion protein to permit the fusion protein to be partitioned from other proteins in the surrounding medium.

Fusion proteins may also be produced by in vitro translation of a mRNA encoding the fusion protein using an in vitro expression system, such as a *Xenopus* oocyte expression system.

In an embodiment, the fusion proteins are produced separately and then coupled to one another using chemical techniques known in the art. For example, the carbohydrate recognition domain and the heterologous polypeptide may be produced separately and then coupled to one another using glutaraldehyde.

Following production of the fusion protein, the fusion protein may be labeled with a detectable label, such as a fluorophore, radiolabel, an enzyme, an enzyme substrate, a dye, a chemiluminescent agent, a magnetic particle, a quantum dot, or any other moiety that produces, directly or indirectly, a detectable signal. Many methods for the conjugation of such detectable labels to proteins are known in the art. By way of example only, an N-hydroxysuccinimide-activated dye, most preferably an N-hydroxysuccinimide-activated fluorophore, may be conjugated to the fusion protein by reaction with primary amines on the fusion protein.

In some embodiments, the fusion protein is biotinylated using methods known in the art such that the fusion protein comprises one or more biotins, or one or more biotin derivatives. In this way, the fusion protein may be attached to a streptavidin-detectable moiety conjugate, such as an enzyme-streptavidin conjugate.

In one series of embodiments, the fusion proteins of the disclosure are used to determine whether a specific carbohydrate component is present in a composition that comprises a polysaccharide. The methods involve contacting the polysaccharide with a fusion protein that binds to a specific carbohydrate component of a polysaccharide, and then determining whether the fusion protein has bound to polysaccharide in the composition. For example, it is known that the carbohydrate recognition domain of CLEC7A (also known as Dectin-1), can interact with β-1,3-D-glycans (see Brown, G. D. and Gordon, S., 2001, Nature 413, 36-7, incorporated herein by reference in its entirety). Binding of a fusion protein comprising the carbohydrate recognition domain of CLEC7A to a polysaccharide composition therefore indicates that the polysaccharide composition comprises β-1,3 glucan. Similarly, since the rodent Kupffer cell receptor (KCR; homologous to human CLEC4F) has high affinity to D-galactose and N-acetylgalactosamine, and is able to clear D-galactose and D-fucose terminated glycoproteins from serum (see Fadden, A. J., Holt, O. J. and Drickamer, K. (2003), Glycobiology 13, 529-37, incorporated herein by reference in its entirety), binding of a fusion protein comprising the carbohydrate recognition domain of KCR to a polysaccharide composition therefore indicates that the polysaccharide composition comprises D-galactose or N-acetylgalactosamine or D-galactose terminated glycoproteins or D-fucose terminated glycoproteins. In addition, CD209 (also known as DC-SIGN and CLEC4L) and CLEC4M (also known as DC-SIGNR and L-SIGN) can both bind to $Man_9GlcNAc_2Asn$ glycopeptide, but only CD209 and not CLEC4M can bind to glycans with a terminal fucose residue (see Guo et al (2004) Nat Struct Mol Biol 11, 591-8); therefore, fusion proteins of CD209 and CLEC4M can discriminate between polysaccharide compositions comprising these carbohydrate components. The methods and reagents of the disclosure may therefore be used to determine the identity of the carbohydrate components of a polysaccharide composition and to determine the relative amounts of those carbohydrate components e.g., to "fingerprint" a polysaccharide composition. For example, the methods and reagents of the disclosure may be used to determine the carbohydrate components of a polysaccharide composition that has immunomodulatory activity.

In addition, if one knows the identity of the cells that express the innate immunity receptors from which the carbohydrate recognition domain of the fusion protein is derived, then the assays disclosed herein reveal the identity of the cells in the body that bind to the polysaccharide under investigation. Such knowledge, for example, can help reveal the mechanism by which a particular polysaccharide composition (such as polysaccharides isolated from *Ganoderma lucidum*) exerts beneficial or deleterious effects on an organism which comes into contact with the polysaccharide. It is not necessary to know the identity of the carbohydrate component bound by the carbohydrate recognition domain in this embodiment.

The binding of the fusion proteins of the disclosure to their cognate carbohydrate component can be performed by immobilizing the composition comprising the polysaccharide to a solid support, and then contacting the solid support with a fusion protein. Binding of the fusion protein may be detected by detecting the presence of the fusion protein on the surface of the solid support, for example, by detecting the presence of the heterologous polypeptide on the surface of the solid support or by detecting the presence of the carbohydrate recognition domain on the surface of the solid support. For example, if the heterologous polypeptide is conjugated to a fluorophore, then the presence of the fluorophore, following washing, on the surface of the solid support is indicative of the presence of the fusion protein, which in turn is indicative of the presence of a polysaccharide comprising the specific carbohydrate component recognized by the carbohydrate recognition domain of the fusion protein.

As used herein, "solid support" is defined as any surface to which molecules may be attached through either covalent or non-covalent bonds. This includes, but is not limited to, membranes (for example, polyvinylidene fluoride (PVDF) membranes), plastics (for example, microtiter plates), paramagnetic beads, charged paper, nylon, Langmuir-Bodgett films, functionalized glass, germanium, silicon, PTFE, polystyrene, gallium arsenide, gold and silver. Any other material known in the art that is capable of having functional groups such as amino, carboxyl, thiol or hydroxyl incorporated on its surface, is also contemplated. This includes surfaces with any topology, including, but not limited to, spherical surfaces, grooved surfaces, and cylindrical surfaces e.g., columns.

The composition comprising a polysaccharide (also referred to herein as a "polysaccharide composition") can be, without limitation, any composition that includes a polysaccharide including, for example, a glycoprotein (including a proteoglycan), a glycolipid, peptidoglycan, a microbial cell wall, a viral particle, and a fungal cell wall. In other embodiments, the composition comprising a polysaccharide is a polysaccharide free in solution e.g., a polysaccharide that is not attached to a protein or lipid. As used herein, a "polysaccharide" means a carbohydrate molecule that comprises two or more monosaccharides.

Immobilization of the composition comprising a polysaccharide on a solid support may be achieved, for example, by biotinylating the polysaccharides in the composition, and then immobilizing on a streptavidin-conjugated solid support. In addition, polysaccharides may be immobilized on, for example, methanol-activated PVDF membranes. It is specifically contemplated that the methods of the disclosure can be performed in a "dot blot" format using dots of polysaccharide immobilized on a PVDF membrane.

In some embodiments, binding of the fusion protein to an immobilized polysaccharide is detected by binding a secondary reagent to the fusion protein, preferably to the heterologous polypeptide, and then detecting the presence of the secondary reagent. For example, a biotinylated fusion protein may be attached to a streptavidin-conjugated enzyme, and the presence of the enzyme detected by adding a substrate that yields a detectable product. A non-biotinylated fusion protein may be detected using, for example, an antibody that binds to the heterologous polypeptide (such as an anti-IgG antibody if the heterologous polypeptide is IgG, or a IgG Fc), which secondary antibody is conjugated to an enzyme. For example, if the enzyme is horseradish peroxidase (HRP), then detection of fusion protein binding may be performed using the Enhanced Chemiluminescence (ECL) technique well known in the art. The secondary reagent may also, or alternatively, be conjugated to a detectable label such as a fluorophore or a radionuclide. Many other techniques are known in the art which may be used to detect the binding of the disclosed fusion proteins to a solid support.

It is specifically contemplated that the aforementioned assays may be carried out in a multiplexed array format. For example, a solid support may be partitioned into a plurality of spatially discrete addresses onto which a plurality of different compositions may be bound. Then the solid support may be contacted with a fusion protein, and the binding of the fusion protein detected. In this way, it can be determined which, if any, of the immobilized polysaccharide compositions comprises the particular carbohydrate component bound by the carbohydrate recognition domain of the fusion protein.

In another embodiment, a single composition is immobilized on a solid support which is partitioned into a plurality of spatially discrete addresses. Each address is then contacted with a different fusion protein, each different fusion protein comprising a different carbohydrate recognition domain. Following washing to remove non-specifically bound material, binding of the fusion proteins may then be detected as described above; the spatial address of each binding reaction detected reveals the identity of the fusion protein that has bound. In this way, the composition can be probed with a number of different fusion proteins in parallel. In this embodiment, each fusion protein may comprise the same heterologous polypeptide, thereby allowing a single secondary reagent to simultaneously detect binding at each address. For example, if each fusion protein comprises IgG Fc as the heterologous polypeptide, then either an anti-IgG antibody, or Protein A, or Protein G, may be used to detect binding of the fusion protein.

The fusion proteins and methods of the disclosure may be used to "fingerprint" any composition which comprises polysaccharides, including, but not limited to, polysaccharide compositions obtained from herbal preparations, such as polysaccharide-containing fractions isolated from the fungi *Reishi* (*Ganoderma lucidim*), *Cordyceps sinensis*, and *Lentinus edodes*; and from the plant *Dendrobium huoshanense*. In particular, it is specifically contemplated that the methods used herein are used to determine the carbohydrate components of the F3 polysaccharide fraction of *Reishi* polysaccharide (see Wang, et al (2002) Bioorg Med Chem 10, 1057-62; Chen, et al (2004) Bioorg Med Chem 12, 5595-601; Chien, et al (2004) Bioorg Med Chem 12, 5603-9.; and Hsu et al (2004) J Immunol 173, 5989-99, each of which is specifically incorporated herein by reference in its entirety).

The methods provided herein can be used to "fingerprint" complex mixtures that include a number of different polysaccharide compositions, or they can be used on preparations that contain only a single polysaccharide species e.g., a single glycoprotein or a single polysaccharide.

If one knows the identity of the cells that express the innate immunity receptor from which the carbohydrate recognition domain is derived, then the aforementioned assays reveal which cells in the body bind to the polysaccharide upon introduction of the polysaccharide composition into the body. It is then possible to obtain agents that modulate the activity of the identified innate immunity receptor. For example, agents that mimic the structure of the polysaccharide or that potentiate the interaction of the polysaccharide with the innate immunity receptor may be generated if interaction of the innate immunity receptor with the polysaccharide leads to beneficial effects in the body. See the section below entitled "Modulators."

In another series of embodiments, the methods and fusion proteins of the disclosure are used to determine the identity of polysaccharides displayed on the surface of a pathogen, such as a fungal cell, a bacterial cell, or a virus, such as an enveloped virus, and also including but not limited to viruses from the Flaviviridae family. Flaviviridae viruses suitable for use in the methods disclosed herein include, but are not limited to, members of the genus Flavivirus (such as, for example, Dengue virus (DV), West Nile Virus (WNV), Japanese enchephamyelitis virus (JEV), yellow fever virus (YFV), and tick-borne encephamyelitis virus) and members of the genus Hepacivirus (such as, for example, Hepatitis C virus). In one such embodiment, a fusion protein is immobilized on a solid support (for example, using a Protein A derivatized solid support if the heterologous polypeptide is IgG or a fragment thereof), and the solid support is this contacted with a composition comprising the pathogen of interest. Following washing, the binding of the pathogen is then detected using, for example, a secondary reagent that binds specifically to the pathogen in a manner that does not compete with the binding of the fusion protein. For example, a secondary antibody that is specific for the pathogen may be used. Binding of the secondary reagent is then detected as described above (for example using HRP-conjugated secondary antibody), or it may be detected using a tertiary reagent that binds to the secondary reagent (for example, using an anti-IgG antibody conjugated to HRP if the secondary reagent is an anti-pathogen IgG). If binding of the secondary reagent is detected, then this reveals that the pathogen comprises a polysaccharide that comprises the specific carbohydrate component recognized by the carbohydrate recognition domain of the fusion protein.

Alternatively, the assay may be performed by immobilizing a reagent that binds specifically to the pathogen on a solid support. For example, an antibody which binds to the pathogen can be immobilized on a solid support, then contacted with a composition comprising the pathogen. The solid support is then contacted with the fusion protein(s), and the binding of the fusion proteins is then detected as described above (preferably, the fusion protein does not compete for pathogen binding with the immobilized reagent). For example, if the heterologous polypeptide of the fusion protein is IgG Fc, then an anti-IgG antibody can detect binding of the fusion protein to the pathogen; alternatively, if the fusion protein is conjugated to a detectable label, then detection of the label is used to detect binding.

It is expressly contemplated that the aforementioned pathogen assays can be carried out in a multiplexed format using, for example, a plurality of different fusion proteins simultaneously. For example, an antibody that binds to the pathogen may be immobilized at a plurality of discrete addresses on a solid support; then the solid support is contacted with a composition comprising the pathogen; and then each specific address is contacted with a different fusion protein, each different fusion protein comprising a different carbohydrate recognition domain. If each fusion protein comprises the same heterologous polypeptide, then binding of the fusion protein may be detected using a single reagent that binds to the heterologous polypeptide. For example, if the heterologous polypeptide is IgG Fc, then an anti-IgG antibody can be used to detect binding of the fusion protein(s). The spatial address of each binding reaction then reveals the identity of the fusion protein. Alternatively, a multiplexed assay may be carried out using a plurality of different fusion proteins immobilized on the solid support at spatially discrete addresses, by contacting the solid support with the composition comprising the pathogen, followed by contacting the solid support with a secondary reagent that binds specifically to the pathogen. For example, if the pathogen is Dengue virus, then the secondary reagent may be an antibody against the E envelope protein. As in all the preceding assays, washing may be used to remove non-specifically bound material from the solid support.

Using the methods disclosed herein, it has been discovered that Dengue virus binds to DVLR1/CLEC5A on the surface of CD14+ macrophages. See Example 11. It has further been shown that DVLR1/CLEC5A binding to Dengue virus results in the activation of DAP12, which in turn leads to the release of the proinflammatory cytokines TNF-α, MIP-1α, IFN-α, and IL-8 from macrophages. See Example 12. The release of these cytokines is implicated in the development of Dengue hemorrhagic fever (DHF) and Dengue shock syndrome (DSS).

According to embodiments the methods disclosed herein, it has been shown specifically that DLVR1/CLEC5A interacts with the dengue virus. See Example 16-18. Moreover, it is shown that DLVR1/CLEC5A modulates DAP12 phosphorylation, which is believed to modulate, at least in part, release of pro-inflammatory cytokines such as TNF-α. See Example 18. When DLVR1/CLEC5A expression is knocked down in dengue virus infected cells, phosphorylation of DAP12 is reduced and pro-inflammatory cytokine secretion, including TNF-α, is reduced without affecting secretion of viral clearance cytokines such as interferon-α. See Examples 18-19. According to embodiments, knock down of DLVR1/CLEC5A may be accomplished using convention RNA-interference techniques, including use of both si-RNA and sh-RNA. See Example 18-19.

Knowledge of the identity of the innate immunity receptor(s) that interact with a pathogen may then be used to develop agents that modulate the activity of the innate immunity receptor. For example, modulators that activate an identified innate immunity receptors may be obtained in order to augment the immune response to a particular pathogen. In cases where interaction of an innate immunity receptor to a particular polysaccharide composition is detrimental to the body (for example, when a pathogen causes excessive inflammation), modulators may be obtained that reduce the activity of the innate immunity receptors. For example, agents (such as antibodies) that block the binding of a pathogen to an innate immunity receptor may be used to prevent the occurrence of an undesirable proinflammatory reaction to infection with said pathogen. Similarly, if the screening methods disclosed herein reveal that a particular pathogen (such as a virus) uses an innate immunity receptor to gain entry into a cell, then an agent that blocks the binding of the pathogen to the innate immunity receptor will prevent entry of the pathogen into the cell.

According to embodiments of the methods disclosed herein, administration of interruption agents that reduce available DLVR1/CLEC5A binding sites is shown to increase survival rates of dengue virus infected mice. According to embodiments, administration of DLVR1/CLEC5A antibodies that interfere with binding of DVLR1/CLEC5A to DVLR1/CLEC5A ligands was shown to increase mouse survival rates. See Example 25.

In another series of embodiments, the fusion proteins of the disclosure are used to disrupt or prevent the interaction between a polysaccharide and an innate immunity receptor on a cell surface. In this series of embodiments, the fusion protein comprises the carbohydrate recognition domain of the innate immunity receptor that is expressed on the cell surface. The cell expressing the innate immunity receptor is then contacted with the fusion protein, either in vivo or in vitro, whereby the fusion protein competes with the polysaccharide for binding to the innate immunity receptor.

If interaction of the polysaccharide with the innate immunity receptor on the cell surface leads to deleterious effects in an organism, then a therapeutically effective amount of the fusion protein may be administered to the organism in a pharmaceutical composition to prevent or diminish the interaction. Preferably, the heterologous polypeptide of the administered fusion protein does not bind to any cell surface receptor. For example, the heterologous polypeptide may be comprised of a mutated variant of IgG Fc that does not bind to Fc receptors on cell surfaces.

Purification

In another series of embodiments, the fusion proteins are used to at least partially purify or isolate polysaccharides that comprise the specific carbohydrate component recognized by the carbohydrate recognition domain of the fusion protein. For example, the fusion protein may be immobilized on a solid support, and a composition suspected of containing, or known to contain, a polysaccharide composition is contacted with the solid support. If the composition comprises a polysaccharide that can bind to the carbohydrate recognition domain of the fusion protein, then that polysaccharide will bind to the fusion protein. The solid support can then be washed to remove non-specifically bound components of the composition, and the bound polysaccharide may then be eluted by dissociating the interaction with the fusion protein, and collected. For example, if the fusion protein comprises the carbohydrate recognition domain of a lectin receptor, then the interaction may be dissociated using EDTA to chelate $Ca^{2+}$. In this way, it is possible to purify specific polysaccharide compositions from complex mixtures. In preferred embodiments, this method is used to purify polysaccharides isolated from *Ganoderma lucidum* (Reishi).

For the aforementioned purification method, the solid support may comprise, for example, a column to which the fusion protein is bound. Suitable columns include Sepharose Protein A columns, to which fusion proteins comprising IgG as the heterologous polypeptide may be bound via interaction with of the IgG domain of the fusion protein with Protein A. Alternatively, CNBr activated column media may be bound to fusion proteins.

The present disclosure also provides kits that can be used in any of the above methods. In one embodiment, a kit comprises a fusion protein according to the disclosure, in one or more containers. The kit may also comprise a secondary reagent, such as an antibody that specifically binds to the heterologous polypeptide domain of the fusion protein e.g., an anti-IgG antibody if the heterologous polypeptide is IgG, or a fragment thereof. The kit may also comprise reagents and buffers for detecting the binding of a fusion protein to a polysaccharide. For example, in embodiments where a HRP-conjugated secondary antibody is used to detect the binding of a fusion protein to a polysaccharide, the kit may comprise the reagents necessary to establish an enhanced chemiluminescence reaction e.g., one or more containers comprising luminol, p-coumaric acid, Tris buffer, and hydrogen peroxide. The kit may also comprise one or more positive control polysaccharides. The kit may also comprise one or more solid supports for use in the aforementioned methods, for example, one or more PVDF membranes or one or more multiwell microtiter plates.

Modulators

As described above, the methods of the disclosure identify innate immunity receptor(s) that interact with a particular polysaccharide. This information then allows one to obtain modulators of the identified innate immunity receptor. A modulator can be an agonist, an antagonist (including competitive and non-competitive antagonists), or an inverse agonist of an innate immunity receptor. A modulator may, without limitation: inhibit the binding of a polysaccharide to an innate immunity receptor; potentiate the binding of a polysaccharide to an innate immunity receptor; or function as a mimetic of a polysaccharide that binds to an innate immunity receptor, thereby activating the innate immunity receptor even in the absence of the polysaccharide.

Modulators of innate immunity receptors include antibodies. For example, an antagonistic antibody against an innate immunity receptor can prevent binding of a pathogen to the innate immunity receptor. In some cases, such an antibody is a neutralizing antibody as it prevents the entry of the pathogen into the cell that expresses the innate immunity receptor. Alternatively, an agonistic antibody may function as a mimetic of a polysaccharide composition that exerts a beneficial effect on a cell. An antagonistic antibody may also bind to an innate immunity receptor in such a way as to block the downstream signaling by the receptor upon pathogen binding. Antibodies may be, without limitation, polyclonal, monoclonal, monovalent, bispecific, heteroconjugate, multispecific, human, humanized or chimeric antibodies, single chain antibodies, Fab fragments, F(ab') fragments, fragments produced by a Fab expression library, anti-idiotypic (anti-Id) antibodies, and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (Mab) is meant to include intact molecules, as well as, antibody fragments (such as, for example, Fab and F(ab')2 fragments) which are capable of specifically binding to protein. Fab and F(ab')2 fragments lack the Fc fragment of intact antibody, clear more rapidly from the circulation of the animal or plant, and may have less non-specific tissue binding than an intact antibody (Wahl et al., J. Nucl. Med. 24: 316-325 (1983)). Methods for producing antibody agonists are described in, for example, PCT publication WO 96/40281; U.S. Pat. No. 5,811,097; Deng et al., Blood 92 (6): 1981-1988 (1998); Chen et al., Cancer Res. 58 (16): 3668-3678 (1998); Harrop et al., J. Immunol. 161 (4): 1786-1794 (1998); Zhu et al., Cancer Res. 58 (15): 3209-3214 (1998); Yoon et al., J. Immunol. 160 (7): 3170-3179 (1998); Prat et al., J. Cell. Sci. 111 (Pt2): 237-247 (1998); Pitard et al., J. Immunol. Methods 205 (2): 177-190 (1997); Liautard et al., Cytokine 9 (4): 233-241 (1997); Carlson et al., J. Biol. Chem. 272 (17): 11295-11301 (1997); Taryman et al., Neuron 14 (4): 755-762 (1995); Muller et al., Structure 6 (9): 1153-1167 (1998); Bartunek et al., Cytokine 8 (1): 14-20 (1996); Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (which are all incorporated by reference herein in their entireties).

The disclosure provides non-limiting specific examples of anti-DVLR1/CLEC5A monoclonal antibodies that prevent TNF-α release from macrophages following DV infection. See Example 15. These antibodies can be used in the pharmaceutical compositions and the methods of treatment specified herein, particularly in compositions and methods for the treatment or prophylaxis of DV infection in humans.

The present disclosure also provides humanized anti-DVLR1/CLEC5A antibodies that prevent TNF-α release from macrophages following DV or JEV infection. See Examples 20-26. In specific embodiments, the humanized antibody is selected from the group consisting of humanized antibodies 9B12, 3E12A2, 3E12C1, 3E12G9, and 8H8F5. These antibodies can be used in the pharmaceutical compositions and the methods of treatment specified herein, particularly in compositions and methods for the treatment or prophylaxis of DV infection in humans. Specific treatments include inhibiting DV-induced plasma leakage, as well as subcutaneous and vital organ hemorrhaging. The humanized antibodies can be used as methods of treatment for DV-induced hemorrhagic shock and sepsis. It is expressly contemplated that the principles set forth herein with respect to the mitigation to cytokine stimulation by virus is applicable to all viruses that bind to and modulate stimulating receptors of cells.

Moreover, the principles of discovery and treatment of viruses can be similarly extended to cell entry receptors, as well as the action of bacterial, fungus, and parasites. The methods of the present disclosure will enable persons of ordinary skill in the art to determine the binding profiles of pathogens (i.e., which receptors they bind to), determine the effect that binding the receptor has, and provide interruption agents, such as antibodies, to interfere with the pathogens ability to bind to the target receptor.

According to embodiments, the monoclonal antibodies (mAbs) generated by fusion of murine splenocytes and NS1 myeloid partner cells, anti-DVLR1/CLEC5A mAb can be generated by phage display technology to generate single chain human anti-human DLVR1/CLEC5A mAbs. The agonistic and antagonistic mAbs can be selected based on the screening method disclosed in Examples 19-25.

To decrease antigenicity of current murine anti-human DLVR1/CLEC5A mAb, the wild type Fc portion is replaced with human immunoglobulin G1 (IgG1), according to embodiments. To further abolish Fc binding to Fc receptor and prevent complement activation, the mutated Fc fragment of human IgG1 (L234A, L235E, G237A, and P331S) may be used to replace the wild-type Fc to generate the humanized mAbs. To further decrease the antigenecity, the framework region of antibody V domain may be replaced with a human sequence.

Modulators of innate immunity receptors also include small molecules identified by high throughput screening methods. Such high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that bind to the innate immunity receptor of interest. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g., U.S. Pat. No. 5,010,175; Furka, 1991, Int. J. Pept. Prot. Res., 37: 487-493; and Houghton et al., 1991, Nature, 354: 84-88). Other chemistries for generating chemical diversity libraries can also be used. Nonlimiting examples of chemical diversity library chemistries include, peptides (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, Proc. Natl. Acad. Sci. USA, 90: 6909-6913), vinylogous polypeptides (Hagihara et al., 1992, J. Amer. Chem. Soc., 114: 6568), nonpeptidal peptidomimetics with glucose scaffolding (Hirschmann et al., 1992, J. Amer. Chem. Soc., 114: 9217-9218), analogous organic synthesis of small compound libraries (Chen et al., 1994, J. Amer. Chem. Soc., 116: 2661), oligocarbamates (Cho et al., 1993, Science, 26i: 1303), or peptidyl phosphonates (Campbell et al., 1994, J. Org. Chem., 59: 658), nucleic acid libraries (for example, see U.S. Pat. No. 5,270, 163 describing the generation of nucleic acid ligands, also known as "aptamers"), peptide nucleic acid libraries (U.S. Pat. No. 5,539,083), antibody libraries (e.g., Vaughn et al., 1996, Nature Biotechnology, 14 (3): 309-314) and PCT/US96/10287), carbohydrate libraries (e.g., Liang et al., 1996, Science, 274-1520-1522) and U.S. Pat. No. 5,593,853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

Pharmaceutical Compositions

The instant disclosure also provides pharmaceutical compositions. In some embodiments, the pharmaceutical compositions comprise the fusion proteins of the disclosure. In other embodiments, the pharmaceutical compositions comprise a modulator of an innate immunity receptor (for example antibodies against an innate immunity receptor such as DVLR1/CLEC5A, including the antibodies exemplified in Example 15). In such pharmaceutical compositions, the fusion protein or the innate immunity receptor modulator form the "active compound." In some embodiment, the pharmaceutical compositions are administered to a subject in order to treat or prevent diseases or disorders characterized by the binding of a polysaccharide to an innate immunity receptor on the surface of a cell in that subject. In other embodiments, the pharmaceutical compositions are administered to a subject to activate an innate immunity receptor in circumstances where increasing the activity of that receptor is beneficial to the subject. In still other embodiments, the pharmaceutical compositions are administered to a subject to potentiate the binding of a polysaccharide composition to an innate immunity receptor.

In addition to active compound, the pharmaceutical compositions preferably comprise at least one pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Subject as used herein refers to humans and non-human primates (e.g., guerilla, macaque, marmoset), livestock animals (e.g., sheep, cow, horse, donkey, pig), companion animals (e.g., dog, cat), laboratory test animals (e.g., mouse, rabbit, rat, guinea pig, hamster), captive wild animals (e.g., fox, deer) and any other organisms who can benefit from the agents of the present disclosure. There is no limitation on the type of animal that could benefit from the presently described agents. The most preferred subject of the present disclosure is a human. A subject regardless of whether it is a human or non-human organism may be referred to as a patient, individual, animal, host, or recipient.

Pharmaceutical compositions suitable for injectable use include sterile aqueous solutions (where water-soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions, are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to cell-specific antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in subjects. The dosage of such compounds lies preferably within a range of circulating concentrations that include the ED50 with little or no toxicity. The dosage can vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in subjects. Levels in plasma can be measured, for example, by high performance liquid chromatography.

As defined herein, a therapeutically effective amount of an active compound of the disclosure may range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. Without limitation, the active compound can be administered between one time per week and three or more times per day, for between about 1 to 10 weeks, preferably between 2 to 8 weeks, more preferably between about 3 to 7 weeks, and even more preferably for about 4, 5, or 6 weeks. The skilled artisan will appreciate that certain factors can influence the dosage and timing required to effectively treat a subject, including but not limited to the severity of the disease or disorder, previous treatments, the general health or age of the subject, and other diseases present. Moreover, treatment of a subject with a therapeutically effective amount of a pharmaceutical composition of the disclosure can include a single treatment or, preferably, can include a series of treatments.

Gene Therapy and RNAi

Constructs encoding the fusion proteins of the disclosure can be used as a part of a gene therapy protocol to deliver therapeutically effective doses of a receptor fusion protein to a subject. A preferred approach for in vivo introduction of nucleic acid into a cell is by use of a viral vector containing nucleic acid, encoding a fusion protein of the disclosure. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous nucleic acid molecules encoding fusion proteins in vivo. These vectors provide efficient delivery of nucleic acids into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) Blood 76:27 1). A replication defective retrovirus can be packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al., (eds.) Greene Publishing Associates, (1989), Sections 9.10-9.14 and other standard laboratory manuals.

Another useful viral gene delivery system uses adenovirus-derived vectors. The genome of an adenovirus can be manipulated such that it encodes and expresses a gene product of interest but is inactivated in terms of its ability to replicate in a normal lytic viral life cycle. See, for example, Berkner et al., BioTechniques 6:616 (1988); Rosenfeld et al., Science 252: 431-434 (1991); and Rosenfeld et al., Cell 68:143-155 (1992). Suitable adenoviral vectors derived from the adenovirus strain Ad type 5 d1324 or other strains of adenovirus (e.g., Ad2, Ad3, Ad7 etc.) are known to those skilled in the art. Recombinant adenoviruses can be advantageous in certain circumstances in that they are not capable of infecting non-dividing cells and can be used to infect a wide variety of cell types, including epithelial cells (Rosenfeld et al., (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated, into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., cited supra; Haj-Ahmand et al., J. Virol. 57:267 (1986)).

In another embodiment, non-viral gene delivery systems of the present disclosure rely on endocytic pathways for the uptake of the subject nucleotide molecule by the targeted cell. Exemplary gene delivery systems of this type include liposomal derived systems, poly-lysine conjugates, and artificial viral envelopes. In a representative embodiment, a nucleic acid molecule encoding a fusion protein of the disclosure can be entrapped in liposomes bearing positive charges on their surface (e.g., lipofectins) and (optionally) which are tagged with antibodies against cell surface antigens of the target tissue (Mizuno et al. (1992) No Shinkei Geka 20:547-551; PCT publication WO91%6309; Japanese patent application 1047381; and European patent publication EP-A43075).

Gene delivery systems for a gene encoding a fusion protein of the disclosure can be introduced into a subject by any of a number of methods. For instance, a pharmaceutical preparation of the gene delivery system can be introduced systemically, e.g., by intravenous injection, and specific transduction of the protein in the target cellsoCcurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g., Chen et al. (1994) PNAS 91: 3 054-3057). The pharmaceutical preparation of the gene therapy construct can consist essentially of the gene delivery system in an acceptable diluent, or can comprise a slow release matrix in which the gene delivery vehicle is imbedded. Where the fusion protein can be produced intact from recombinant cells, e.g., retroviral vectors, the pharmaceutical preparation can comprise one or more cells which produce the fusion protein.

In another embodiment, the expression of an innate immunity receptor that is identified according to the methods disclosed herein as being involved in the pathogenesis is reduced or completely inhibited using RNA interference (RNAi). RNAi is well known in the art and may be accomplished using small interfering RNA (siRNA). siRNAs according to the invention could have up to 29 bps, 25 bps, 22 bps, 21 bps, 20 bps, 15 bps, 10 bps, 5 bps or any integer thereabout or therebetween. Such siRNAs can be administered, e.g., in a form encoded by a vector (for example, a vector encoding a small hairpin RNA (shRNA)) or as a liposome nucleic acid complex. The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787). Accordingly, the present disclosure also provides pharmaceutical compositions comprising RNA molecules that are capable of mediating RNA interference of an innate immunity receptor when administered to a subject.

According to embodiments, the present disclosure provides a non-limiting example of the RNAi-mediated "knock down" of the DVLR1/CLEC5A gene in macrophages. The attenuation of DVLR1/CLEC5A in this manner significantly reduces the secretion of proinflammatory cytokines in DV-infected macrophages, thereby indicating that RNAi-mediated attenuation of DVLR1/CLEC5A will be useful for the treatment of DV.

It is specifically contemplated that siRNA or shRNA that attenuates expression of DVLR1/CLEC5A is used for the RNAi-mediated treatment of subjects infected with Dengue virus. Methods for designing, synthesizing, and administering shRNA and siRNA in order to attenuate the expression of a specific gene are well known in the art and are described in, for example, U.S. Pat. No. 7,022,828. Non-limiting examples of agents suitable for formulation with the shRNA constructs and siRNA molecules of the disclosure include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues, for example the CNS (Jolliet-Riant and Tillement, 1999, Fundam. Clin. Pharmacol., 13, 16 26); biodegradable polymers, such as poly(DL-lactide-coglycolide) microspheres for sustained release delivery after implantation (Emerich, D F et al, 1999, Cell Transplant, 8, 47 58) Alkermes, Inc. Cambridge, Mass.; and loaded nanoparticles, such as those made of polybutylcyanoacrylate, which can deliver drugs across the blood brain barrier and can alter neuronal uptake mechanisms (Prog Neuropsychopharmacol Biol Psychiatry, 23, 941949, 1999). Other non-limiting examples of delivery strategies, including CNS delivery of the nucleic acid molecules of the instant disclosure include material described in Boado et al., 1998, J.

Pharm. Sci., 87, 1308 1315; Tyler et al, 1999, FEBS Lett., 421, 280 284; Pardridge et al., 1995, PNAS USA., 92, 5592 5596; Boado, 1995, Adv. Drug Delivery Rev., 15, 73 107; Aldrian-Herrada et al., 1998, Nucleic Acids Res., 26, 4910 4916; and Tyler et al., 1999, PNAS USA., 96, 7053 7058. All these references are hereby incorporated herein by reference. In addition, compositions comprising surface-modified liposomes containing poly(ethylene glycol) lipids (PEG-modified, or long-circulating liposomes or stealth liposomes) may also be used with the nucleic acids of the disclosure. Nucleic acid molecules of the disclosure can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601 2627; Ishiwata et al., Chem. Pharm, Bull. 1995, 43, 1005 1011). Such liposomes have been shown to accumulate selectively in tumors, presumably by extravasation and capture in the neovascularized target tissues (Lasic et al., Science 1995, 267, 1275 1276; Oku et al., 1995, Biochim. Biophys. Acta, 1238, 86 90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864 24870; Choi et al., International PCT Publication No. WO 96/10391; Ansell et al., International PCT Publication No. WO 96/10390; Holland et al., International PCT Publication No. WO 96/10392; all of which are incorporated by reference herein). Long-circulating liposomes are also likely to protect drugs from nuclease degradation to a greater extent compared to cationic liposomes, based on their ability to avoid accumulation in metabolically aggressive MPS tissues such as the liver and spleen.

EXAMPLES

The present disclosure is further described by the following non-limiting examples:

Example 1

Preparation of Innate Immunity Receptor:Fc Fusion Protein

Cell Culture 293F cells (Invitrogen; R790-07) were cultured in serum-free 293 FREESTYLE 203 expression medium (Invitrogen, 12338-018) in a 125 mL flask on an orbital shaker (125 rpm) at 37° C. in a $CO_2$ incubator.

Construction of Receptor.Fc Fusion Genes

The extracellular domains of lectin receptors, TREMs and TLTs were cloned by the reverse-transcriptase polymerase chain reaction (RT-PCR), followed by subcloning into a yT&A vector and then into a pcDNA3.1(+)hIgG1.Fc expression vector. The resulting receptor.Fc construct encodes recombinant proteins that are fused with a mutated human IgG1 Fc portion, which does not bind to human Fc receptors. The mutations in the IgG1 Fc portion are L234A, L235E, G237A, and P331S. The sequences of the primers used to RT-PCR amplify the extracellular domains are (alternatively primers can be selected from the sequences listed in Table 2):

$CLEC_1A/CLEC_1$
sense primer
SEQ ID NO: 1
5'-GAATCCTTTCAGTACTACCAGCTCTCC-3' antisense primer
SEQ ID NO: 2
5'-GAATTCTCAGTCACCTTCGCCTAATGT-3'

$CLEC_1B/CLEC_2$
sense primer
SEQ ID NO: 3
5'-GGATCCCTGGGGATITGGTCTGTC-3' antisense primer
SEQ ID NO: 4
5'-GAATTCTTAAGGTAGITGGTCCAC-3'

$CLEC_2B/AICL$
sense primer
SEQ ID NO: 5
5'-GGATCCTCTCAGAGTTTATGCCCC-3' antisense primer
SEQ ID NO: 6
5'-GGATCCCCCCATTATCTTAGACAT-3'

$CLEC_4A/DCIR$
sense primer
SEQ ID NO: 7
5'-GGATCCTTTCAAAAATATTCTCAGCTTCTT-3' antisense primer
SEQ ID NO: 8
5'-GAATTCTCATAAGTGGATCTTCATCATC-3'

$CLEC_4C/BDCA_2$
sense primer
SEQ ID NO: 9
5'-GGATCCTTTATGTATAGCAAAACTGTCAAG-3' antisense primer
SEQ ID NO: 10
5'-GAATTCTTATATGTAGATCTTCTTCATCTT-3'

$CLEC_4D/CLEC_6$
sense primer
SEQ ID NO: 11
5'-GAATCCCATCACAACTTTTCACGCTGT-3' antisense primer
SEQ ID NO: 12
5'-GAATTCCTAGTTCAATGTTGTTCCAGG-3'

$CLEC_4E/MINCLE$
sense primer
SEQ ID NO: 13
5'-GAAGATCTACATTTCGCATCTTTCAAACC-3' antisense primer
SEQ ID NO: 14
5'-GCGGTTAAAGAGATTTTCCTTTGTTCA-3'

$CLEC_4K/Langerin$
sense primer
SEQ ID NO: 15
5'-GGATCCCGGTTTATGGGCACCATA-3' antisense primer
SEQ ID NO: 16
5'-GGATCCTCACGGTTCTGATGGGAC-3'

$CLEC_4L/DC-SIGN$
sense primer
SEQ ID NO: 17
5'-GGATCCAAGGTCCCCAGCTCCATAAG-3'

-continued

```
antisense primer
                                              SEQ ID NO: 18
5'-GAATTCCTACGCAGGAGGGGGGT-3'

CLEC4M/DC-SIGNR/L-SIGN
sense primer
                                              SEQ ID NO: 19
5'-GGATCCTCCAAGGTCCCCAGCTCC-3' antisense primer
                                              SEQ ID NO: 20
5'-GAATTCCTATTCGTCTCTGAAGCAGG-3'

DLVR1/CLEC5A (MDL-1)
sense primer
                                              SEQ ID NO: 21
5'-AGATCTAGTAACGATGGTTTCACCAC-3' antisense primer
                                              SEQ ID NO: 22
5'-GAATTCCTGTGATCATTTGGCATTCTT -3'

CLEC6A/Dectin-2
sense primer
                                              SEQ ID NO: 23
5'-GGATCCACATATGGTGAAACTGGC-3' antisense primer
                                              SEQ ID NO: 24
5'-GAATTCCATCAGTCGATGGGC-3'

CLEC7A/Dectin-1
sense primer
                                              SEQ ID NO: 25
5'-GGATCCACCATGGCTATTTGGAGATCC-3' antisense primer
                                              SEQ ID NO: 26
5'-GAATTCTTACATTGAAAACTTCTTCTCACA-3'

CLEC10A/ML2
sense primer
                                              SEQ ID NO: 27
5'-GGATCCTCCAAATTTCAGAGGGACCTG-3' antisense primer
                                              SEQ ID NO: 28
5'-GAATTCTCAGTGACTCTCCTGGCTG-3'

CLEC12A/CLL-1
sense primer
                                              SEQ ID NO: 29
5'-GGATCCGTAACTTTGAAGATAGAAATGAAA-3' antisense primer
                                              SEQ ID NO: 30
5'-GAATCCTCATGCCTCCCTAAAATATGTA-3'

CLEC13A/BIMLEC
sense primer
                                              SEQ ID NO: 31
5'-GGATCCTCATGCTCCGGGCCGCG -3' antisense primer
                                              SEQ ID NO: 32
5'-GAATTCGCTAGCAATCACCAATGCTGA-3'

COLEC12/CL-P1
sense primer
                                              SEQ ID NO: 33
5'-AGAGGTGACAGAGGATCCCA-3' antisense primer
                                              SEQ ID NO: 34
5'-GAATTCGTGATCCCATCACAGTCC-3'

MAFA-L/KLRG-1
sense primer
                                              SEQ ID NO: 35
5'-GGATCCTGCCAGGGCTCCAACT-3' antisense primer
                                              SEQ ID NO: 36
5'-ATGACAGATCTGAGGGTCA-3'
```

Expression and Purification of Recombinant Receptor.Fc Fusion Proteins

The receptor.Fc proteins were over-expressed using the FREESTYLE 293 Expression System (Invitrogen, Carlsbad, Calif.) and purified on protein A columns. Briefly, $3 \times 10^7$ 293-F cells were spun down at 1,500 rpm, then resuspended in 28 ml FREESTYLE 293 expression medium. Then, 40 μL of 293FECTIN was mixed with 1 ml OPTI-MEM (Invitrogen, 31985-062) for 5 min at room temperature, then incubated with 30 μg plasmid DNA in 1 ml OPTI-MEM (Invitrogen, 31985-062) for another 20 min, before addition to the 293-F cells. After 48 h, the supernatant was harvested and the recombinant fusion proteins were purified by protein A columns.

Example 2

Preparation of Polysaccharide Extracts Crude Extracts of *Reishi*

Crude *Reishi* extract (prepared via alkaline extraction, neutralization and ethanol precipitation) was obtained from Pharmanex Co. (CA, USA). Spectrapor® dialysis membrane tubing with molecular weight cut off (MWCO) 6000-8000 dalton, Thermo bio-basic SEC-1000 columns, Tosoh TSK G5000PW×1 SEC columns, and all chemicals and reagents were from Sigma, or Aldrich Co., unless indicated.

Purification of *Reishi* Extract

Crude *Reishi* powder (6 g) (obtained from Pharmanex Co.) was dissolved in 120 mL of ddH$_2$O, stirred at boiling water (100° C.) for 2 h, and centrifuged (1000 rpm) for 1 h to remove insoluble material. The resulting solution was concentrated at between about 40° C. and about 50° C. to give a small volume, and then lyophilized to generate 5 g (83%) powder of dark-brown color (*G. lucidum* polysaccharides; GLPS). This water soluble residue was stored at −20° C. until further purification.

Standardization-Isolation of the F3 Fraction of *Reishi* Polysaccharide

*G. lucidum* polysaccharide fraction 3 (hereinafter referred to as "GLPS F3" and "F3") was isolated from the dark powder of water soluble residue of *Reishi* polysaccharide. All chromatography steps were performed at 4° C. in a cold room. The sample (2.1 g) was dissolved in a small volume of Tris buffer (pH 7.0, 0.1 N) containing 0.1 N sodium azide, and purified by gel filtration chromatography using a Sephacryl S-500 column (95×2.6 cm) with 0.1 N Tris buffer (pH 7.0) as the eluent. The flow rate was set at 0.6 mL/min, and 6.0 mL per tube was collected. After chromatography, each fraction was subjected to the phenol-H$_2$SO$_4$ method to detect the content of sugar in each tube. Five fractions were collected (fraction 1-5). Fraction 3 (F3) was concentrated at about 40~50° C. in a rotary vaporizer to give a small volume which was then dialyzed using a 6000-8000 dalton MWCO membrane to remove excessive salt and sodium azide. Following dialysis, F3 was then lyophilized to give 520 mg of solid.

Preparation of Polysaccharides from *Cordyceps Sinensis*

To purify the polysaccharides from *Cordyceps sinensis*, samples were chopped into 0.2 cm$^3$ pieces then incubated in deionized boiling water (100° C.) for 60 min, then cooled down to room temperature before passing through the 0.2 μm filter, followed by addition of an equal volume of ethanol to precipitate the polysaccharides. The precipitates were dried using a lyophilizer and stored at 4° C. Total sugar analysis of the polysaccharides was determined by the Phenol-$H_2SO_4$ method, by measuring OD at 485 nm, while the purity of the polysaccharides was determined by HPLC using a Thermo Bio-Basic SEC-1000 column with UV detection at 280 nm and using a RI detector.

Preparation of Polysaccharides from *Dendrobium huoshanense*

Air-dried *D. huoshanense* was crushed and ground to a powder, homogenized in distilled water, and stirred at 40° C. overnight. The insoluble material was collected by centrifugation. The supernatant was concentrated to a small volume, and then added to 1 volume of ethanol to yield a precipitate (O) and supernatant (N). A TSK G-5000 PW size exclusion column was used in high performance liquid chromatography (HPLC) for polysaccharides analysis with standard pullulan fractions having defined molecular weights. The molecular weight of polysaccharides in N was estimated as between $1.2 \times 10^5$-$4.1 \times 10^5$ daltons, and the molecular weight of polysaccharides in O was estimated as between $1.0 \times 10^6$-$2.2 \times 10^5$ daltons. The total carbohydrate content was measured by the phenol-sulfuric acid method. Polysaccharides in O were 83%, and polysaccharides in N were 77%. Both O and N test positive with an iodine reaction ($\lambda$max 440 nm, deep blue color) suggesting that the polysaccharides in these fractions are primarily $\alpha$-D-glucan.

Preparation of Polysaccharides from Mushroom

Air-dried *Lentinus edodes* was crushed and ground to a powder, homogenized in distilled water, and stirred at 4° C. overnight. Residues were removed by centrifugation and supernatant was concentrated to a small volume, then lyophilized to give crude polysaccharide L. Then, 0.25N NaOH solution was added to the water insoluble residue (which was isolated by centrifugation), and the mixture was then stirred at room temperature overnight before adding 2 volume of ethanol to precipitate the polysaccharides. Distilled water was then added to the precipitated polysaccharide, followed by acetic acid to neutralize pH. The resulting solution was centrifuged and lyophilized to give polysaccharide M. HPLC using a TSK G-500 PW size exclusion column was then performed in order to analyze the polysaccharides. The total carbohydrates content was measured by the phenol-sulfuric acid method with L comprising 79% carbohydrates, and M comprising 90% carbohydrates. A comparison with data of the fractions of polysaccharides from *Lentinus edodes* suggested that the polysaccharides L and M are primarily $\beta$-1,3-D-glucan.

Preparation of $\beta$-1,3-glucan, D-glucose and D-galactose

To prepare samples for a competition assay, 100 mg of $\beta$-1,3-glucan (Fluka, Japan) was suspended in 7.5 ml of water, and 50 L of a 40% (w/w) aqueous solution of sodium hydroxide was added. The mixture was heated under reflux for 1.5 hours, and cooled. Then, methanol was added to precipitate $\beta$-1,3-glucan. The $\beta$-1,3-glucan precipitate was dissolved in water, dialyzed with 4 L dd-$H_2O$ four times, and concentrated at reduced pressure to obtain the water-soluble $\beta$-1,3-glucan. D-Glucose (Sigma) and D-galactose (Sigma) were dissolved in dd-$H_2O$ (100 mg/ml) and stored at 4° C.

Preparation of Biotinyl-F3

*Reishi* polysaccharides-F3 were labeled with biotin using a "one pot" reaction. Specifically, *Reishi* polysaccharide-F3 (100 mg) in 0.2 N NaHCO$_3$/Na$_2$ CO$_3$ (10 mL) was reacted with biotinamidohexanoyl-6-amino-hexanoic acid N-hydroxy-succinimide ester (biotin-XX-NHS) 1.0 mg in DMF (1 mL). The mixture was stirred at room temperature for 12 h.

After completion of the reaction, the resulting solution was dialyzed using membrane tubing with a MWCO of 6000-8000 dalton (5×500 mL) at 4° C. for 48 h. After dialysis, the biotinyl-F3 was lyophilized to give a brown powder 90 mg (90%). The purification of biotinyl-F3 was monitored by HPLC and streptavidin-FITC was used for the binding assay.

Example 3

Western Blot Analysis of Purified Receptor:Fc Fusion Proteins

The purified receptor.Fc fusion proteins of Example 1 were subjected to electrophoresis, transferred onto nitrocellulose membrane (Hybond-C extra, Amersham Pharmacia Biotech) and reacted with (1:3000) peroxidase-conjugated goat anti-human IgG Ab (Jackson, Pa., USA) in TBST (5% non-fat dry milk in Tris-buffered saline with 0.02% Tween 20) buffer. After washing with TBST, blots were then incubated with enhanced chemiluminescence reagents (Amersham Pharmacia Biotech) for visualization.

Example 4

Immunosorbent Dot Binding Assay

Biotinylated F3 was blotted onto methanol-activated PVDF membranes (2 µL/dot) after 5-fold serial dilution, using a Bio-Dot Microfiltration Apparatus™ (Bio-Rad, CA, USA). After drying in air, the blot was incubated in TBST, followed by incubation with 100 µL streptavidin-conjugated horseradish peroxidase (HRP) (1:2000 dilution) (Chemicon, CA, USA). Binding reactions were visualized with enhanced chemiluminescence (ECL) reagents (Amersham. Pharmacia Biotech).

Non-biotinylated polysaccharides were also immobilized onto methanol-activated PVDF membranes, followed by incubation with 100 µL receptor.Fc fusion protein (1 µg/ml, in 2 mM CaCl$_2$/TBST) on a Bio-Dot Microfiltration Apparatus™ (Bio-Rad, CA, USA) for 1 h at room temperature, then followed by reaction with (1:3000) HRP-conjugated goat anti-human IgG antibody (Jackson, Pa., USA) in TBST (5% non-fat dry milk in Tris-buffered saline with 0.02% Tween 20) buffer. After washing with TBST, the blot was incubated with enhanced chemiluminescence reagents (Amersham Pharmacia Biotech) for visualization.

Example 5

Expression of Recombinant Receptor.Fc Fusion Protein

Figure 1B:
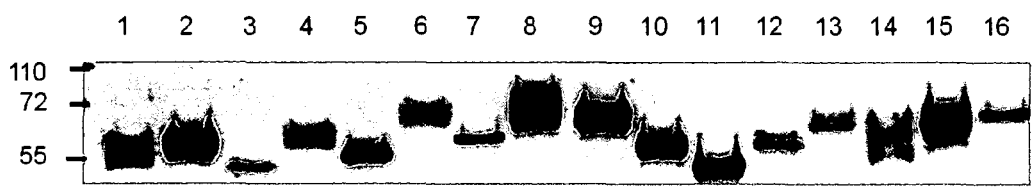

The extracellular domains of several innate immunity receptors from immune cells were cloned by reverse-transcription polymerase chain reaction (RT-PCR) according to the method of Example 1. The amplified DNA fragments were fused with the Fc portion of human IgG1 contained in the pcDNA3/hIgG1-mutant plasmid. The cloned fusion genes was transfected into 293 FREESTYLE mammalian cells, and the secreted proteins were purified by protein beads according to the method of Example 1. As shown in FIG. 1, sixteen C-type lectin genes were cloned (FIG. 1A). Specifically, FIG. 1A shows DNA fragments of innate immunity receptors amplified by RT-PCR, then fractionated on 0.8% agarose and visualized by ethidium bromide staining. FIG. 1B shows the expressed recombinant receptor.Fc fusion proteins following electrophoresis on a 12% SDS-PAGE gel. In both FIG. 1A and FIG. 1B, the following lane designations are used: Lane 1: CLEC2B/AICL, Lane 2: CLEC4C/BDCA-2, Lane 3: CLEC13A/BIMLEC, Lane 4: CLEC1A/CLEC-1, Lane 5: CLEC4D/CLEC-6, Lane 6: CLEC12A/CLL-1, Lane 7: CLEC4A/DCIR, Lane 8: CLEC4L/DC-SIGN, Lane 9: CLEC4M/DC-SIGNR, Lane 10: CLEC7A/Detin-1, Lane 11: CLEC6A/Detin-2, Lane 12: CLEC4H2/HBVxAgBP, Lane 13: CLEC4K/Langerin, Lane 14: KLRG/MAFAL, Lane 15: DVLR1/CLEC5A (MDL-1), Lane 16: CLEC4E/MINCLE. In addition, the human TREM (triggering receptor expressed on myeloid cells)-1, -2 and TREM-like transcripts (TLT)-1, -2 (Bouchon et al., 2000, J Immunol 164, 4991-5; Daws et al., 2003, J Immunol 171, 594-9; Washington et al., 2002, Blood 100, 3822-4) were also cloned and expressed by similar strategy.

Example 6

Dose-Dependent Interaction Between Immobilized Polysaccharides With Receptor.Fc Fusion Proteins The interaction between polysaccharides and the receptor.Fc fusion proteins was tested using a dot-binding assay according to the method of Example 4. The water soluble fraction 3 of *Reishi* polysaccharides (F3) (see Example 3) contains the active components to stimulate cell producing cytokines (Wang et al., 2002, Bioorg Med Chem 10, 1057-62; Chen et al., 2004, Bioorg Med Chem 12, 5595-601; Chien et al., 2004, Bioorg Med Chem 12, 5603-9; Hsu et al., 2004, J Immunol 173, 5989-99). Reichi saccharide was known to contain either a polysaccharide backbone with β-1, 3-linkages, or a polymannose backbone with α-1,4-linkage (Usui et al., 1983, Carbohydr. Res., 273; Miyazaki and Nishijime, 1982, Carbohydr. Res. 109, 290; Bao et al., 2002, Phytochemistry 59, 175-81). The Dectin-1 receptor, a member of the C-type lectin family, has been shown to interact with β-1,3-D-glycans (Brown and Gordon, 2001, Nature 413, 36-7). Dectin-1 receptor has been shown to mediate the biological effects of beta-glucans (Brown et al., 2003, J Exp Med 197, 1119-24). Thus the F3 portion of *Reishi* was tested to determine whether it could interact with the Dectin-1 receptor using the dot-binding assay of Example 4.

Figure 2A:
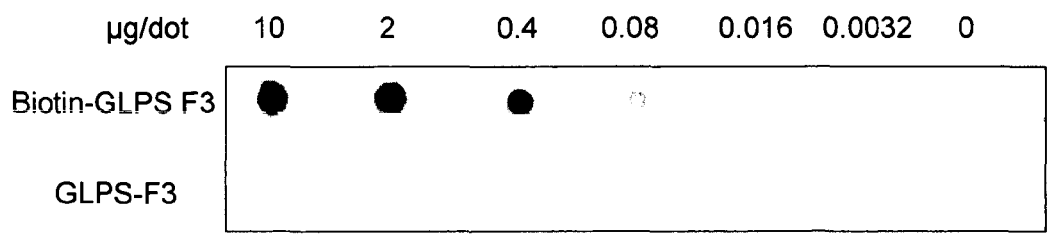

Biotinylated F3 fraction ("Biotin-GLPS F3" in FIG. 2A) (prepared according to Example 2) was immobilized on a PVDF membrane after a 5-fold serial dilution and incubated with streptavidin-conjugated HRP, and the resulting binding reaction was detected using enhanced chemiluminescence reagents (see Example 4). As shown in FIG. 2A, the sensitivity of this dot binding assay is better than about 0.08 µg. FIG. 2A also shows that no background is seen when unbiotinylated F3 ("GLPS-F3" in FIG. 2A) is immobilized on the PVDF membrane and then contacted with streptavidin-conjugated HRP.

Figure 2B:
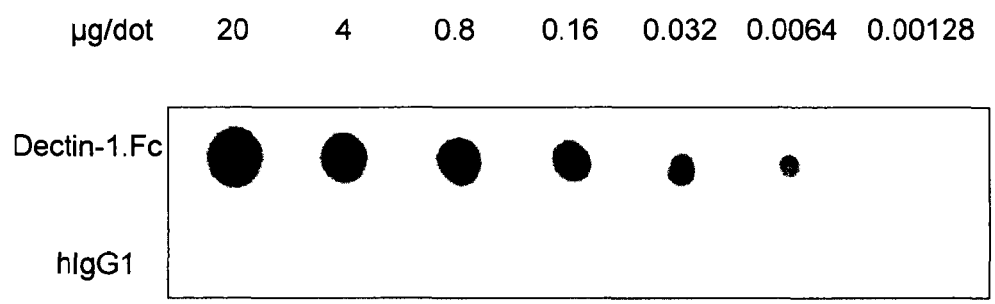

Un-biotinylated F3 fraction was also immobilized on a PVDF membrane after serial dilution, and incubated with 100 µL of 1 µg/mL Dectin-1.Fc fusion protein or human IgG1 (as a negative control), followed by incubation with goat HRP-conjugated anti-human IgG (see Example 4). As shown in FIG. 2B, Dectin-1.Fc can detect the presence of less than about 1 ng of F3 in the dot-binding assay. There is no visible background on the regions of the blot contacted with human IgG1 instead of Dectin-1.Fc.

Figure 2C:
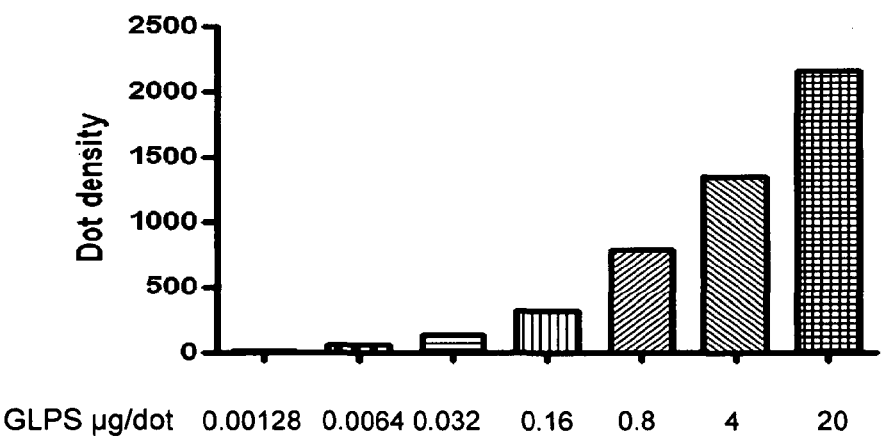

The dot density of the blot of FIG. 2B was determined by a densitometer (ImageQuant), and the results show that the Dectin-1.Fc binding signal increased in a dose-dependent manner (see FIG. 2C).

Figure 2D:
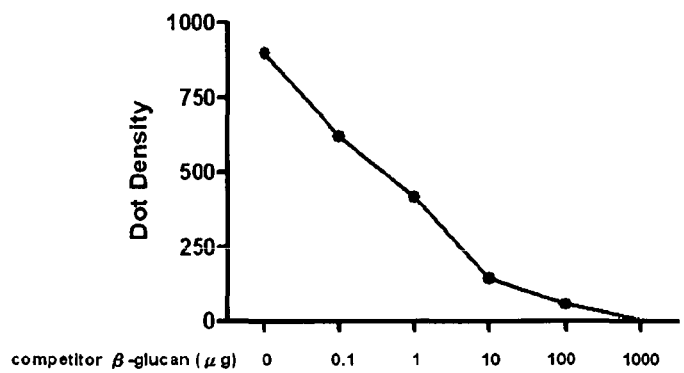
Figure 2E:
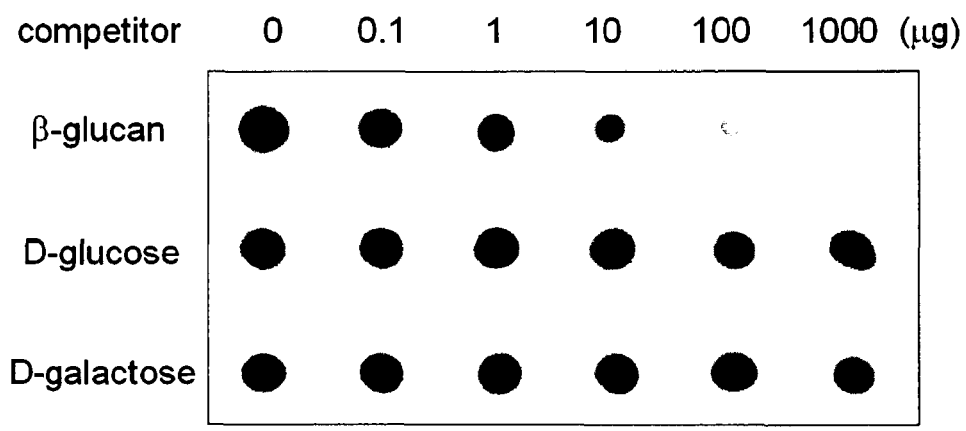

In order to determine whether other polysaccharides inhibit the interaction between F3 and Dectin-1, F3 (lopg/dot) was immobilized on PVDF membrane and then contacted with 100 µL Dectin-1.Fc (1 µg/mL) in the presence of serially diluted solutions of β-glucan, D-glucose, and D-galactose (0.1 µg-1000 µg), followed by incubation with goat HRP-conjugated anti-human IgG. FIG. 2D shows dot density analysis of the blot for competitor β-glucan, and FIG. 2E shows a blot image for all the competitors. It can be seen that the interaction between Dectin-1.Fc and the F3 fraction is inhibited by β-1,3-glucan, but not by D-glucose or D-galactose. This indicates the interaction between Dectin-1.Fc with F3 is via recognition of β-1,3-glucan.

Example 7

Identification of Receptors Capable of Interacting with F3 Fraction

Figure 4A:
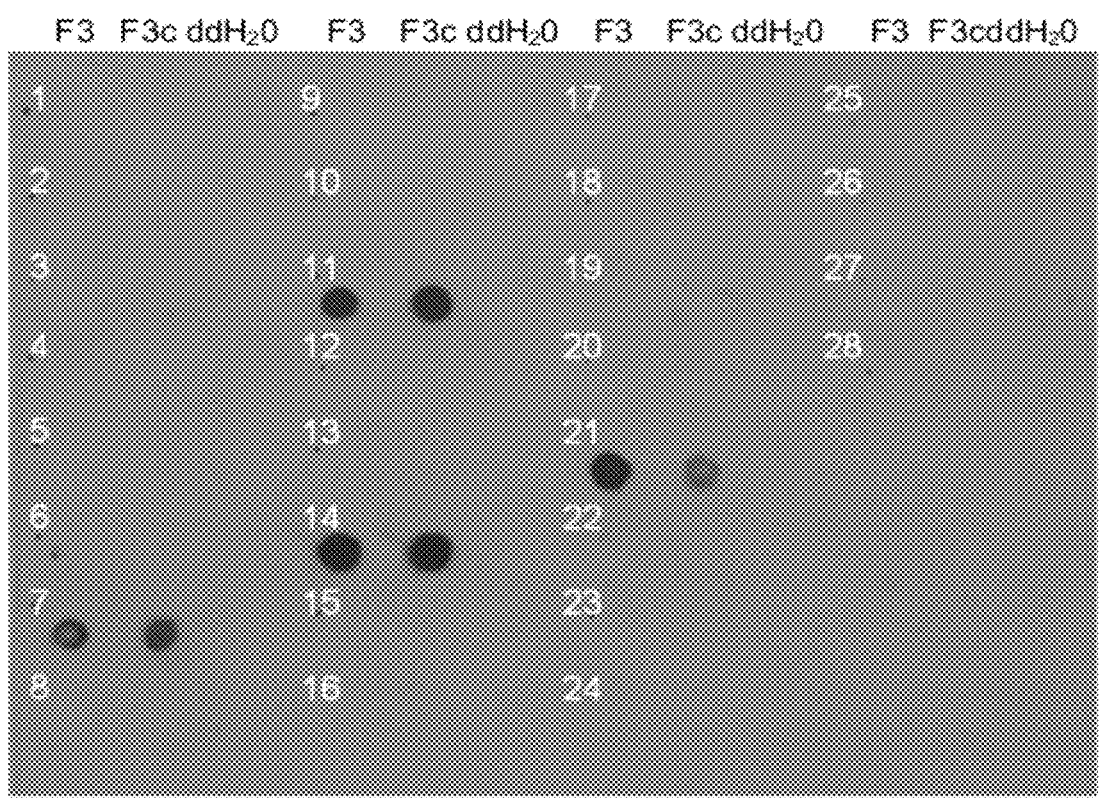

The interaction of F3 with other members of the C-type lectin family or with Ig-like receptors was assayed. Non-biotinylated F3 and non-biotinylated F3C (which is derived from F3 after passing through 100 kDa MWCO centrifugal tube) (10 µg/dot) was immobilized on PVDF membrane (see Example 4), then incubated with 100 µL of 1 µg/mL solutions of 25 different recombinant receptor.Fc fusion proteins (including 19 lectin receptors, and 8 members of TREM and TLT families) and human IgG1 as control. Binding was detected using goat HRP-conjugated anti-IgG antibody and ECL reagents. The results are depicted in table form in FIG. 3 (with relative dot intensities indicated by "+" symbols, and no detectable binding indicated by "−" symbol) and an image of the blot is depicted in FIG. 4A. The probe numbering system used in FIG. 3 is retained in FIG. 4A.

The results show that in addition to Dectin-1.Fc (probe no. 14 in FIG. 3 and FIG. 4A), F3 also interacted with KCR.Fc (probe no. 7 in FIG. 3 and FIG. 4A), DC-SIGNR.Fc (probe no. 11 in FIG. 3 and FIG. 4A), and TLT-2.Fc (probe no. 21 in FIG. 3 and FIG. 4A). It is interesting to note that F3C, which is derived from F3 after passing through 100 kDa MWCO centrifugal tube, has less binding affinity to TLT2. This suggests that TLT2 can differentiate the subtle difference between F3 and F3c.

Figure 4B:
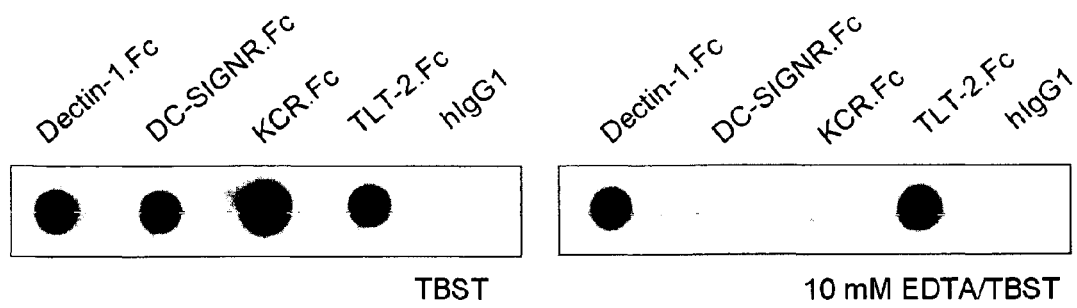

Members of the lectin receptor family rely on $Ca^{++}$ for interaction; therefore, the ability of EDTA (Ethylene Diamine Tetra Acetic Acid) to inhibit binding to F3 was studied. It was found that EDTA (10 mM in TBST) completely oabolished the interaction of F3 with KCR.Fc and with DC-SIGNR.Fc, but not the interaction of F3 with Dectin-1.Fc and TLT2.Fc. FIG. 4B depicts images of the blots made in the presence and absence of $Ca^{++}$ (left panel is TBST only; right panel is 10 mM EDTA+TBST). Binding was detected using goat HRP-conjugated anti-IgG antibody and ECL reagents. This result agrees with previous observations that the interaction between ligands and KCR (Hoyle and Hill, 1988, J Biol Chem 263, 7487-92) and DC-SIGNR is $Ca^{++}$-dependent (Soilleux et al., 2000, J Immunol 165, 2937-42), while $Ca^+$ is dispensable for the interaction between Dectin-1 and β-1,3-glucan (Herre et al., 2004, Mol Immunol 40, 869-76). Thus, F3 apparently contains abundant glycans which can interact with multiple receptors on immune cells simultaneously.

Figure 4C:
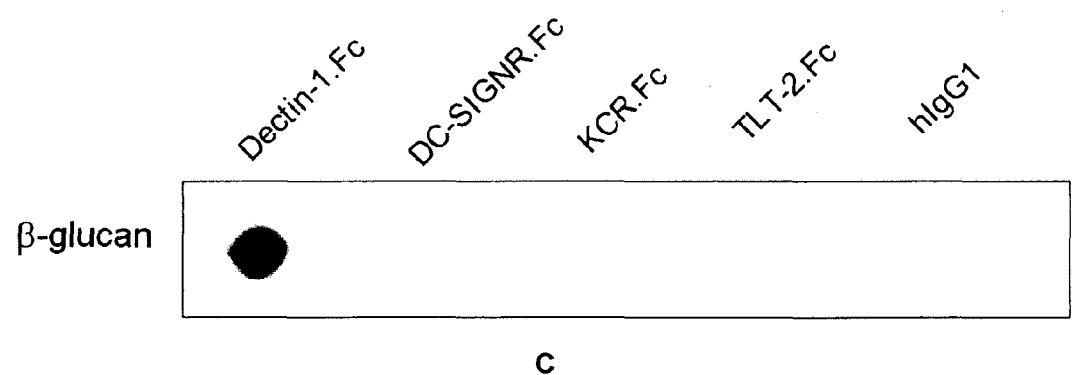

FIG. 4C depicts a dot blot using β-glucan as polysaccharide (10 µg/dot) and using 100 µL of 1 µg/mL Dectin-1.Fc, DC-SIGN.Fc, mKCR.Fc, and TLT2.Fc. Binding was detected using goat HRP-conjugated anti-IgG antibody and ECL reagents. Of the four receptor.Fc fusion proteins tested, only Dectin-1.Fc can bind to β1,3-glucan. This indicates that the other three receptor.Fc fusion proteins bind to sugar components other than β-1,3-glucan.

Example 8

Fingerprints of Polysaccharides from Various Sources

Figures 5A, 5B:
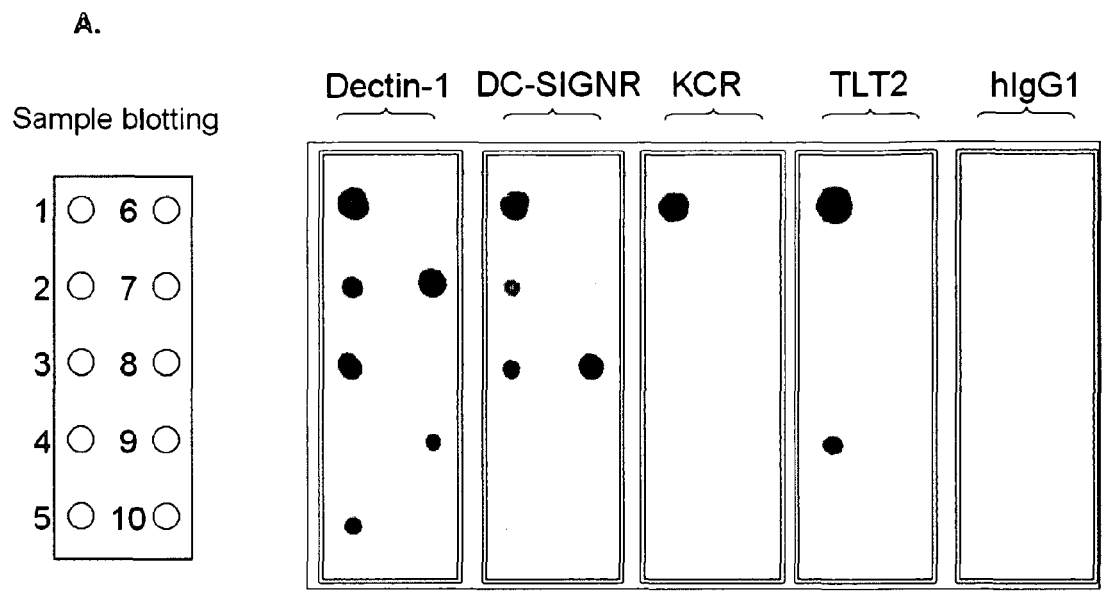

The dot-binding assay of Example 4 was performed using Dectin1.Fc, mKCR.Fc, DC-SIGNR.Fc, and TLT2.Fc fusion proteins in order to obtain the fingerprints of polysaccharides isolated from *Cordyceps* and other resources on market. Each polysaccharide composition was immobilized on a PVDF membrane as described above and then contacted with 100 L of a 11 g/mL solution of the fusion protein. Binding was detected using goat HRP-conjugated anti-IgG antibody and ECL reagents. FIG. 5A shows the individual dot blots for each fusion protein and FIG. 5B shows the sample key numbers and the relative dot intensities in table form. The *Reishi* crude extract (spot no. 5 in FIG. 5) only interacts with Dectin-1.Fc and DC-SIGNR.Fc, while the purified F3 (spot no. 1) from the crude extract interacts with all the four receptors. This indicates that the F3 purification process enriches the components that interact with immune receptors. Polysaccharide from *Cordyceps* (spot no. 7) interacts strongly with Dectin-1.Fc, indicating that the polysaccharide contains β 1,3 glycan, but its interaction with the other three receptors is much weaker than that of F3. Polysaccharides isolated from *Dendrobiun huoshanense* test positive with the iodine test reaction (see Example 2) suggesting these fractions comprise mainly α-D-glucan. In contrast to those isolated from fungi, the mixture of polysaccharides of *D. huoshanense* (spot no. 6) does not react with any of the four receptor.Fc fusion proteins. Polysaccharides isolated from mushroom polysaccharides by $ddH_2O$ (fraction L, spot no. 8) and 0.25N NaOH (fraction M, spot no. 9) (see Example 2) bind differentially to Dectin-1.Fc and DC-SIGNR.Fc. Thus, this approach can produce distinct fingerprints from polysaccharides isolated from different sources and preparations, Examples 6-8 illustrate that F3 interacts with Dectin-1.Fc, mKCR.Fc, DC-SIGNR.Fc, and TLT2.Fc. The Kupffer cell receptor (KCR) has high affinity to D-galactose and N-acetylgalactyosamine (Fadden et al., 2003, Glycobiology 13, 529-37), and is able to clear serum D-galactose- or D-fucose-terminated glycoprotein (Lehrman et al., 1986, J Biol Chem 261, 7426-32). The immunomodulatory function of F3 is dependent on the presence of fucose, and glycolytic cleavage by α1,2-fucosidase abolishes F3 activity. Thus it would be interesting to ask whether these four receptors can interact with F3 after glycolytic cleavage. DC-SIGNR/L-SIGN is structurally similar to DC-SIGN (77% identity), but it is only expressed in the endothelial cells of liver sinusoid, lymph node and placenta (Van Liempt et al., 2004, J Biol Chem 279, 33161-7). Both DC-SIGN and DC-SIGNR can bind to N-linked high-mannose oligosaccharides ($Man_9$ $GlcNAc_2$ Asn glycopeptide). However, only DC-SIGN, and not DC-SIGNR, can bind to glycans with a terminal fucose residue (Guo et al., 2004, Nat Struct Mol Biol 11, 591-8). Even though DC-SIGNR binds relatively restricted ligands than DC-SIGN, only DC-SIGNR can interact with F3. This suggests that F3 might contain a unique structure distinct from Fucα1-4GlcNAc, Lewis$^x$, Lewis$^a$ and blood group sugar epitopes (the known ligands for DC-SIGN).

TLT-2 is a member of TREM-like transcripts family, which contain a characteristic single V-set immunoglobulin (Ig) domain and a long cytoplasmic tail with a proline-rich region and an immune receptor tyrosine-based inhibitory motif (ITIM), the latter known to be used for interactions with protein tyrosine phosphatases (Washington et al., 2002, Blood 100, 3822-4; Washington et al., 2004, Blood 104, 1042-7). Since F3 has potent immunostimulatory functions, it would be interesting to study whether the removal of TLT2.Fc.binding components from F3 by affinity chromatography could further enhance the stimulatory functions of F3 in the future. Alternatively, F3 can be further purified by affinity chromatography using Dectin-1.Fc, KCR.Fc, and DC-SIGNR.Fc to remove other components in F3.

The differential fingerprints between F3 and F3c; between F3 and *Reishi* 1-3; and between mushroom polysaccharides fraction L and M, suggest that these four receptor.Fc fusion proteins exemplified herein can be used to optimize purification procedures, and to monitor the variation of polysaccharides from different sources or from different fermentation conditions.

Example 9

Figure 6A:
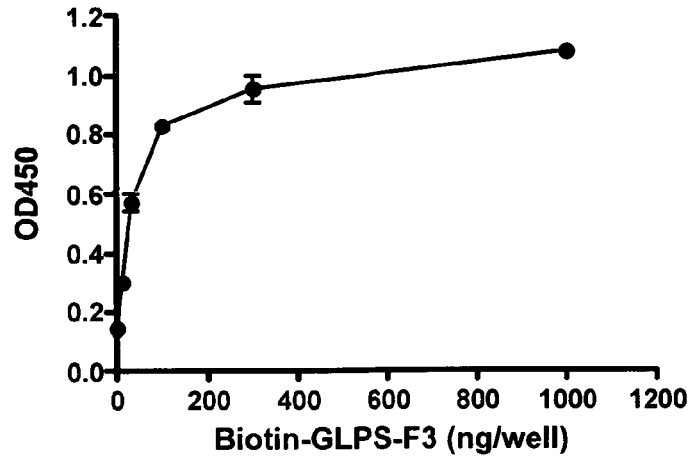

Identification of Human Lectin Receptors that Interact with GLPS-F3 By Enzyme Linked Immunoassay on Microtiter Plates The interactions of polysaccharides with receptor.Fc fusion proteins was further investigated by performing an enzyme-linked immunoassay, which was based on immobilizing GLPS-F3 through both hydrophilic and hydrophobic forces onto microtiter plates (polysytrene). In this format, the number of different receptor.Fc fusions for profiling was increased in comparison to Example 7. To optimize the quantity of GLPS-F3 for immobilization, various amounts (3-1000 ng/well, diluted in 100 mM Tris buffer, pH9.5) of biotinylated-GLPS-F3 (Biotin-GLPS-F3) were coated onto MaxiSorp StarWell microtiter plates (50 µL/well; Nunc). The plates were incubated overnight at 4° C., and then the wells were washed twice with TBST, followed by blocking with 200 µL blocking buffer (2% BSA/TBST) for 1 hour at room temperature. Peroxidase-conjugated avidin (1:5000 dilution, Vector Laboratories) and TMB (tetramethylbenzidine) substrate was then used for detection of immobilized biotinylated GLPS-F3. As shown in FIG. 6A, the quantity of Biotin-GLPS-F3 for plate coating reached plateau at 10 ng/well, which was therefore chosen to use for immobilizing un-biotinylated GLPS-F3 in EIA.

Figure 6B:
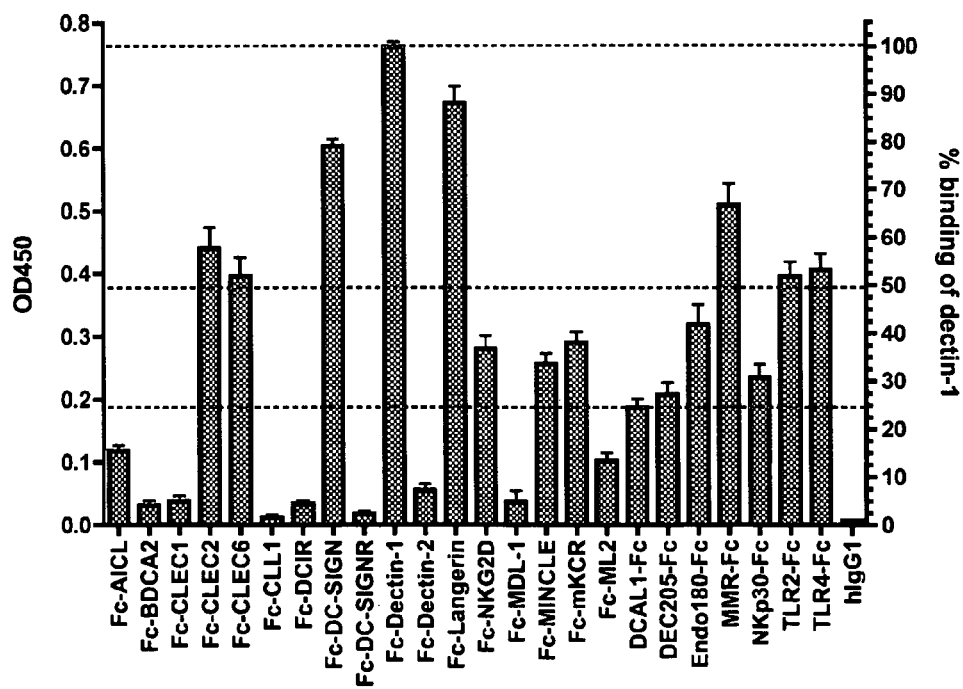

The interaction between GLPS-F3 and receptor.Fc was then tested. Unbiotinylated GLPS-F3 was immobilized at 100 ng/well as described above, and 100 µL receptor.Fc fusion protein (1 µg/ml in 2 mM $MgCl_2$/2 mM $CaCl_2$/1% BSA/TBST) was added into each well and incubated for 1 hour at room temperature. After washing with TBST, wells were incubated with peroxidase-conjugated goat anti-human IgG Ab (1:5000 dilution, Jackson ImmunoResearch Laboratories) in blocking buffer at room temperature for 30 min. Wells were incubated with 100 µL TMB substrate for 15 min after TBST washing and read at 450 nm in a Fusion plate reader (Perkin Elmer). The results were normalized with respect to Fc.Dectin-1 binding (Dectin-1 is a known lectin receptor that binds to β-1,3-glucan which is the backbone found in GLPS-F3). FIG. 6B depicts in graphical form the affinity of each receptor for GLPS-F3 relative to Dectin-1. The results show that high binding affinity to GLPS-F3 was observed for Fc.Langerin, Fc.DC-SIGN, MMR.Fc, TLR2.Fc, TLR4.Fc, Fc.CLEC-2 (CLECIB) and Fc.CLEC-6 (CLEC4D) (high binding was defined in this assay as >50% binding intensity compared to Fc.Dectin-1). It is noteworthy that TLR2 and TLR4, which have been demonstrated to play a role in GLPS-induced cell activation (Hsu et al., J Immunol 173:5989-5999 (2004); Shao et al., Biochem Biophys Res Commun 323:133-141 (2004)), bound to GLPS-F3 in the EIA format as well. There was also weaker but positive GLPS-F3 binding ability (25-50% binding intensity compared to Fc.dectin-1) found in Fc.NKG2D, Fc.MINCLE, Fc.mKCR, DCAL1.Fc, DEC205.Fc, Endo180.Fc and NKp30(NCR3).Fc. Other lectin receptors including Fc.AICL, Fc.BDCA2, Fc.CLEC1, Fc.CLL1, Fc.DCIR, Fc.DC-SIGNR, Fc.dectin-2, Fc.MDL-1 and Fc.ML2 had minimal binding ability to GLPS-F3, as did control human IgG1.

Example 10

Competition Assay for GLPS-F3-Interacting Innate Immunity Receptors

To understand the interaction of GLPS-F3 with specific innate immunity receptors, the polysaccharides mannan and β-glucan and the monosaccharides D-mannose (Man), D-glucose (Glc), N-acetyl-glucosamine (GlcNAc), D-galactose (Gal), N-acetyl-galactosamine (GalNAc), L-fucose (Fuc) and sialic acid, were used in a competition assay. Innate immunity receptors that showed higher binding ability to GLPS-F3 were examined, including Fc.Dectin-1, Fc.Langerin, Fc.DC-SIGN, TLR4.Fc, MMR.Fc, Fc.CLEC-2 (CLEC1B) and Fc.CLEC-6 (CLEC4D). The assays were carried out as in Example 9, with the addition of 1 mg/ml of each polysaccharide or monosaccharide.

Figure 7:
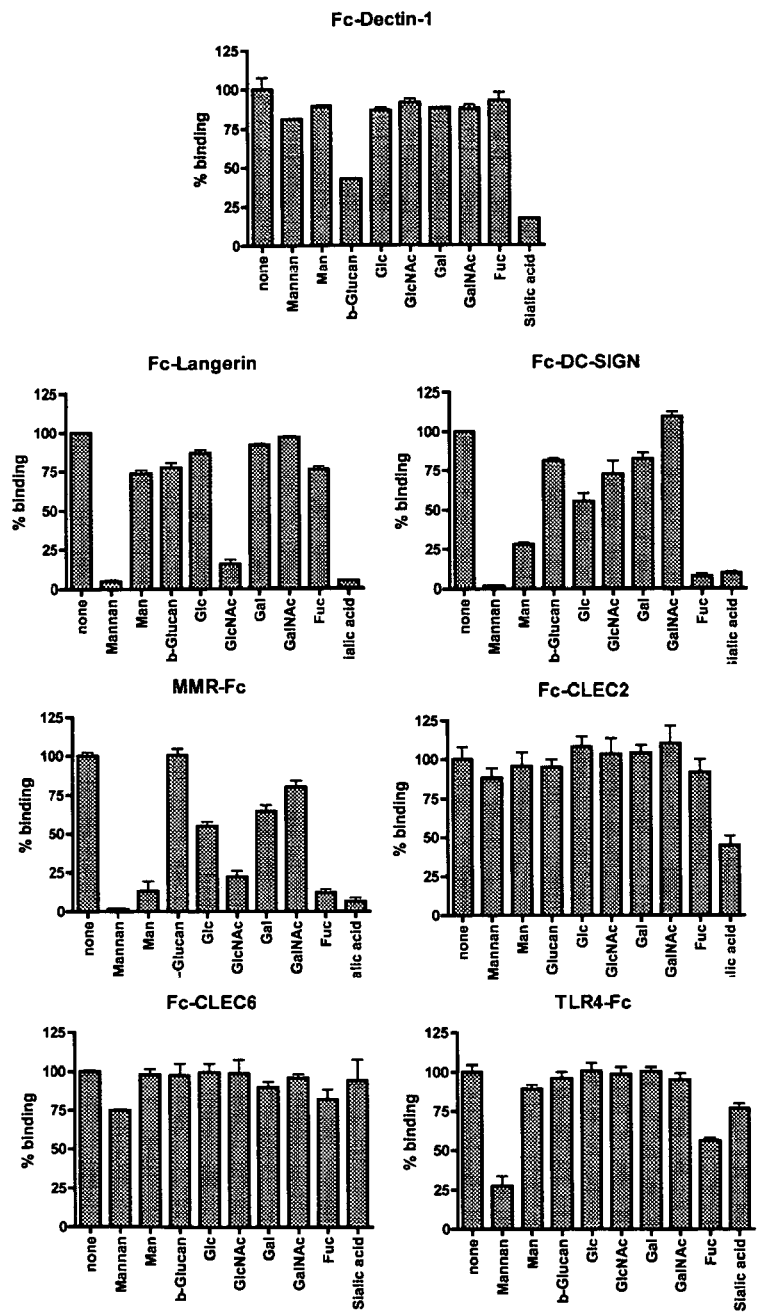

As shown in FIG. 7 (which shows graphically the % binding for each receptor/saccharide combination relative to the binding seen in the absence of saccharide) and Table I (which provides the data from FIG. 7 in tabular form), the interaction between GLPS-F3 and Fc.Dectin-1 could be blocked by β-glucan with 58% inhibition, which is in accordance with published results (Palma et al., J Biol Chem 281:5771-5779 (2006); Willment et al., J Biol Chem 276:43818-43823 (2001)). The addition of sialic acid (83% inhibition) interfered with the binding of Fc.Dectin-1 to GLPS-F3. The interaction between Fc.Langerin and GLPS-F3 was disrupted by mannan, Man and GlcNAc (95%, 26% and 84% inhibition), which are reported as the sugar ligands for Langerin (Stambach & Taylor, Glycobiology 13:401-410 (2002)); sialic acid (95% inhibition) was also observed to interfere with the binding of Fc.Langerin to GLPS-F3. As for the binding of Fc.DC-SIGN to GLPS-F3, mannan, Man, Fuc and sialic acid showed a potent blocking activity (98%, 72%, 92% and 90% inhibition), while Glc and GlcNAc had a weaker effect (45% and 27% inhibition, respectively) in blocking the interaction. Mannan, Man, Glc, GlcNAc, Gal, Fuc and sialic acid blocked the interaction (98%, 87%, 45%, 78%, 36%, 88% and 93% inhibition) between GLPS-F3 and MMR.Fc, an important lectin receptor that is known to bind Man, Fuc, GlcNAc and sialyl Lewis x (sLex) (Letuex et al., J Exp Med 191:1117-1126 (2000); Stahl, Am J Respir Cell Mol Biol 2:317-318 (1990)). The interaction of Fc.CLEC-2 to GLPS-F3 was blocked by the addition of sialic acid (55% inhibition). For Fc.CLEC-6, no obvious blocking was observed among the sugar tested. Notably, mannan and Fuc showed a blocking effect (72% and 44% inhibition, respectively) on TLR4.Fc and GLPS-F3 interaction: The data obtained here was in line with the results reported by the study of sugar ligands for Dectin-1, Langerin, DC-SIGN and MMR. It was also indicated that many lectin receptors could bind to GLPS-F3 with multivalency through different sugar components.

TABLE 1

Percentage of binding of innate immunity receptor. Fc fusions to GLPS-F3 in the presence of sugar competitors relative to binding seen in absence of sugar competitor.

| Sugar | Innate Immunity Receptor | | | | | | |
|---|---|---|---|---|---|---|---|
| | Dectin-1 | Langerin | DC-SIGN | TLR4.Fc | MMR.Fc | CLEC-2 | CLEC-6 |
| none | 100 ± 7.6 | 100 ± 1.0 | 100 ± 0.1 | 100 ± 4.5 | 100 ± 2.2 | 100 ± 8.0 | 100 ± 0.8 |
| mannan | 82 ± 0.2 | 5 ± 0.9 | 2 ± 0.5 | 28 ± 6.3 | 2 ± 0.5 | 88 ± 6.3 | 75 ± 0.8 |
| Man | 89 ± 0.5 | 74 ± 2.1 | 28 ± 1.3 | 89 ± 2.6 | 13 ± 6.4 | 95 ± 9.1 | 98 ± 3.7 |
| b-glucan | 42 ± 0.3 | 77 ± 3.2 | 81 ± 1.4 | 96 ± 4.0 | 100 ± 4.2 | 95 ± 5.1 | 98 ± 7.3 |
| Glc | 86 ± 1.5 | 87 ± 2.0 | 55 ± 5.4 | 101 ± 4.7 | 55 ± 2.9 | 108 ± 6.8 | 100 ± 5.3 |
| GlcNAc | 91 ± 2.6 | 16 ± 2.7 | 73 ± 8.6 | 99 ± 4.7 | 22 ± 3.4 | 103 ± 10.2 | 99 ± 8.5 |
| Gal | 88 ± 0.4 | 92 ± 0.9 | 82 ± 4.0 | 100 ± 2.7 | 64 ± 4.2 | 104 ± 5.1 | 90 ± 3.7 |
| GalNAc | 88 ± 2.6 | 97 ± 0.7 | 110 ± 3.1 | 95 ± 4.1 | 80 ± 4.2 | 110 ± 11.4 | 96 ± 2.4 |
| Fuc | 92 ± 5.2 | 76 ± 1.9 | 8 ± 1.8 | 56 ± 1.9 | 12 ± 2.0 | 91 ± 8.5 | 82 ± 6.5 |
| sialic acid | 17 ± 0.3 | 5 ± 0.3 | 10 ± 1.0 | 77 ± 3.1 | 7 ± 2.4 | 45 ± 6.2 | 94 ± 13.0 |

The systems presented in Examples 7-10 are useful tools for high throughput profiling of not only GLPS, but also other glycoprotein mixtures including many Chinese herb drugs currently in use. By using different surfaces for immobilizing polysaccharides (PVDF and polystyrene), different profiles were obtained for GLPS-F3. This may be due to preferential binding of certain polysaccharides within the mixtures to different surfaces. The results obtained from these two complementary formats provide "fingerprints" of polysaccharide mixtures. These strategies of fingerprinting polysaccharide mixtures can be used, for example, to monitor the contents of herb extracts under different conditions, from different sources, or from different batches. Moreover, the information gathered from the profiles of specific polysaccharide mixtures will be of great importance in understanding the underlying molecular mechanisms of their biological effects in vivo.

Example 11

Detection of the Interaction of DVLR1/CLEC5A (MDL-1) with Dengue Virus

The following examples show how the fusion proteins and methods of the disclosure can be used to identify the innate immunity receptor(s) that interact with a pathogen, and how that information can subsequently be used to determine the downstream effects of pathogen binding to the innate immunity receptor, and also to design therapeutic agents for the treatment of pathogen infection.

Dengue is one of the most important mosquito-borne viral disease affecting humans. Its global distribution is comparable to that of malaria, and an estimated 2.5 billion people live in areas at risk for epidemic transmission. The clinical syndromes after dengue virus (DV) infection include dengue fever (DF) and dengue hemorrhagic fever (DHF)/dengue shock syndrome (DSS). However, the underlying molecular mechanisms leading to DHF and DSS are still not well elucidated.

DC-SIGN is known to mediate DV infection of human dendritic cells (Tassaneetrithep et al., J Exp Med, 2003. 197 (7): p. 823-9). In order to understand the pathogenesis of DV, it is important to determine whether DV can interact with other membrane-bound C-type lectin receptors and C-type-like lectin receptors from dendritic cells, macrophages, natural killer cells, and peripheral blood mononuclear cells (PBMCs). To this end, the extracellular domains of DVLR1/CLEC5A (MDL-1), Dectin-1, KCR, and DC-SIGN (as a positive control) were fused to the Fc portion of human IgG1. Specifically, primers for DC-SIGN (SEQ ID NO: 17 and SEQ ID NO:18), DVLR1/CLEC5A (SEQ ID NO: 21 and SEQ ID NO:22), Dectin-1 (SEQ ID NO:25 and SEQ ID NO:26) and KCR (forward: 5'-CAGCCTTGGAGACCTGAGT-3' SEQ ID NO: 37; reverse 5'-TAGCCTACTCTGGCCGC-3' SEQ ID NO:38) were used to generate amplified cDNA fragments. Each forward primer had an extra BamH1 site, and each reverse primer had an extra EcoRI site to facilitate the subcloning of the amplified cDNA into the pcDNA3.1 (Invitrogen) mammalian expression vector containing the human IgG1 Fc portion. The resulting vector was then transfected into 293 FreeStyle cells (Invitrogen) to produce soluble recombinant proteins. All recombinant receptor.Fc fusion proteins were purified by protein A Sepharose beads (Pharmacia) and eluted with 0.1M glycine-HCl (pH0.3).

One μg of each receptor.Fc fusion protein was coated onto microtiter plates overnight at 4° C. DV ($5 \times 10^6$ particles) of strain 16681 (a DEN2 strain) in binding buffer (1% BSA, 2 mM $CaCl_2$, 2 mM $MgCl_2$, 50 mM Tris-HCl pH 7.5, 150 mM NaCl) was then added to the plates and the plates were incubated for 2 hours. After washing non-bound virus, a biotinylated anti-DEN2 envelope protein antibody (Wu et al., J Virol, 2002. 76(8): p. 3596-604) was applied to bind to the virus for 1 hour. Diluted horseradish peroxidase-conjugated streptavidin was then added to the plates, followed by a 1 hour incubation. TMB substrate was then added and the plates were read using an ELISA reader at OD450 nm.

Figure 8A:
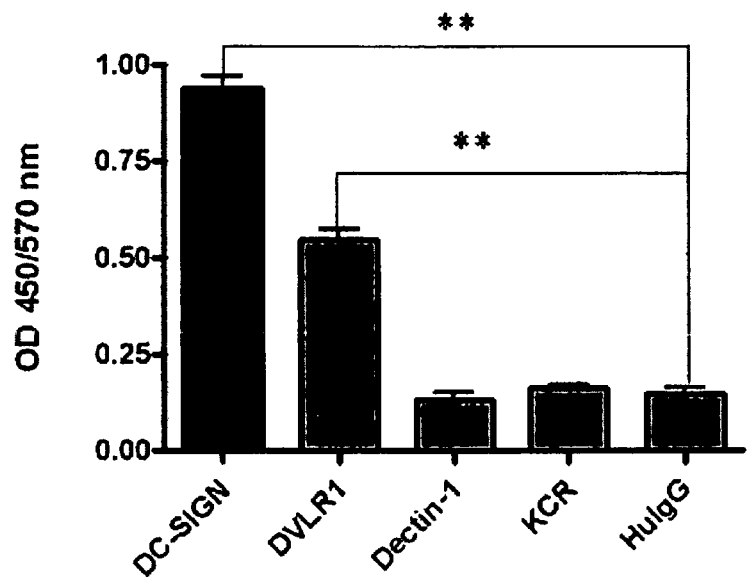
Figure 8B:
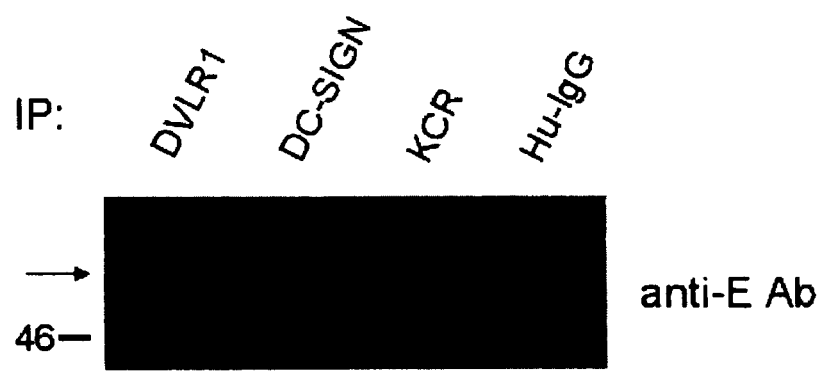

The results are depicted in FIG. 8A ( indicates p<0.01, * indicates p<0.001 (Student's t test)). The results show that in addition to DC-SIGN (positive control), DV also binds to DVLR1/CLEC5A. To confirm this result, immunoprecipitation studies were performed with human IgG1 (negative control), DC-SIGN.Fc, KCR.Fc, and DVLR1/CLEC5A.Fc. Specifically, $5 \times 10^6$ Dengue virus particles were incubated with 5 μg of each protein, and then Protein A beads were added. The resulting immunocomplexes were washed, separated by SDS-PAGE, and transferred onto nitrocellulose membrane. The membrane was then probed with biotinylated anti-DEN2 envelope protein antibody and developed with horseradish peroxidase-conjugated streptavidin. The results are shown in FIG. 8B. The results show that only DC-SIGN.Fc and DVLR1/CLEC5A.Fc were able to immunoprecipitate DV.

Figure 8C:
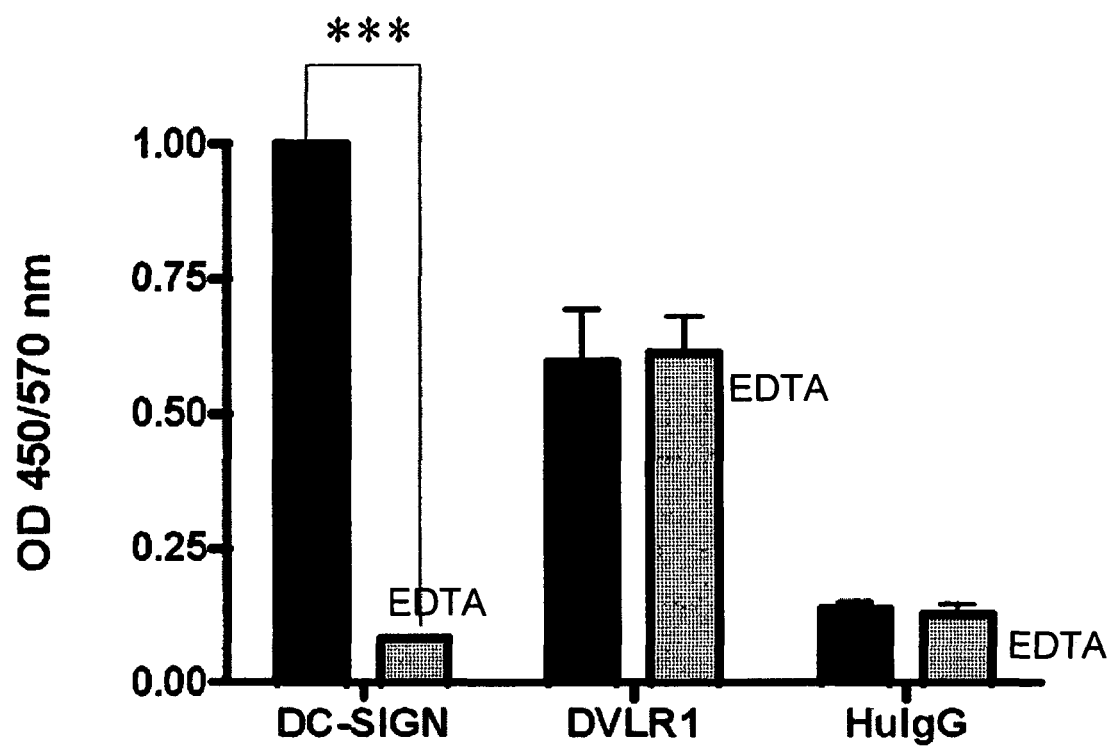

The microtiter plate assay was repeated in the presence of EDTA (10 mM) to chelate $Ca^{++}$ cations. The results (FIG. 8C) reveal that DVLR1/CLEC5A binding to Dengue virus is $Ca^{++}$ independent, whereas DC-SIGN binding is $Ca^{++}$ dependent (*** indicates p<0.001, Student's t test).

Figure 8D:
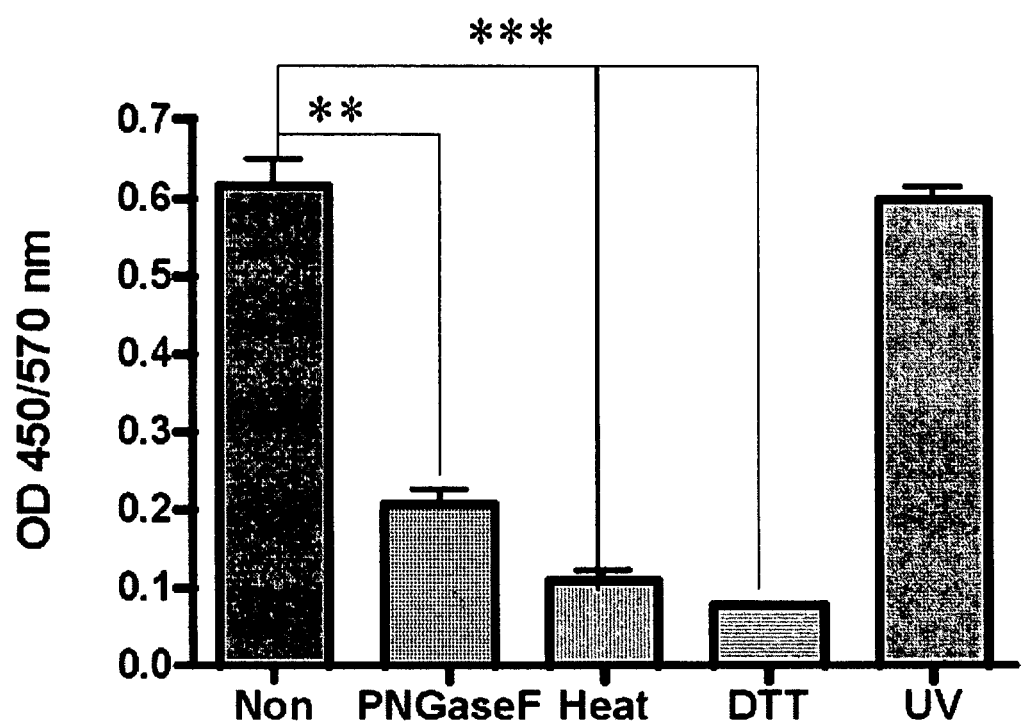

The microtiter plate assay was also repeated for DVLR1/CLEC5A.Fc fusion protein with DV particles ($5 \times 10^6$) that had been 1) preincubated with 500 U of the glycosidase PNGaseF (New England Biolabs, Inc.) overnight at 37° C.; or 2) treated with dithiothreitol (DTTI) (0.1M); or 3) incubated at 95° C. for 5 minutes; or 4) UV irradiated for 5 minutes. The results are shown in FIG. 8D (asterisks indicate where the binding affinity of DVLR1/CLEC5A.Fc fusion protein is altered by modification of the virus relative to non-treated virus;  p<0.01, * p<0.001, Student's t test). The results indicate that pretreatment of DV with PNGase F inhibited DVLR1/CLEC5A.Fc interaction significantly, and that pretreatment with either heat or dithiothreitol almost completely inhibited DVLR1/CLEC5A.Fc binding, but not DC-SIGN.Fc binding to DV. This suggests that both the sugar epitope(s) and the three dimensional conformation of DV are important for binding to DVLR1/CLEC5A.

To evaluate the expression of DVLR1/CLEC5A on immune cells, flow cytometric analysis was performed on human polymorphonuclear (PMN) cells (neutrophils), PBMCs, macrophages, and dendritic cells. PMNs and PBMCs were isolated from the whole blood of human healthy donors by dextran sedimentation as described (Kuan et al., Br. J. Pharmacol., 2005, 145(4):460-468) and standard density gradient centrifugation with Ficoll-Paque respectively (Amersham Biosciences, Piscataway, N.J.). Purified neutrophils were resuspended in phosphate saline buffer (PBS, pH 7.4) with hypotonic lysis of erythrocytes. CD14+ cells were subsequently purified from PBMCs by high-gradient magnetic sorting using the VARIOMACS technique with anti-CD 14 microbeads (Miltenyi Biotec GmbH, Bergisch Gladbach, Germany), then were cultured in complete RPMI-1640 medium (Life Technologies, Gaithersburg, Md.) supplemented with ng/ml human M-CSF (R&D Systems, Minneapolis, Minn.) for 6 days (Chang et al., J. Leukoc Biol, 2004, 75(3):486-494). Dendritic cells (DC) were generated from adherent PBMCs by culture in RPMI 1640 medium supplemented with 10% fetal calf serus, 800 U/ml human GM-CSF (Leucomax; Schering-Plough, Kenilworth, N.J.), and 500 U/ml human IL-4 (R&D Systems) for 6 days (immature DCs). To prepare mature activated DCs, immature DCs were further incubated with gamma-irradiated (5500 rad) CD40 ligand (CD40L)-expressing L cells (DNAX Research Institute, Palo Alto, Calif.) at a ratio of 3:1 for 36 hr (Hsu et al., J. Immunol., 2002, 168(10):4846-4853).

Figure 9A:
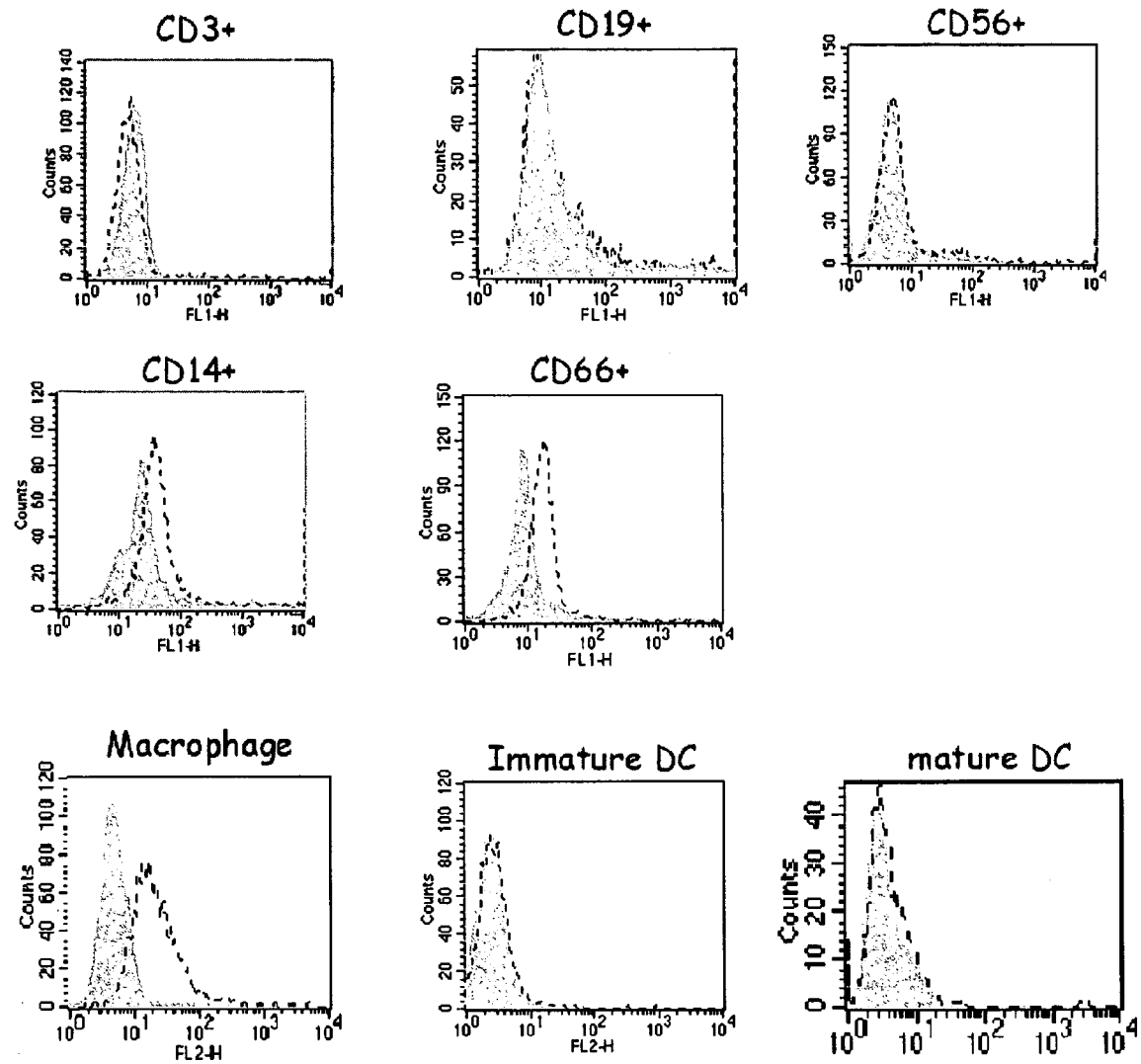
Figure 9B:
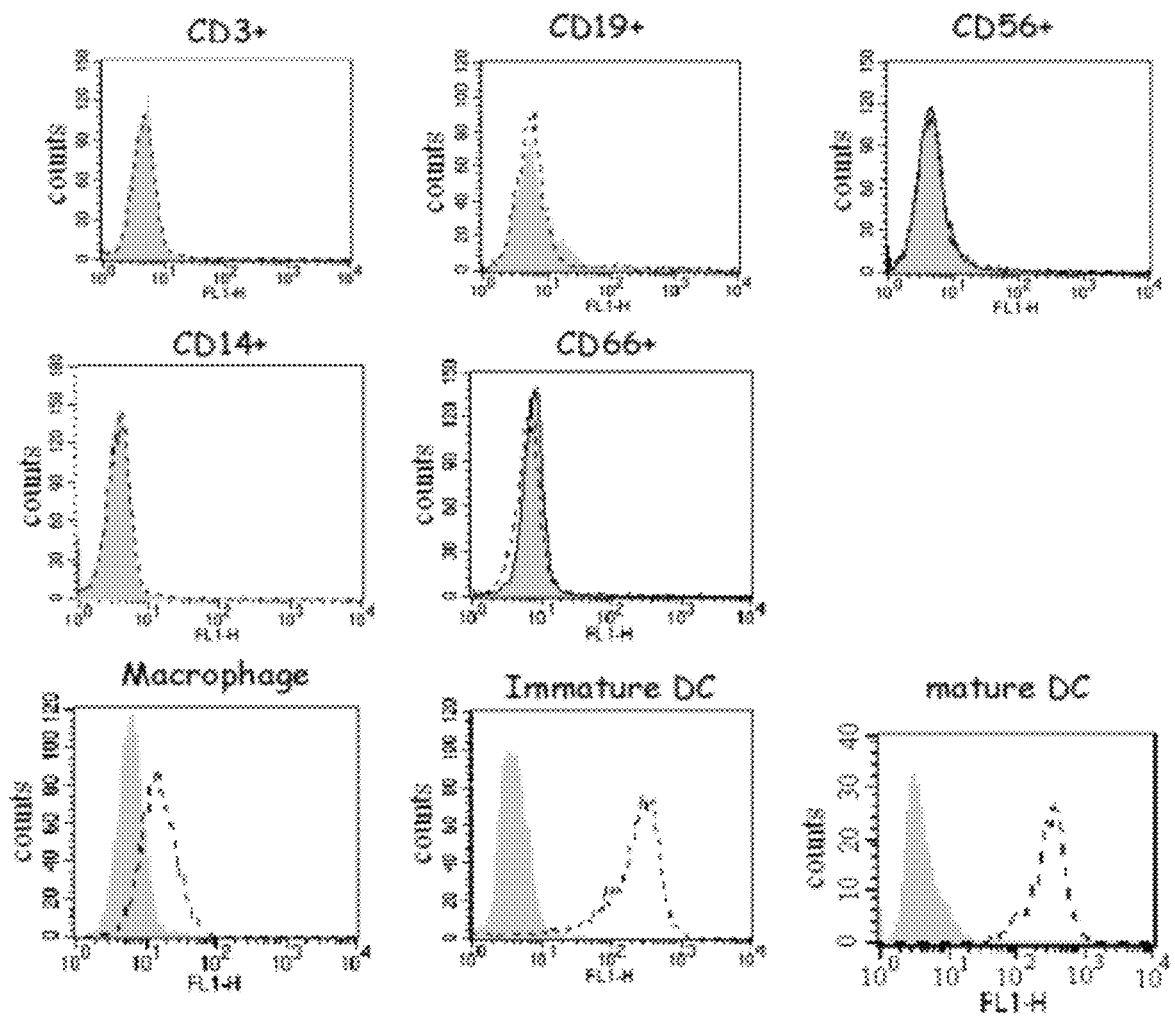

Flow cytometry was performed on the above-mentioned cell types using FITC-conjugated anti-DVLR1/CLEC5A monoclonal antibodies (R&D Systems, Minneapolis, Minn.), or FITC-conjugated anti-DC-SIGN monoclonal antibodies (ED PharMingen), in conjunction with Phycoerythrin (PE)-conjugated anti-CD3, CD19, CD56, CD14, and CD66 antibodies for double staining (BD PharMingen). Matched isotype controls (IgG2b for DVLR1 mAb, IgG 1 for DC-SIGN; Sigma) were also performed in this surface staining to provide background information. Fluorescence was analyzed by FACSCalibur flow cytometry (Becton Dickinson) with CellQuest software (Becton Dickinson). CD marker positive cells were gated to determine the expression of DVLR1/CLEC5A or DC-SIGN. The results are shown in FIG. 9A (DVLR1/CLEC5A) and FIG. 9B (DC-SIGN) (shaded area represents isotype control). The results indicate that DC-SIGN is mainly expressed on immature dendritic cells, and is weakly expressed on macrophages. The results also indicate that DVLR1/CLEC5A was detected on the surface of CD14+ derived macrophages (MΦ), CD66+ PMNs and CD14+ freshly isolated PBMCs, but not on CD14+ derived immature and mature dendritic cells. This is in accord with previous observations that DVLR1/CLEC5A mRNA is expressed in human monocytes and macrophages, but not in dendritic cells (Bakker et al., Proc. Natl. Acad Sci USA, 1999, 96(17):9792-9796).

The results presented in this example show that the receptor.Fc fusion protein-based methods disclosed herein can be used to determine the identity of the innate immunity receptors that bind to a specific pathogen, such as Dengue virus. This in turn allows one to identify the cell types that interact with the pathogen, and furthermore provides a new target for treatment or prevention of infection by the pathogen. For example, the results disclosed herein suggest that agents that prevent DV from binding to DVLR1/CLEC5A can be used for prophylactic or therapeutic purposes. For example, monoclonal antibodies against DVLR1/CLEC5A can be generated by one skilled in the art that prevent the binding of DV to DVLR1/CLEC5A. Moreover, since DV is a member of the family Flaviviridae, this result suggests that DVLR1/CLEC5A may interact with other viruses within the same family, for example, viruses within the genus Flavivirus (such as West Nile Virus, Japanese encephamyelitis virus (JEV), yellow fever virus, tick-borne encephamyelitis virus) and viruses within the genus Hepacivirus (such as Hepatitis C virus). Accordingly, DVLR1/CLEC5A may serve as a therapeutic or prophylactic target for these viruses also. In addition, since DVLR1/CLEC5A is a pattern recognition receptor, DVLR1/CLEC5A may serve as a therapeutic or prophylactic target for other enveloped viruses.

Example 12

Dengue Virus Induced DAP12 Phosphorylation is Mediated Via DVLR1/CLEC5A

DVLR1/CLEC5A (MDL-1) is a type II transmembrane protein comprising 187 aa in length, and it includes a charged residue in the transmembrane region that enables it to pair with DAP12 (DNAX activating protein of 12 kDa) (Bakker et al., Proc. Natl. Acad Sci USA, 1999, 96(17):9792-9796). DAP12 is a disulfide-linked, homodimeric transmembrane protein with a minimal extracellular domain, a charged aspartic acid in the transmembrane domain and an ITAM (immunoreceptor tyrosine-based activation motif) in its cytoplasmic tail. Because DV binds to DVLR1/CLEC5A on CD14+ macrophages, and because DAP12 has an ITAM, it was of interest to determine whether DV can induce DAP12 phosphorylation in CD14+ macrophages. Accordingly, CD14+ macrophages were infected with DV using the a slight modification of the method disclosed in Chen et al, J. Virol. 2002, 76(19):9877-9887. Briefly, terminal differentiated macrophages were washed once with incomplete RPMI medium to remove fetal calf serum in culture medium. The cells were then infected with DV at different multiplicities of infection (MOI). The virus was incubated with the cells in serum-free RPMI at 37° C. for 2.5 h to permit viral adsorption. The culture plates were gently agitated every 30 min for optimal virus-cell contact. Thereafter, the unabsorbed viruses were removed by washing the cell monolayers twice with serum-free RPMI and then once with incubation, the cell-free supernatants were harvested separately and stored in aliquots at −80° C. until assayed for infectious-virus production and cytokine secretion (see Example 13). Infectious virus titers were determined by a plaque forming assay on BHK-21 cells. Plaques were counted by visual inspection at 7 days after crystal violet overlay to determine the number of plaque-forming units (PFU) per mL of supernant (Lin et al., J. Virol., 1998, 72(12): 9.729-9737). To detect intracellular DV antigens, infected cells were fixed with 1% paraformaldehyde and permeabilized with 0.1% saponin, followed by staining with NS3 mAb (Lin et al., J. Virol., 1998, 72(12):9729-9737) or matched isotype control (IgG1; Sigma). After incubation for 1 h, PE-conjugated goat F(ab)' anti-mouse IgG secondary was added for fluorescence detection and fluorescence was analyzed by FACSCalibur flow cytometry with CellQuest software.

Figure 10A:
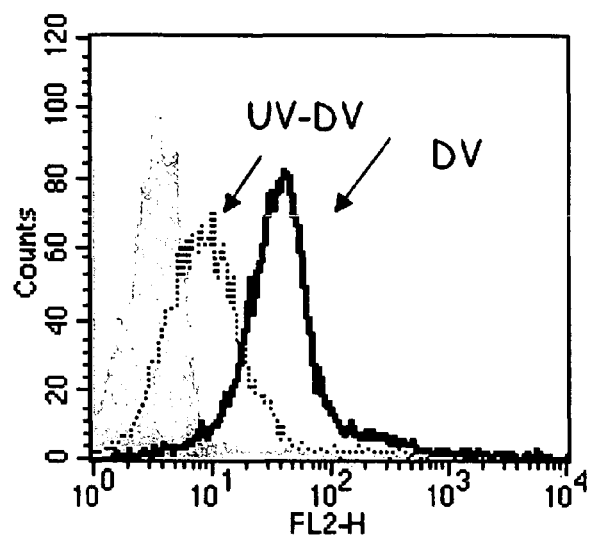
Figure 10B:
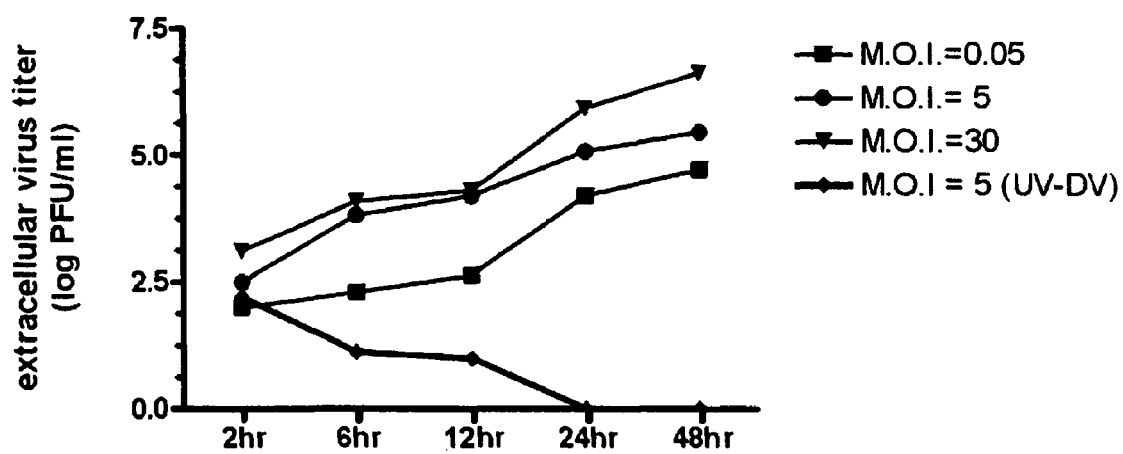

The results are shown in FIG. 10A-D. At 48 h after infection at MOI=5, DV non-structural protein 3 (NS3) was detected by flow cytometry in the cytosol of macrophages (FIG. 10A; gray histogram is antibody isotype control). The extracellular virus titer was measured at various times following infection, and revealed that virus particles were released to culture supernatant when macrophages were infected with live DV, but not with UV-irradiated DV (UV-DV; 254 nm irradiation for 15 minutes on ice at 5 to 10 cm distance) (FIG. 10B).

DAP12 phosphorylation was studied 2 hours after infection at varying MOIs (MOI=0.05-30, 2 h after infection), and also at a fixed MOI (MOI=5) over a time course (2-48 h after infection). Specifically, for detection of phospho-DAP12, macrophages were stimulated with DV for the appropriate amount of time at the appropriate MOI and then lysed in lysis buffer (50 mM Tris-HCl [pH7.5], 150 mM NaCl, 1% Triton X-100, 0.1% SDS, 5 mM EPTA, 10 mM NaF, 1 mM sodium orthovanadate, and proteinase inhibitor cocktail tablet [Roche]). Equal amount of total cell extracts were immunoprecipitated with DAP12 rabbit polyclonal antibody (Santa Cruz Biotechnology Inc, CA) and protein A sepharose (Amersham Biosciences AB) for 4 h at 4° C. After incubation, the immunocomplex was washed three times and separated by SDS-PAGE, followed by transferring onto nitrocellulose membrane and probed with anti-phosphotyrosine antibody (4G10; Upstate Biotechnology, Inc). Immunoblots were developed using HRP-conjugated second antibody and enhanced chemiluminescence (Amersham). For reprobing, the membrane was stripped with a strong re-probe kit (Chemicon) and blotted with DAP12 antibody.

Figure 10C:
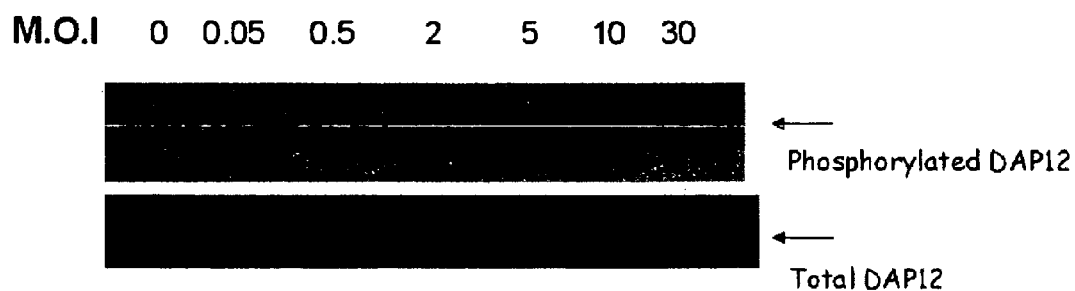
Figure 10D:
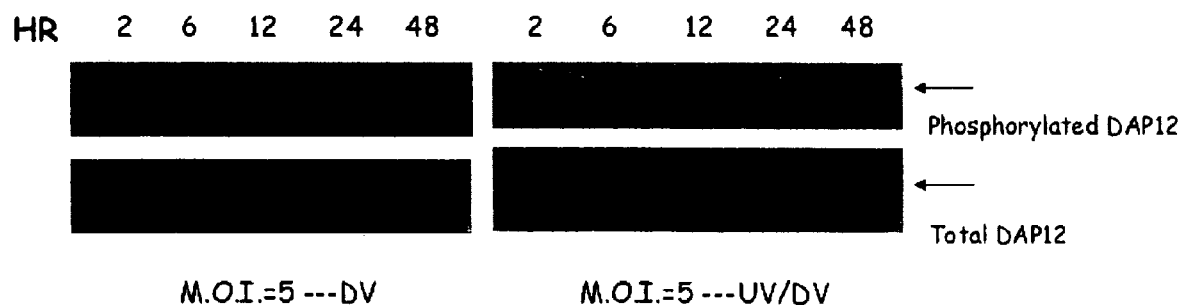

The results obtained at various MOIs are shown in FIG. 10C, and the time course experiment results are shown in FIG. 10D. The results show that at 2 h after DV infection, the intensity of DAP12 phosphorylation increased as the MOI was raised from MOI=0.05, reaching a peak when MOI=5 (FIG. 10C). DAP12 phosphorylation was detected at 2 h after DV infection, peaked at 12 h, and lasted for at least 48 h (FIG. 10D). Even though UV-DV could not replicate in CD14+ macrophages and had no activity in a plaque assay (FIG. 10B), DAP12 was also phosphorylated at 2 h and phosphorylated DAP12 remained detectable at 12 h, even though the intensity is much weaker than that induced by live DV (FIG. 10D; UV-DV). This suggests that DV-induced DAP12 phosphorylation has two phases: phase I (in the first 6 h) is replication-independent, while phase II (after 12 h) is replication-dependent.

To confirm that DAP12 phosphorylation was via DVLR1/CLEC5A, RNA interference (RNAi) with short hairpin RNA (shRNA) was used to inhibit the expression of DVLR1/CLEC5A in CD14+ macrophages and DAP12 phosphorylation was assayed as above. Specifically, the coding region of human DVLR1/CLEC5A was targeted with the following DVLR1/CLEC5A siRNA:

SEQ ID NO: 39
5'-TTGTTGGAATGACCTTAT-3'

This stretch was adapted with loop sequence (TTCAA-GAGA) from Brummelkamp et al., Science, 2002, 296(5567): 550-553, to create an shRNA. The polymerase III terminator stretch used here was TTTTTT. The shRNA was cloned into the pLL3.7 gene silencing vector (Rubinson et al., Nat. Genet., 2003, 33(3):401-406) which contained loxP sites, a CMV (cytomegalovirus) promoter driving expression of enhanced green fluorescent protein (EGFP), and a U6 promoter with downstream restriction sites (HpaI and XhoI). A DC-SIGN shRNA construct was also constructed by subcloning the shRNA contained in the construct pSUPER-siDC-SIGN (Tassaneetrithep et al., supra) into pLL3.7 vector digested with HpaI/XhoI. The constructs were electroporated into macrophages using the Amaxa kit (Gaithersburg, Md.) according manufacturer's specifications. Briefly, macrophages ($6 \times 10^6$) were harvested as described above and resuspended in 100 µL of nucleofactor solution. After the addition of siRNA (5 µg) or vector control, cells were electroporated using Amaxa program Y-001 and allowed to recover for 16 h. The efficiency of DVLR1 and DC-SIGN silencing was analyzed 24 hrs after transfection by immunoblotting using anti-DVLR1/CLEC5A and DC-SIGN monoclonal antibodies (R&D Systems), respectively.

Figure 11:
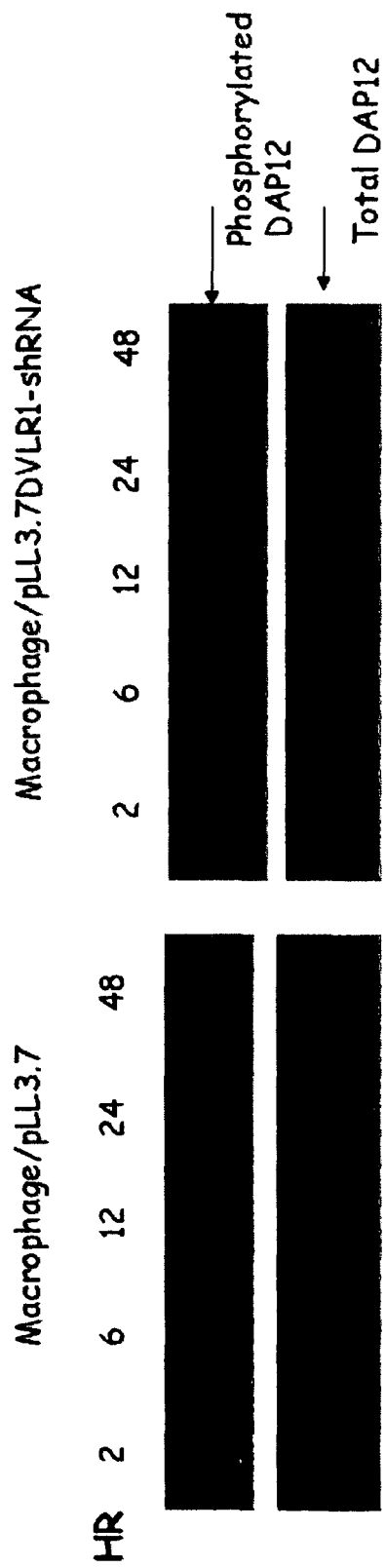

The results are shown in FIG. 11. CD14+ macrophages electroporated with the control vector pLL3.7 or with DC-SIGN-shRNA did not show a reduction in DAP12 phosphorylation after DV infection. By contrast, DAP12 phosphorylation decreased dramatically in CD14+ macrophages electroporated with DVLR1/CLEC5A-shRNA prior to DV infection. Therefore, it was concluded that DV-induced DAP12 phosphorylation occurs via DVLR1/CLEC5A.

Example 13

Figure 12A:
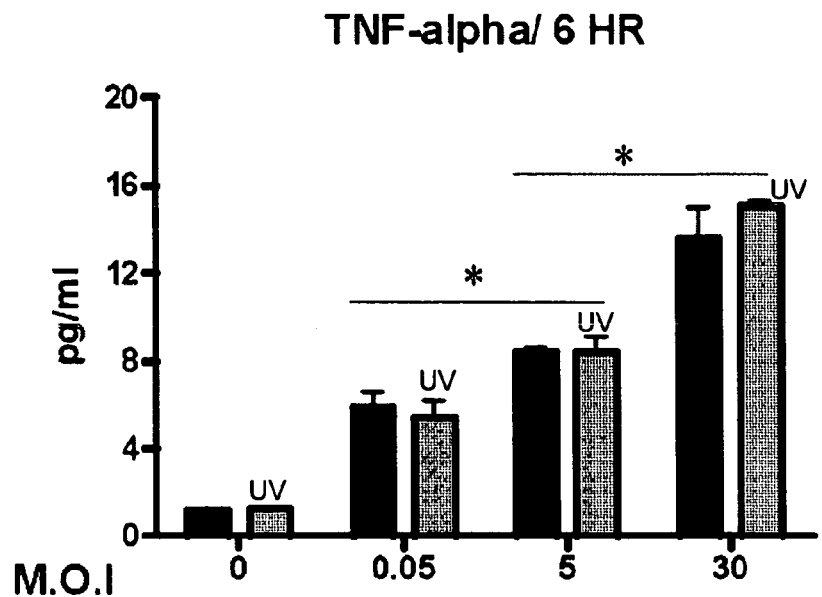
Figure 12B:
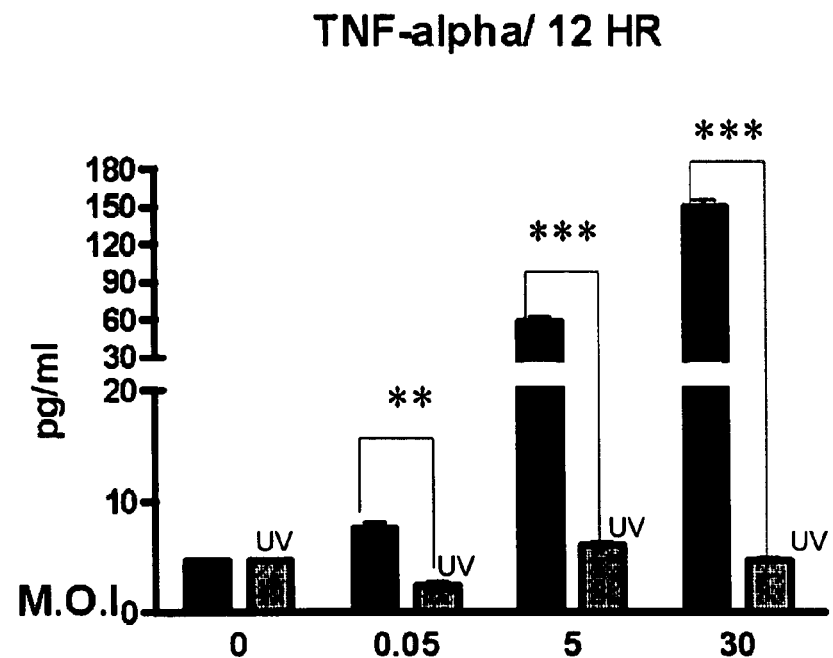
Figure 12C:
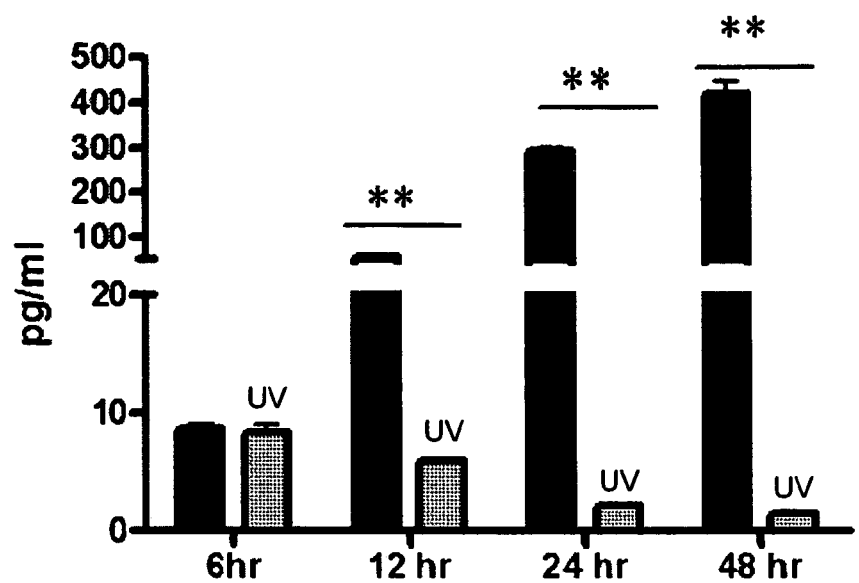

DVLR1/CLEC5A is Involved in DV-Mediated TNF-α Release, But not Entry to CD14+ Macrophages Upon DV infection, CD14+ macrophages secrete pro-inflammatory cytokines and chemokines, including tumor necrosis factor alpha (TNF-α), alpha-interferon (IFN-α), MIP-1α, and IL-8 (Chen et al, supra). The levels of TNF-α in culture supernatant were measured in DV-infected CD14+ macrophages using a commercial ELISA kit. Measurements were made at different MOIs and at different times post-infection for both live DV and UV-DV. The results are shown in FIG. 12A-C (error bars represent the standard error from the mean of triplicates, and asterisks indicate statistically different levels of cytokine production, $*=p<0.05$; $=p<0.01$; $*=p<0.001$). The results show that at 6 hours post infection, both live DV and DV-UV had similar effects on TNF-α secretion at MOIs ranging from 0.05-30 (FIG. 12A). At 12 hours post infection, TNF-α secretion increased in a dose dependent (increasing MOI) manner only for live DV. For UV-DV infected cells at 12 hours post infection, TNF-α levels remained the same at all MOIs (FIG. 12B). FIG. 12C shows a time course measurement of TNF. The results show that when infected with live DV at MOI=5, TNF-α secretion increased rapidly from 6 h (8 µg/ml) to 12 h (85 µg/ml), and peaked at 48 h (350 µg/ml). When incubated with UV-DV, however, TNF-α secretion decreased from 8 µg/ml (at 6 h) to 5 µg/ml (at 12 h). This suggests that the initial response (at 6 h) is independent of virus replication, while the later phase of TNF-α secretion (after 12 h) correlates with DV replication.

Figure 13A:
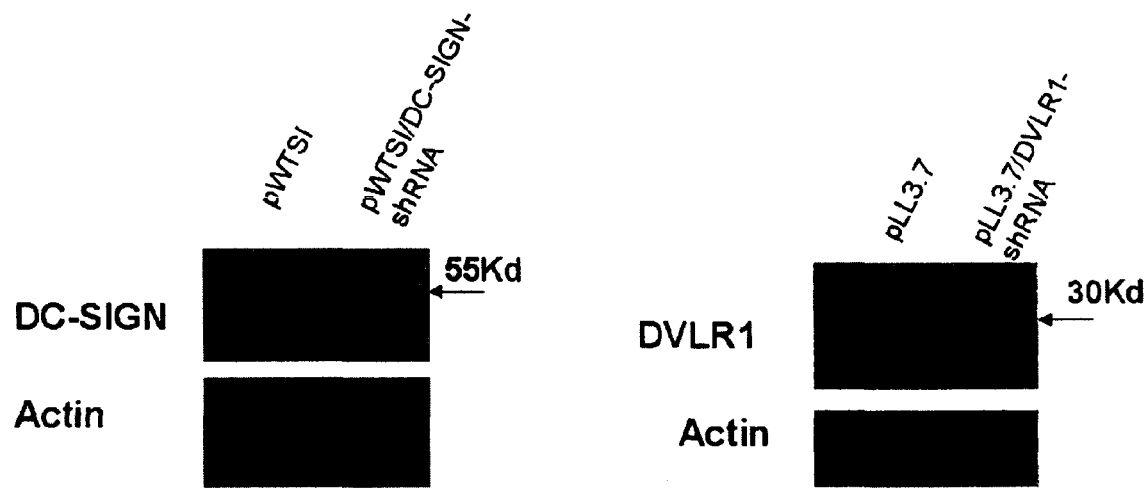
Figure 13B:
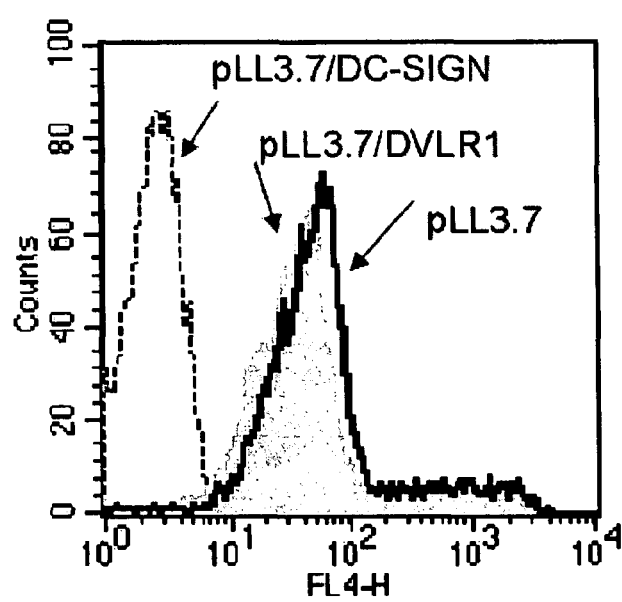
Figure 13C:
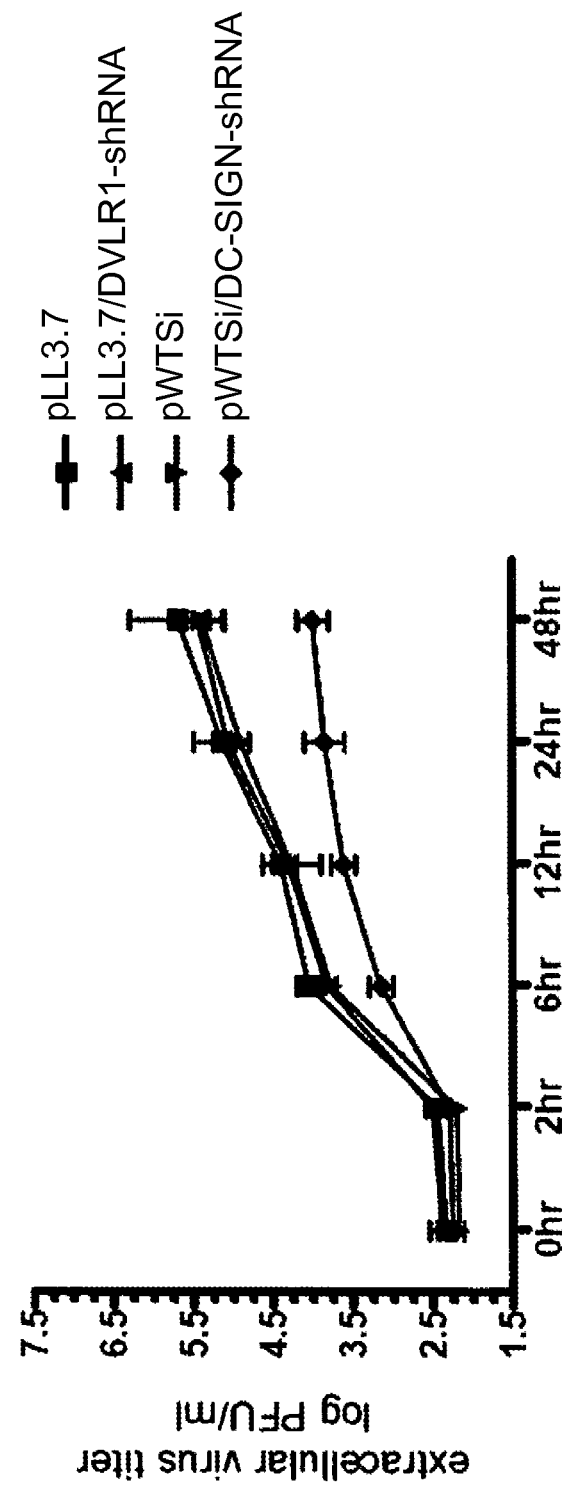

DC-SIGN has previously been shown to interact with DV in order to mediate virus entry into dendritic cells. Using the RNAi methodology and reagents of the prior examples, the effect of DC-SIGN-shRNA and DVLR1/CLEC5A-shRNA on NS3 expression in DV-infected CD14+ macrophages was investigated. FIG. 13A shows that DC-SIGN-shRNA and DVLR1/CLEC5A-shRNA can knock down their respective proteins (pWTSI and pLL3.7 are no insert controls). FIG. 13B depicts the results of flow cytometry analysis and illustrates that only DC-SIGN-shRNA could attenuate DV NS3 expression in CD14+ macrophages. This result was confirmed using immunofluorescence confocal microscopy using anti-DS3 antibodies. FIG. 13C illustrates real time PCR analysis of virus titer in the supernatant of cells electroporated with the shRNA constructs. The results indicate that only DC-SIGN-shRNA is capable of reducing virus titer in the supernatant of DV-infected cells.

Example 14

Figure 14A:
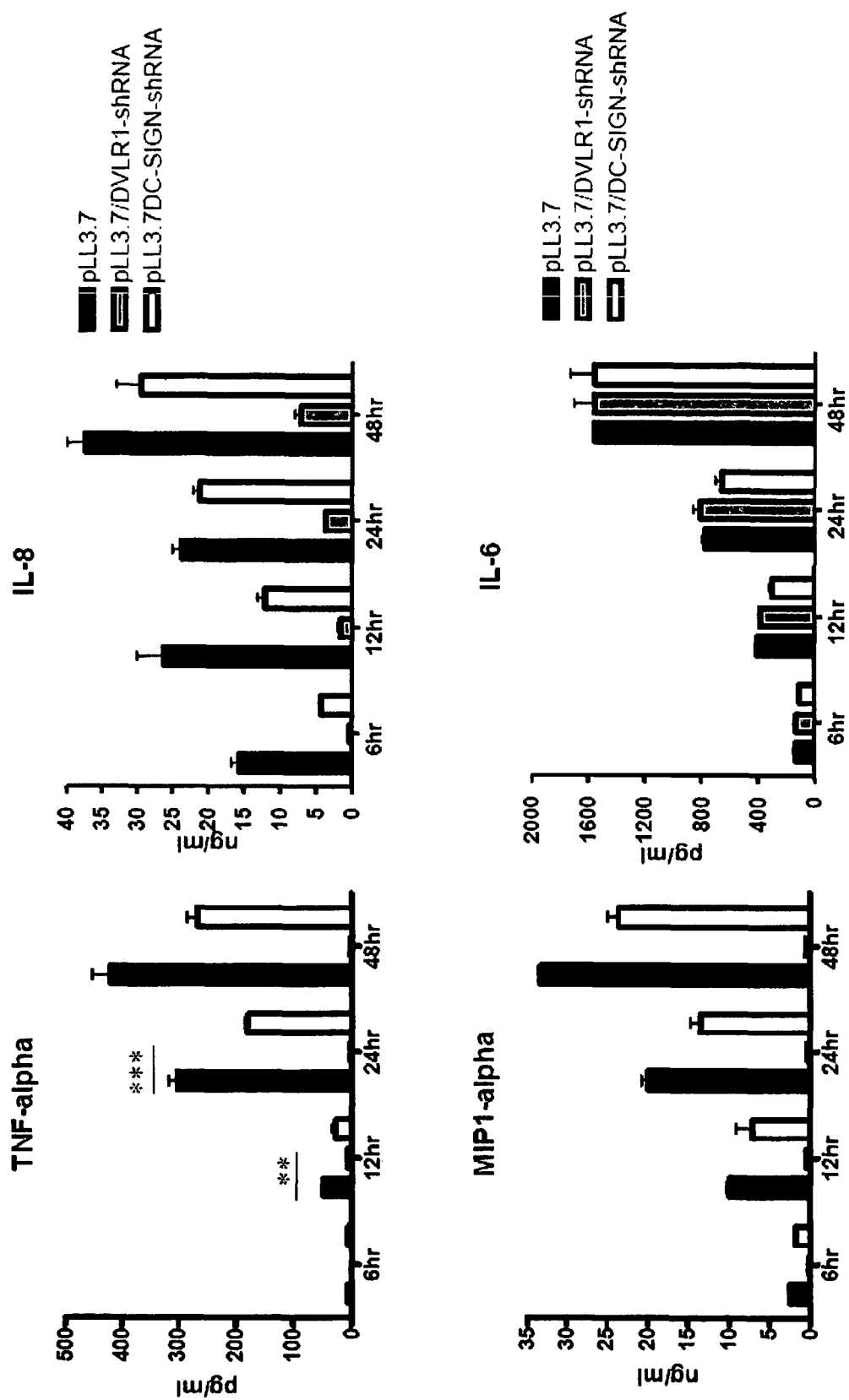
FIG. 14A shows a time course analysis of the secretion of various cytokines by CD14+ macrophages that were electroporated with DC-SIGN-shRNA, DVLR1/CLEC5A-shRNA, or vector controls prior to infection with Dengue virus at t=0.
Figure 14B:
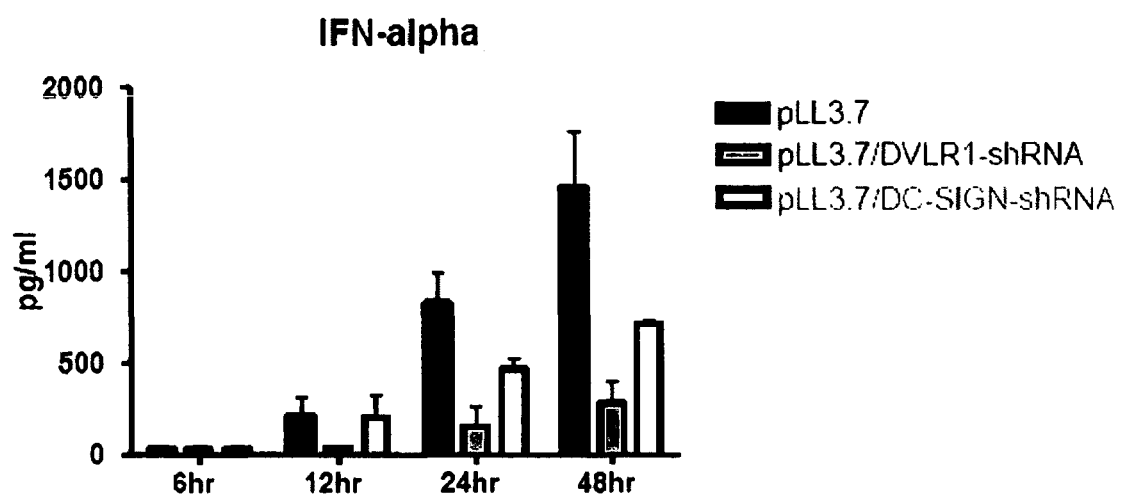
FIG. 14B shows a time course analysis for the cytokine IFN-α under the same conditions.

DVLR1/CLEC5A is Involved in DV-Induced Proinflammatory Cytokine Release from CD14+ Macrophages The cytokine release profile for CD14+ macrophages infected with DV (MOI=5) was evaluated using ELISA after knock down of DVLR1/CLEC5A and DC-SIGN according to the methods of the preceding examples (2.5 h transfection). In the first 12 h, DC-SIGN-shRNA did not affect the secretion of TNF-α, MIP-1α, IFN-α, IL-6, or IL-8. See FIG. 14A-B (error bars represent the standard error from the mean of triplicates, and asterisks indicate statistically significant differences compared to control experiments; $*=p<0.05$; $=p<0.01$; $*=p<0.001$). After 48 h, DC-SIGN-shRNA had a mild inhibitory effect (less than 20%) on TNF-α, MIP-1α, IFN-α, and IL-6 secretion; IL-8 secretion was not affected. Since DC-SIGN is involved in virus entry and replication, this observation suggests that initial cytokine secretion (first 12 h) is independent of DV replication. In contrast, knock down of DVLR1/CLEC5A dramatically suppressed (p<0.005) the secretion of TNF-α, MIP-1α, IFN-α, IL-8, but not of IL-6. This suggests that DVLR1/CLEC5A is responsible for DV-induced cytokine release from CD14+ macrophages. Accordingly, therapeutic agents that prevent the binding of DV to DVLR1/CLEC5A will be useful for preventing the deleterious effects of DV-induced cytokine release in humans. For example, monoclonal antibodies that prevent DVLR1/CLEC5A interaction with DV will be useful for preventing or treating DV-induced Dengue shock syndrome (DSS) or Dengue haemorrhagic fever (DHF).

Example 15

Antagonistic Anti-DVLR1/CLEC5A Monoclonal Antibodies (mAbs) Abolish Inflammatory Cytokine Release By DV Serotypes 1, 2, 3, and 4

Figure 15:
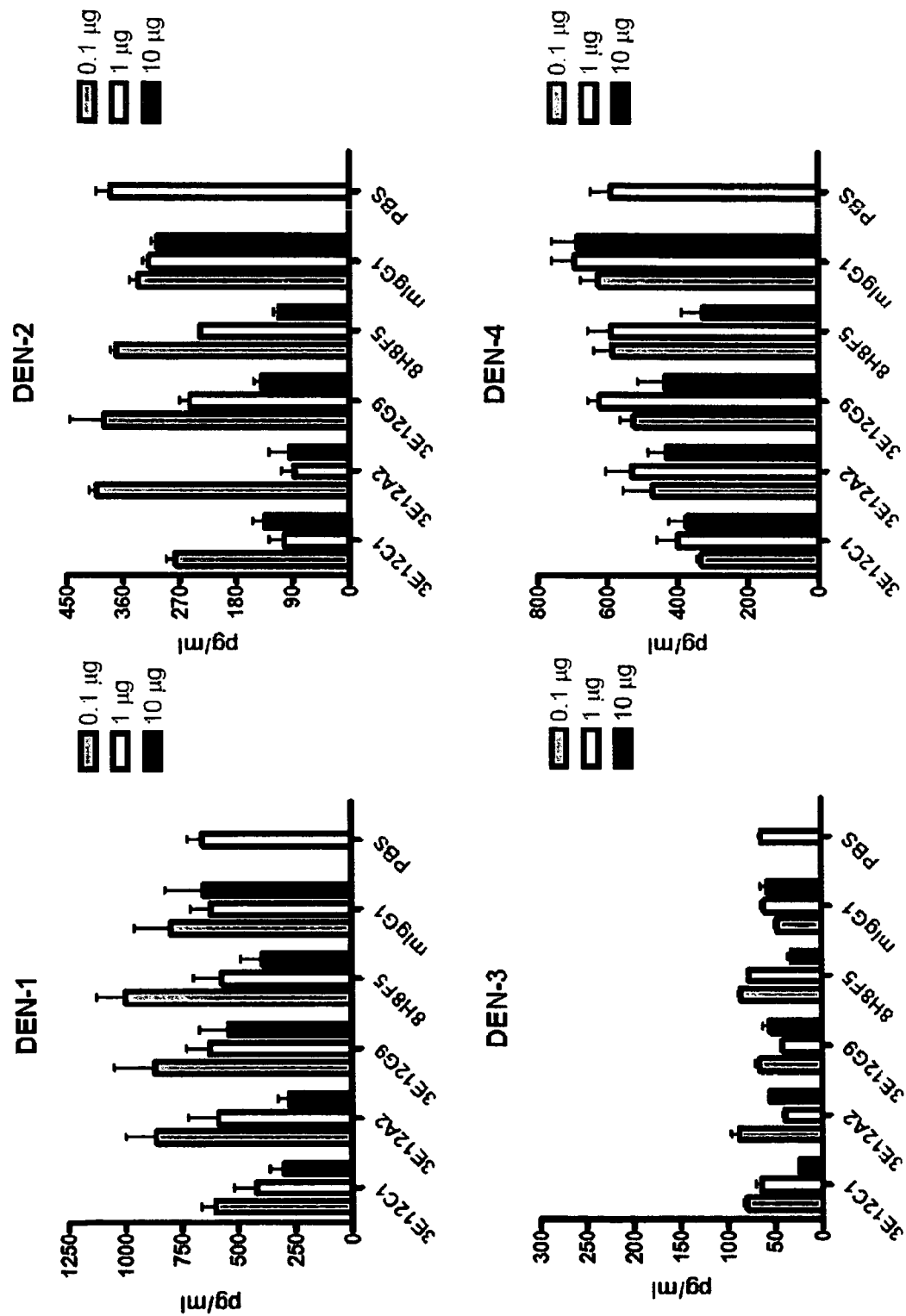
FIG. 15 shows ELISA measurements of TNF-α secreted into culture supernatants by CD14+ macrophages infected with Dengue virus and treated with the specified monoclonal antibody against DVLR1/CLEC5A at the specified concentrations.

Monoclonal antibodies against DVLR1/CLEC5A were generated using standard techniques. Briefly, mice were immunized with DVLR-1.Fc fusion protein, and hybridomas were formed by fusing spienocytes from the mice with P3/NSI/1-Ag4-1 [NS-1] myeloma cells (ATCC TIB-18). Among the mAbs generated, clone 9B12, the subclones of 3E12 (clones 3E12A2, 3E12C1, 3E12G9), and clone 8H8F5 suppressed TNF-α release from macrophages after infection with DEN1 (strain 766733A), DEN2 (strain PL046), DEN3 (strain H-87), and DEN4 (strain 866146A) in a dose-dependent manner. See FIG. 15 which shows ELISA measurements of TNF-α secreted into culture supernatants by CD14+ macrophages infected with DV. In accordance with standard nomenclature, each antibody is referred to via the clone number of the hybridoma that secretes it. Hence, the disclosure also provides the hybridomas that secrete the abovementioned monoclonal antibodies.

The results demonstrate that anti-DVLR1/CLEC5A antibodies will serve as useful therapeutic agents for preventing proinflammatory cytokine release from DV-infected CD14+ macrophages in humans. In particular, but not exclusively, the monoclonal antibodies of this Example, or fragments thereof, or antibodies (or fragments thereof) that bind to the same epitopes as the antibodies of this Example, may be formulated as pharmaceutical compositions and then administered for the treatment or prophylaxis of DV infection in humans, according to the methods provided herein.

Example 16

Determination of Pattern Recognization Receptors (PRRs) on Immune Cells that are Activated by Dengue Virus Dendritic cells (DCs) and macrophages are the primary targets of DV infections (Halstead et al., J. Exp. Med. 1977, 146:201-217; Palucka, Nat. Med. 2000, 6:748-749; Wu et al., Nat. Med. 2000, 6:816-820). While infected DCs undergo apoptosis (despite the secretion of proinflammatory cytokines by bystander DCs) (Palmer et al., J. Virol. 2005, 79, 2432 2439), infected macrophages survive for at least 45 days and secrete multiple cytokines and chemokines from 6 h post-infection (Chen et al., J. Virol. 2002, 76:9877-9887). This suggests that macrophages are the major source of proinflammatory cytokines following DV infection, where virions might trigger inflammatory reactions by activating pattern recognition receptors (PRRs). Toll-like receptors (TLRs), C-type lectins and immunoglobulin-like (Ig-like) receptors (e.g., TREMs and TREM-like receptors (TLT)) have been implicated as potential PRRs (Cook et al., Nat. Immunol. 2004, 5, 975 979; Klesney-Tait et al., Nat. Immunol. 2006, 7, 1266 1273; Robinson et al., Nat. Immunol. 2006, 7, 1258 1265) in this context.

To determine whether dengue virus binds to and activates candidate PRRs on immune cells, twenty-two fusion proteins were expressed in mammalian cells and screened for their interaction with DV2 (Table 2). The fusion proteins comprised the human IgG1.Fc fragment in combination with the extracellular domains of C-type lectins and Ig-like receptors. Gene Aliase Forward primer Reverse primer

TABLE 2

Construction of recombinant receptor.Fc fusion proteins.

| Gene Symbol | Aliases | Forward primer | Reverse primer |
|---|---|---|---|
| CLEC1A | CLEC1 | GGATCCTTTCAGTACTACCAGCTCTCC (SEQ ID NO: 40) | GAATTCTCAGTCACCTTCGCCTAATGT (SEQ ID NO: 2) |
| CLEC1B | CLEC2 | GGATCCCTGGGGATTTGGTCTGTC (SEQ ID NO: 3) | GAATTCTTAAGGTAGTTGGTCCAC (SEQ ID NO: 4) |
| CLEC2B | AICL | GGATCCTCTCAGAGTTTATGCCCC (SEQ ID NO: 5) | GGATCCCCCCATTATCTTAGACAT (SEQ ID NO: 6) |
| CLEC4A | DCIR | GGATCCTTTCAAAAATATTCTCAGCTTCTT (SEQ ID NO: 7) | GAATTCTCATAAGTGGATCTTCATCATC (SEQ ID NO: 8) |
| CLEC4C | BDCA2 | GGATCCTTTATGTATAGCAAAACTGTCAAG (SEQ ID NO: 9) | GAATTCTTATATGTAGATCTTCTTCATCTT (SEQ ID NO: 10) |
| CLEC4D | CLEC6 | GGATCCCATCACAACTTTTCACGCTGT (SEQ ID NO: 41) | GAATTCCTAGTTCAATGTTGTTCCAGG (SEQ ID NO: 12) |
| CLEC4E | Mincle | GAAGATCTACATTTCGCATCTTTCAAACC (SEQ ID NO: 13) | GAATTCCTAGTTCAATGTTGTTCCAGG (SEQ ID NO: 42) |
| CLEC4F | KCLR | AGATCTACAGCAGACAAGACCTG (SEQ ID NO: 43) | AGATCTAGCGCCAGGAGCCCTCTG (SEQ ID NO: 44) |
| CLEC4K | Langerin | GGATCCCGGTTTATGGGCACCATA (SEQ ID NO: 17) | GGATCCTCACGGTTCTGATGGGAC (SEQ ID NO: 18) |
| CLEC4L | DC-SIGN | GGATCCAAGGTCCCCAGCTCCATAAG (SEQ ID NO: 19) | GAATTCCTACGCAGGAGGGGGGT (SEQ ID NO: 20) |
| CLEC4M | DC-SIGNR | GGATCCAAGGTCCCCAGCTCCCTAA (SEQ ID NO: 45) | GAATTCCTATTCGTCTCTGAAGCAGG (SEQ ID NO: 22) |

TABLE 2-continued

Construction of recombinant receptor.Fc fusion proteins.

| Gene Symbol | Aliases | Forward primer | Reverse primer |
|---|---|---|---|
| DVLR1/ CLEC5A | MDL-1 | AGATCTAGTAACGATGGTTTCACCAC (SEQ ID NO: 23) | GAATTCCTGTGATCATTTGGCATTCTT (SEQ ID NO: 24) |
| CLEC6A | Dectin-2 | GGATCCACATATGGTGAAACTGGC (SEQ ID NO: 25) | GGATCCAGCTTCTACTCATAGGTA (SEQ ID NO: 26) |
| CLEC7A | Dectin-1 | GGATCCACCATGGCTATTTGGAGATCC (SEQ ID NO: 27) | GAATTCTTACATTGAAAACTTCTTCTCAC (SEQ ID NO: 46) |
| CLEC10A | HML2 | GGATCCTCCAAATTTCAGAGGGACCTG (SEQ ID NO: 29) | GAATTCTCAGTGACTCTCCTGGCTG (SEQ ID NO: 30) |
| CLEC12A | CLL-1 | GGATCCGTAACTTTGAAGATAGAAATGAAA (SEQ ID NO: 31) | GAATTCTCATGCCTCCCTAAAATATGTA (SEQ ID NO: 47) |
| CLEC13B | DEC-205 | GCCCAGTGCACCTACTATAG (SEQ ID NO: 48) | GTGCACTGGGCCTGTCTGGGTCC (SEQ ID NO: 49) |
| NKG2D | | GGAGTGCTGTATTCCTAAAC (SEQ ID NO: 50) | GAATTCCTGGCTTTTATTGAGATGG (SEQ ID NO: 51) |
| TREM1 | | GAAGGATGAGGAAGACCAGGC (SEQ ID NO: 52) | CATCGGCAGTTGACTTGGGTG (SEQ ID NO: 53) |
| TREM2 | | AGGGTGGCATGGAGCCTCTC (SEQ ID NO: 54) | GAATTCCACATGGGCATCCTCGAA (SEQ ID NO: 55) |
| TLT1 | | CAGCCATGGGCCTCACCCTG (SEQ ID NO: 56) | GAATTCCTGGCTGGGTTCCAAAGGG (SEQ ID NO: 57) |
| TLT2 | | GAATTCCTGGCTGGGTTCCAAAGGG (SEQ ID NO: 58) | GAATTCCTGGTGCCTGATGGAGGGC (SEQ ID NO: 59) |

As shown in FIG. 16, DV interacts with DLVR1/CLEC5A. Specifically, FIG. 16a shows the interaction of DV ($5 \times 10^6$ PFU) with receptor.Fc (1 μg) determined by ELISA. In FIG. 16b, complexes of DV ($5 \times 10^6$ PFU) with receptor.Fc (5 μg) were immunoprecipitated and detected on westerns with mAb to DV envelope (E) protein. FIG. 16c shows the inhibition of DVLR1/CLEC5A-DV interaction by EDTA (10 mM) as determined by ELISA. FIGS. 16d and 16e show sugar competition assays wherein both DC-SIGN (CLEC4L) and DVLR1/CLEC5A increase DV binding to human 293T cells (FIG. 16d), while addition of sugars inhibits biotinylated DV binding to DC-SIGN- (left panel) or DLVR1/CLEC5A- (right panel) transfected 293T cells in a dose-dependent manner as determined by flow cytometry (FIG. 16e). According to FIG. 16e, MFI represents mean fluorescence intensity. Units (U) for monosaccharide (mannose and fucose) and polysaccharide (mannan) are mM and mg/ml, respectively. FIG. 16f shows the effect of PNGaseF (500 U), DTT (0.1 M), heat (95° C. 5 min), or UV (10 J/cm$^2$) on DVLR1/CLEC5A-DV interaction as measured by ELISA. Data are expressed as the mean±s.d. of three independent experiments. Two-tailed, Student's t-tests were performed.

Among the receptors tested, DC-SIGN has been shown previously to interact with glycans located on the envelope (E) protein of DV (Pokidysheva, E. et al., Cell 124:485-93 (2006)). Using ELISA, DVLR1/CLEC5A.Fc (in addition to DC-SIGN.Fc and DC-SIGNR.Fc) was shown to be able to capture DV2 (FIG. 16a). To confirm the specificity of the interaction between DVLR1/CLEC5A and DV, complexes were immunoprecipitated with protein A sepharose beads and then probed with an anti-DV envelope (anti-E) monoclonal antibody (mAb). E protein was detected in the immunoprecipitates of DC-SIGN.Fc and DVLR1/CLEC5A.Fc, confirming that DVLR1/CLEC5A interacts with the dengue virion (FIG. 16b). However, while the binding of DC-SIGN to DV is Ca$^{++}$-dependent, EDTA (a Ca$^{++}$ chelator) had no effect on the DVLR1/CLEC5A-DV interaction (FIG. 1c). Furthermore, transfection of 293T cells with DC-SIGN and DVLR1/CLEC5A resulted in increased binding of biotinylated DV to the cells (FIG. 1d).

There are two conserved N-linked glycosylation sites at Asn-67 and Asn-153 of E protein (Pokidysheva, E. et al., Cell 124:485-93 (2006)), and the attached glycans (with terminal fucose and mannose) have been implicated in cellular attachment and viral entry (Modis, Y. et al., J. Virol. 79:1223-1231 (2005)). To investigate the participation of glycans in the association of DVLR1/CLEC5A with DV, virions were incubated with fucose, mannose, or mannan; where the last two sugars are the ligands for DC-SIGN (Mitchell et al., J. Biol. Chem. 276: 28939-28945 (2006)). As expected, mannose and mannan caused dose-dependent inhibition of the DC-SIGN-DV interaction (FIG. 16e), while the binding of DVLR1/CLEC5A to DV was significantly reduced in the presence of fucose (p<0.0001) and, to a lesser extent, mannan (p=0.0005) (FIG. 16e). Pre-treatment of DV with PNGaseF also substantially reduced the DVLR1/CLEC5A-DV interaction (FIG. 16f), suggesting that glycans present on the viral E proteins are essential for binding. Heat treatment or dithiothreitol (DTT) were also found to abolish the DVLR1/CLEC5A-DV interaction (FIG. 16f), suggesting that the correct topographical distribution of glycans on the dengue virion is important.

Example 17

Interaction of DC-SIGN and DVLR1/CLEC5A with Dengue Virus

Figure 17:
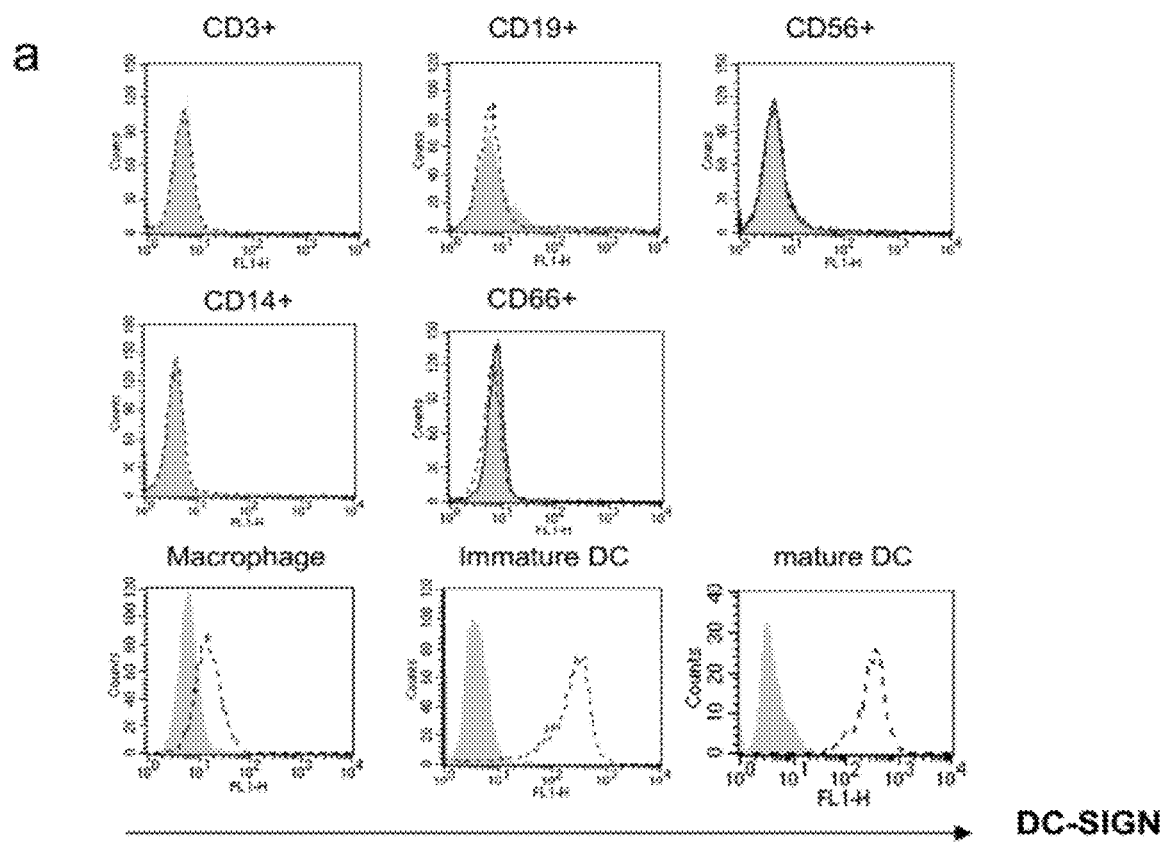
Figure 17:
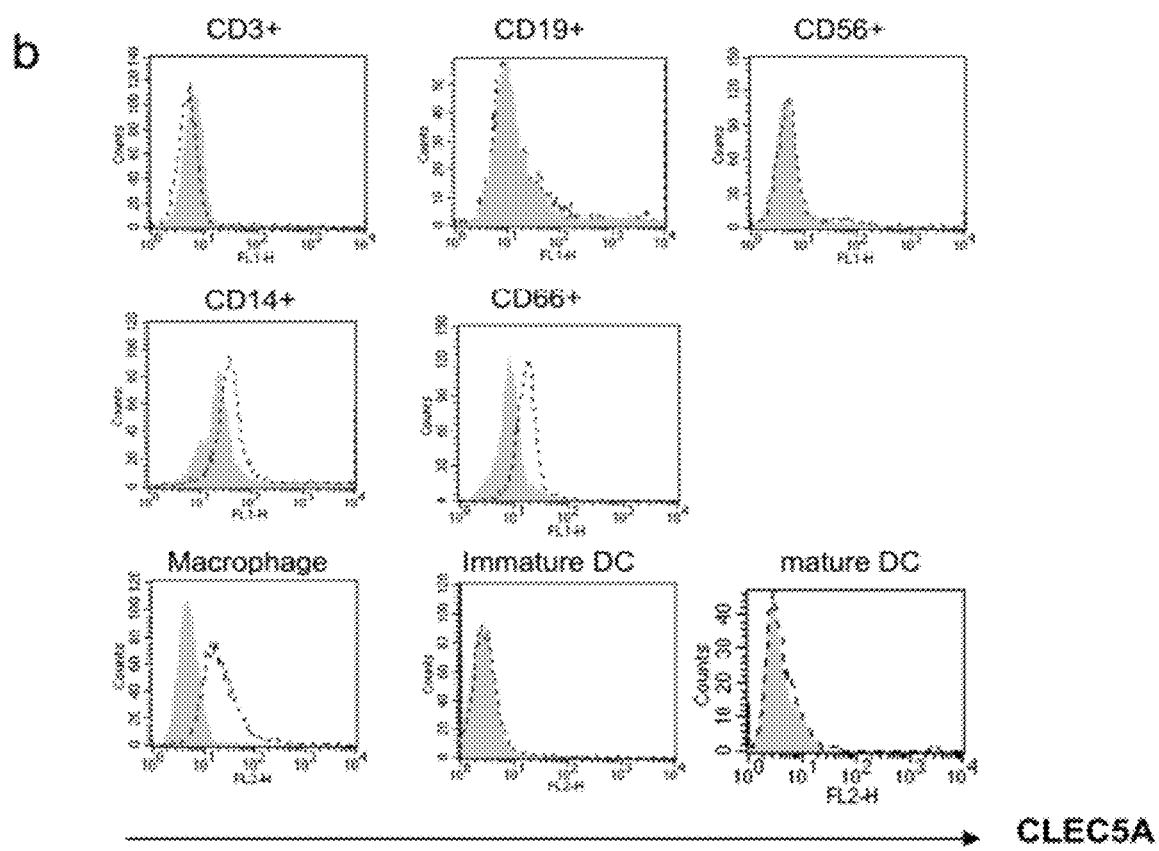

FIG. 17 shows the expression patterns of DC-SIGN and DVLR1/CLEC5A in human PBMCs. Freshly isolated PBMCs were double stained with PE-conjugated antibodies to CD markers (BD PharMingen) and FITC-conjugated anti-DC-SIGNmAb, according to embodiments shown in FIG. 17a or FITC-conjugated anti-DVLR1/CLEC5A mAb (R&D Systems) according to embodiments shown in FIG. 17b. CD marker-positive cells were gated to determine the expression of DC-SIGN and DVLR1/CLEC5A (dashed lines). Shaded areas represent isotype controls.

DC-SIGN, which is expressed on DCs and macrophages (FIG. 17a), contains three motifs in its cytoplasmic tail that are believed to be involved in either endocytosis or intracellular trafficking (Lozach et al., J. Biol. Chem. 2005, 280, 23698 23708). In contrast, DVLR1/CLEC5A was originally identified as DAP12-associated molecule expressed exclusively on monocytes and macrophages (FIG. 17b), although its ligand(s) and biological functions remain to be determined (Bakker et al., Proc. Natl. Acad. Sci. USA 1999, 96, 9792 9796).

Example 18

DVLR1/CLEC5A is Essential for DV-Induced DAP12 Phosphorylation, but not for Dengue Virus Replication According to embodiments illustrated in FIG. 18, DLVR1/CLEC5A is essential for DV-induced DAP12 phosphorylation, but not for DV replication. Specifically, in FIG. 18a, DV-induced DAP12 phosphorylation (2 h p.i.) in human macrophages was determined using antibodies to phosphotyrosine and DAP12 on western blots. FIG. 18b illustrates the kinetics of DAP12 phosphorylation induced by DV and UV-inactivated DV (UV-DV). FIG. 17c illustrates the ability of shRNAs to knock down the expression of DVLR1/CLEC5A and DC-SIGN and to inhibit DV-mediated (m.o.i.=5) DAP12 phosphorylation. FIG. 18d shows the effects of shRNAs on DV entry and replication in macrophages as determined by flow cytometry. FIG. 18e illustrates the effects of anti-DVLR1/CLEC5A. mAb, anti-DC-SIGN mAb, and mouse IgG (50 µg/ml) on the expression of nonstructural protein NS3 (red; Cy3 labeled) examined by confocal microscope (Tassaneetrithep, B. et al., J Exp Med 197: 823-29 (2003)). Cells were counter stained with Hoechst 33342 (blue). In both FIG. 18d and FIG. 18e, macrophages were infected with DV (m.o.i.=5) to determine NS3 expression at 48 h post-infection. FIG. 18f shows the effect of shRNAs on the DV titers of infected macrophages.

Infection of macrophages with DV was found to induce DAP12 phosphorylation in a dose-dependent manner (FIG. 18a). DAP12 phosphorylation peaked at 12 h post-infection (p.i.) and persisted for at least 48 h in the presence of live DV, while UV-inactivated dengue virus (UV-DV) triggered only limited DAP12 phosphorylation that lasted for just 12 h (FIG. 18b), indicating that DAP12 phosphorylation is independent of DV replication during the first 2-6 h of infection. Knockdown of DVLR1/CLEC5A (using the shRNA pLL3.7/DVLR1/CLEC5A), but not that of DC-SIGN (by pLL3.7/DC-SIGN), caused a substantial reduction in DAP12 phosphorylation (FIG. 18c), suggesting that DV-triggered DAP12 phosphorylation is mediated via DVLR1/CLEC5A.

It is known that DC-SIGN participates in the infection of DCs by DV (Navarro-Sanchez et al., EMBO Rep. 4:723-28 (2003); Tassaneetrithep et al., J. Exp. Med. 197:823-829 (2003)). Therefore, DVLR1/CLEC5A was tested as to whether it is involved in DV entry into macrophages by monitoring the expression of DV nonstructural protein 3 (NS3), which is expressed when DV replicates in macrophages. In contrast to DC-SIGN, knockdown of DVLR1/CLEC5A by shRNA (FIG. 18d) or blocking of the DVLR1/CLEC5A-DV interaction with anti-DVLR1/CLEC5A Ab (FIG. 18e) did not inhibit NS3 expression in macrophages as examined by flow cytometry and confocal microscopy, respectively. The shRNA pLL3.7/DVLR1/CLEC5A also failed to suppress the release of dengue virions into the supernatant of infected macrophages, as determined by the plaque-forming assay (FIG. 18f). These results indicate that, while DC-SIGN mediates DV infection and replication, the interaction of DV with DVLR1/CLEC5A triggers cell signaling.

Example 19

Inhibition of DVLR1/CLEC5A-Dengue Virus Interaction Suppresses Inflammatory Response by Infected Macrophages Without Affecting Viral Clearance Response To determine whether DVLR1/CLEC5A is involved in DV-induced inflammation, the secretion of inflammatory cytokines by macrophages, following infection with DV, was examined.

According to embodiments illustrated in FIG. 19, DVLR1/CLEC5A is critical for DV-mediated TNF-α, but not IFN-α, secretion. More specifically, FIG. 19a illustrates the dose-dependency of DV and UV-DV induced TNF-α secretion by macrophages measured by ELISA at 6 h and 12 h p.i. FIG. 19b illustrates the kinetics of TNF-α expression after DV infection (m.o.i.=5). FIG. 19c illustrates the effects of DVLR1/CLEC5A and DC-SIGN shRNAs on the secretion of TNF-α, IL-6, MIP1-α, IL-8, IP-10, and IFN-α from DV-infected macrophages (m.o.i.=5). In FIG. 19d, knockdown experiments with receptor specific shRNAs illustrating that DV-induced IFN-α secretion is via the TLR7-MyD88 pathway and TNF-α secretion is via DVLR1/CLEC5A-TLR7-MyD88 pathway. FIG. 19e illustrates antagonistic anti-DVLR1/CLEC5A mAbs inhibiting TNF-α secretion in response to DV serotypes 1-4 is inhibited (see Table 3).

TABLE 3

Characteristics of anti-human DVLR1/CLEC5A mAbs.

| Clone | Iso-type | ELISA | W.B. | FACS | Antagonistic DV1 | DV2 | DV3 | DV4 | Agonistic |
|---|---|---|---|---|---|---|---|---|---|
| 3E12C1 | IgG1 | + | + | + | ** | ** | ** | * | − |
| 3E12A2 | IgG1 | + | + | + | ** | ** | ** | * | − |

TABLE 3-continued

Characteristics of anti-human DVLR1/CLEC5A mAbs.

| Clone | Iso-type | ELISA | W.B. | FACS | Antagonistic DV1 | DV2 | DV3 | DV4 | Agonistic |
|---|---|---|---|---|---|---|---|---|---|
| 3E12G9 | IgG1 | + | + | + | − | ** | ** | − | − |
| 8H8F5 | IgG1 | + | + | + | * | *** | ** | * | − |
| 2H11 | IgM | + | − | + | − | − | − | − | + |
| 9B12H4 | IgM | + | − | + | *** | *** | − | − | − |

"*" - p < 0.05;
"**" - p < 0.01;
"***" - p < 0.001.

Antibodies (10 μg/sample) that can suppress DV-induced TNF-α secretion from human macrophages. Two-tailed Student's t-tests were performed and data were compared with each appropriate isotype control antibody. An antibody that can trigger TNF-α secretion from human macrophages (compared with isotype control) is defined as agonistic. The specificity was confirmed by abolition of TNF-α secretion using pLL3.7/DVLR1/CLEC5A-shRNA (pLL3.7 vector and pLL3.7/DC-SIGN had no effect on antibody mediated TNF-α secretion. ELISA, Enzyme-Linked Immuno Sorbent Assay; WB, western blotting; FACS, Fluorescence Activated Cell Sorting. Antibodies are azide-free, sterile-filtered, and with endotoxin level less than 0.1EU per micrograms.

M.R. mAb (anti-mannose receptor mAb; mIgG1) and murine IgM (mIgM) were used as negative controls. In both FIG. 19d and FIG. 19e, macrophages were infected with DV (m.o.i.=5) and harvested at 36 h p.i. for cytokine assays. Data are expressed as mean±s.d. of three independent experiments (using material from at least three different donors). Two-tailed, Student's t-tests were performed. "ND" represents not detected.

At 6 h p.i., dose-dependent secretion of TNF-α was detected, where similar levels of cytokine were secreted by macrophages infected with either DV or UV-DV (FIG. 19a, left panel). However, at 12 h p.i., TNF-α secretion was further increased by DV, but not by UV-DV (FIG. 19a, right panel). Over a 48 h time course, TNF-α secretion continually increased for macrophages infected with DV, while at 24 h-48 h post-infection with UV-DV this cytokine was barely detectable (FIG. 19b). These data are in accord with the kinetics of DAP12 phosphorylation (FIG. 18b), suggesting that DV-mediated TNF-α secretion is related to DAP12 activation. It was also observed that knockdown of DVLR1/CLEC5A suppressed the release of TNF-α, IL-6, IL-8, MIP1-α, and IP-10 by DV-infected macrophages to a greater extent than knockdown of DC-SIGN (FIG. 19c). However, while pLL3.7/DC-SIGN mildly suppressed IFN-α secretion (p=0.048), pLL3.7/DVLR1/CLEC5A had no effect on IFN-α (FIG. 19c).

To further understand the DV-activated signaling pathways leading to cytokine secretion, macrophages were transfected with shRNAs to knock down DVLR1/CLEC5A, DC-SIGN, TLR4, TLR7 or MyD88, prior to DV infection. The data obtained indicate that DV-induced IFN-α secretion occurs via the TLR7-MyD88 pathway (p=0.0016), while TNF-α secretion is mediated through both DVLR1/CLEC5A (p=0.003) and TLR7-MyD88 (p=0.013) (FIG. 19d). A panel of anti-DVLR1/CLEC5A mAbs was generated, with differential antagonistic effects on the four serotypes of DV (see Table 3 above) as determined by inhibition of TNF-α secretion from DV-infected macrophages (FIG. 3e). These data indicate that, although different epitopes of DVLR1/CLEC5A appear to mediate the individual interactions, antibodies that inhibit the DVLR1/CLEC5A-DV interaction can suppress the inflammatory response by macrophages infected with the relevant DV serotype(s). The differential antagonistic effects of anti-DVLR1/CLEC5A mAbs might relate to the fact that each DV serotype binds to distinct epitope of DVLR1/CLEC5A, and anti-DVLR1/CLEC5A mAb can inhibit the binding of specific DV serotype whose binding site overlaps with that of anti-DVLR1/CLEC5A mAb.

Example 20

Antibody-Dependent Enhancement (ADE) Mediated IFN-α Secretion is Independent of DVLR1/CLEC5A It has been demonstrated previously that non-neutralizing anti-DV Abs promote DV entry into target cells via FcR receptors and, thereby, enhance cytokine release (Halstead et al., J. Exp. Med. 146:201-217 (1977); Goncalvez et al., Proc Natl Acad Sci USA 104:9422-9427 (2007)), a phenomenon termed antibody-dependent enhancement (ADE) of infection. For example, anti-prM and anti-E mAb have been shown to induce this effect in vitro (Huang et al., J Immuno 176: 2825-2832 (2006)). Here, investigation was conducted regarding whether blockade of the DVLR1/CLEC5A-DV interaction can inhibit ADE.

Figure 20:
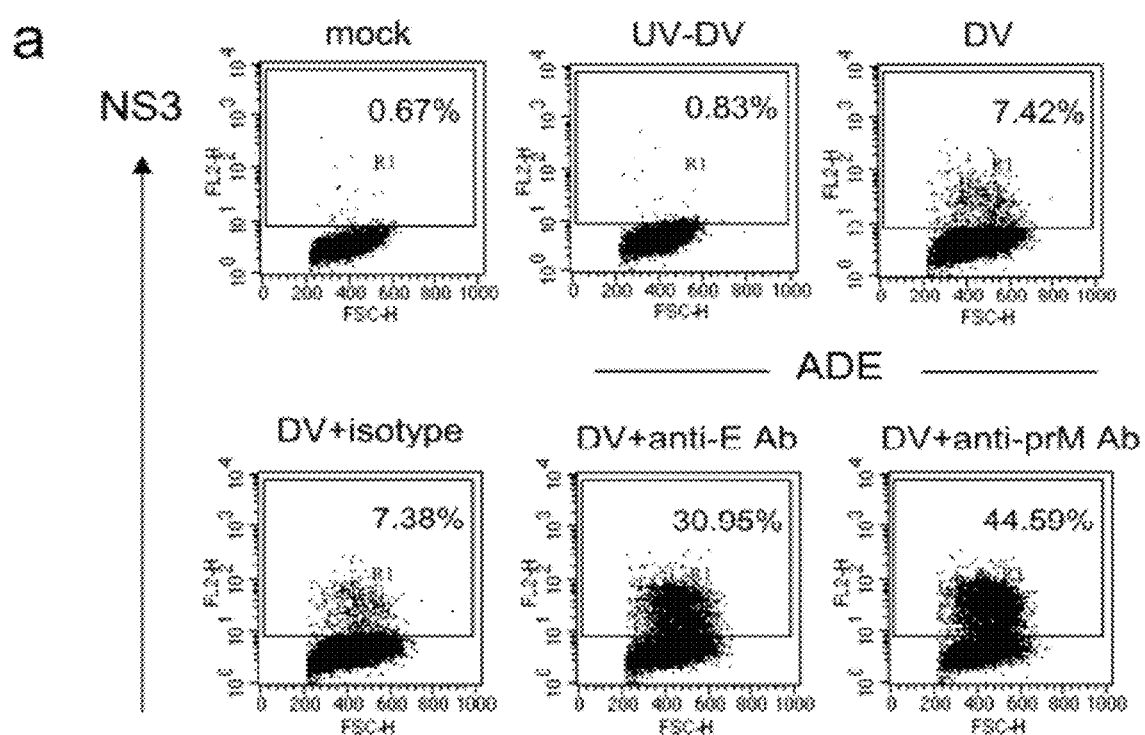

As according to embodiments illustrated in FIG. 20, DLVR1/CLEC5A is critical for ADE-mediated secretion of TNF-α but not IFN-α. More specifically, in FIG. 20a macrophages were infected with DV (m.o.i.=5), DV/anti-E or DV/anti-prM immunocomplexes (ADE) for 36 h, followed by the detection of DV replication by anti-NS3 mAb. Macrophages from 10 individuals were infected with DV2 (FIG. 20b) or DV/anti-prM or DV/anti-E complexes (FIG. 20c), in the presence of antagonistic anti-DVLR1/CLEC5A mAb (1 μg; clone 9B12H4) or isotype control. TNF-α and IFN-α secretion were determined by ELISA. Two-tailed, Student's t-tests were performed.

Primary human macrophages were infected with DV alone or with anti-prM/DV or anti-E/DV immunocomplexes, in the presence of anti-DVLR1/CLEC5A mAb (or isotype control) for 36 h. Anti-prM/DV and anti-E/DV immunocomplexes (ADE) were found to increase the expression of NS3 (FIG. 20a) and the levels of TNF-α and IFN-α secretion as compared to DV alone (FIGS. 20b and 20c). However, while the anti-DVLR1/CLEC5A mAb significantly inhibited TNF-α release from macrophages infected with DV, anti-prM/DV and anti-E/DV immunocomplexes (FIG. 20c), IFN-α secretion was not affected, suggesting that ADE-mediated IFN-α secretion is independent of DVLR1/CLEC5A (as noted above for DV-induced IFN-α production).

Example 21

Involvement of DVLR1/CLEC5A in Dengue-Virus Induced Vascular Leakage

The hallmarks of DHF and DSS are plasma leakage together with subcutaneous and vital organ hemorrhaging.

These symptoms are caused by the numerous soluble mediators and cytokines released by immune cells to increase vascular permeability (Green et al., Curr. Opin. Infect. Dis. 19:429-436 (2006)). To determine whether DVLR1/CLEC5A is involved in DV-induced vascular leakage, monolayers of human dermal microvascular endothelial cells (HMEC-1) were used in a permeability assay (Carr et al., J. Med. Virol. 69:521-528 (2003)).

According to embodiments illustrated in FIG. 21, antagonistic anti-DVLR1/CLEC5A mAbs rescue the permeabilization of endothelial cell monolayers by the supernatants of DV infected macrophages. More specifically, FIG. 21a illustrates changes over time in the permeability of HMEC-1 monolayers determined by measurement of HRP passage following incubation with supernatants from macrophages infected with DV or DV/anti-prM complexes (ADE). TNF-α levels in the supernatants were measured by ELISA. As illustrated in FIG. 21b, the inhibitory effects of TNFR2.Fc (5 μg/ml) and anti-DVLR1/CLEC5A (clone 9B12H4, 5 μg/ml) on permeabilization of endothelial monolayers were determined. Data are expressed as mean±s.d. of three independent experiments. Two-tailed, Student's t-tests were performed.

Supernatants from macrophages infected with DV or anti-prM/DV immunocomplexes were found to induce permeability in HMEC-1 monolayers; where the immunocomplexes (ADE) produced a more significant effect than DV alone, during the first 36 h-48 h of infection (FIG. 21a, left). Interestingly, the changes in permeability do not correlate with TNF-α levels in the supernatants (FIG. 21a, right). Furthermore, while neutralization of TNF-α by recombinant TNFR2.Fc was able to partially inhibit the induction of permeability triggered by DV or anti-prM/DV ($p<0.05$) (FIG. 21b), the anti-DVLR1/CLEC5A mAb was more effective in this respect (FIG. 21b). It was observed that anti-DVLR1/CLEC5A blocked the secretion of other inflammatory cytokines by macrophages, in addition to TNF-α (FIG. 19c), might explain this phenomenon.

Example 22

Dose-Dependent Interaction Between Antagonistic Mabs and Dengue-Virus Induced TNF-α Secretion Further investigation was conducted on whether blockade of the DV-CLEC5A interaction can rescue mice from DV-induced lethality in vivo. According to embodiments illustrated in FIG. 22, the interaction of mDVLR1/CLEC5A and DV (FIG. 22a) and expression pattern of mDVLR1/CLEC5A in murine cells (FIGS. 22b and 22c) is shown. More specifically, FIG. 22a shows the interaction of DV ($5\times10^6$ PFU) with human and murine DVLR1/CLEC5A.Fc (1 μg) determined by ELISA. F4/80 and CD marker-positive cells were gated to determine the expression of mDVLR1/CLEC5A in murine splenocytes (FIG. 22b), murine bone marrow (BM)-derived macrophage and the murine macrophage cell line Raw264.7 (FIG. 22c).

It was found that murine DVLR1/CLEC5A (mDVLR1/CLEC5A) binds DV with a similar affinity as human DVLR1/CLEC5A (FIG. 22a), and mDVLR1/CLEC5A is expressed on myeloid lineages (CD11b+, F4/80+), bone marrow derived macrophages, and murine macrophage-like Raw264.7 cells (FIGS. 22b and 22c).

Example 23

Blockade of mDVLR1/CLEC5A-DV Interaction Suppresses DV-Induced TNF-α Secretion from Raw264.7 Cells According to embodiments illustrated in FIG. 23, blockade of mDVLR1/CLEC5A-DV interaction suppresses DV-induced TNF-α secretion from Raw264.7 cells. More specifically, FIG. 23a shows that human DC-SIGN increased DV binding to the murine macrophage cell line Raw264.7 and enhanced the stimulatory effect of DV infection. TNF-α release was determined by ELISA. FIG. 23b shows the identification of antagonistic mAbs to murine DVLR1/CLEC5A. Raw264.7 cells stably expressing human DC-SIGN were incubated with DV2 (PL046; m.o.i.=30) in the presence of mAbs. TNF-α levels in supernatants (at 48 h p.i.) were determined by ELISA. FIG. 23c shows that anti-mDVLR1/CLEC5A mAbs (clone: 3D2H6 and 10D7H3) inhibit DV2-(NGC-N; m.o.i.=30) induced TNF-α release in a dose-dependent manner. mIgG1 acts as an isotype-matched negative control.

DV stimulated Raw264.7 cells stably expressing human DC-SIGN (Raw264.7/DC-SIGN) to secrete TNF-α (FIG. 23a), and blockade of mDVLR1/CLEC5A-DV interaction by antagonistic mAbs (Table 4) abolished DV-induced TNF-α secretion by Raw264.7/DC-SIGN cells in a dose-dependent manner (FIGS. 23b and 23c).

TABLE 4

Characteristics of anti-murine DVLR1/CLEC5A mAbs.

| Clone | Isotype | ELISA | FACS | Antagonistic effect DV2 | DV2 (NGC-N) |
|---|---|---|---|---|---|
| 3D2H6 | IgG1 | + | + | * | ** |
| 9D8E9 | IgG1 | + | ND | * | ND |
| 9D9F9 | IgG1 | + | ND | − | ND |
| 1A10F9 | IgG1 | + | ND | − | ND |
| 10D7G4 | IgG1 | + | ND | − | ND |
| 10D7H3 | IgG1 | + | + | * | * |

"*" - $p<0.05$;
"**" - $p<0.01$;
"ND" - not done.
Antibodies that suppress DV-induced TNF-α secretion from murine macrophages cell line RAW264.7/DC-SIGN.
Two-tailed Student's t-tests were performed and data were compared with each appropriate isotype control antibody.
ELISA, Enzyme-Linked Immuno Sorbent Assay;
FACS, Fluorescence Activated Cell Sorting.
Antibodies are azide-free, sterile-filtered, and with endotoxin level less than 0.1EU per micrograms.

Example 24

Dengue Virus (NGC-N) Induces Lethality in STAT1$^{-/-}$ Mice

According to embodiments illustrated in FIG. 24, STAT1$^{-/-}$ mice (n=5/group) were challenged with DV2/PL046 or DV2/NGC-N strain (i.p. and i.c. routes) at a range of doses (from 102 to 105 PFU) for 4 weeks. Data are exhibited as Kaplan-Meier survival curves.

IFN-α functions to inhibit viral replication in both infected and uninfected cells, and IFN-mediated responses to DV infection involve both the STAT1-dependent (essential in the control of viral replication) and STAT1-independent (essential for resolution of infection) pathways (Shresta, et al. J. Immunol. 175:3946-3954 (2005)). Although wild type mice were resistant to DV infection, STAT1-deficient (STAT$^{-/-}$) (Durbin, et al., Cell. 84:443-450 (1996)) mice were sensitive to DV2-9 (strain New Guinea C-N) induced lethality (FIG. 24).

Example 25

Potential Therapeutic Effects of Antagonistic mAbs Against DVLR1/CLEC5A

Further testing was conducted on the potential therapeutic effects of the antagonistic mAbs on STAT1$^{-/-}$ mice. According to embodiments illustrated in FIG. 25, anti-DVLR1/ CLEC5A mAbs prevent DV-induced vascular leakage and lethality in STAT1-deficient mice. More specifically, in FIG. 25a, the mAb 3D2H6 raised against murine DVLR1/ CLEC5A inhibits the subcutaneous and intestinal hemorrhaging of DV-challenged STAT1$^{-/-}$ mice. In FIG. 25b, plasma leakage into the vital organs of DV-challenged STAT-1$^{-/-}$ mice was reduced by mAbs against DVLR1/CLEC5A (3D2H6 and 10D7H3), as determined by Evans blue assay. FIG. 25c illustrates the quantification of vascular permeability by extraction of Evan blue from organs. Data are expressed as the mean±s.d. of three independent experiments: *$p<0.05$; $p<0.01$; *$p<0.001$ (Student's t test). FIG. 25d illustrates the serum levels of TNF-α and IP-10 (n=8; upper and middle) and virus titers (n=4; lower) for DV-challenged STAT11-1 mice at day 7 p.i. in the presence or absence of anti-DVLR1/ CLEC5A mAbs or TNFR2.Fc. Two-tail, Student's t-tests were performed. FIG. 25e illustrates the survival curve of STAT1-deficient mice challenged with DV2 (strain New Guinea C-N, 1×105 PFU/mouse i.p. plus i.c. routes) in the presence of antagonistic anti-murine DVLR1/CLEC5A mAbs or TNFR2.Fc. Data were collected from four independent experiments (17 mice in each group) and exhibited as Kaplan-Meier survival curves with log rank test. p values for significant difference between treatment of DVLR1/ CLEC5A mAb and mouse IgG are indicated.

DV-challenged STAT1-mice exhibited ruffled fur and mild paralysis in addition to subcutaneous and intestinal hemorrhaging at 8 days p.i. (FIG. 25a), and all died within 7-14 days of infection (FIG. 25e). Five doses of Abs (100 μg/mouse, i.p.) or TNFR2.Fc (100 μg/mouse, i.p.) were administered on days 0, 1, 3, 5, and 7 p.i. At 9 days p.i., leakage of Evans blue into the kidney, liver, stomach, small intestine, large intestine, and spleen of DV-challenged mice was significantly reduced in mice treated with anti-mDVLR1/CLEC5A mAbs compared to controls (FIGS. 25b and 25c). Anti-mDVLR1/ CLEC5A mAbs also effectively lowered the serum levels of TNF-α and IP-10 (FIG. 25d, upper and middle), without suppressing viral replication, at day 7 p.i. (FIG. 25d, lower) and protected mice from lethality at day 14 p.i. (70% protection rate). The overall survival rate of anti-mDVLR1/ CLEC5A-treated mice is 48% as observed at day 21 p.i. (FIG. 25e), with DV being cleared from serum of surviving mice at day 23 p.i. (data not shown). Thus, blockade of the DVLR1/ CLEC5A-DV interaction appears to prevent the DV-associated complications of hemorrhaging and plasma leakage, as well as suppressing the macrophage inflammatory response, without impairing virus clearance by the adaptive immune response. In contrast, TNFR2.Fc neither reduced vascular permeability (FIG. 25c) nor protected mice from lethality (FIG. 5e), even though it effectively lowered the serum level of TNF-α (FIG. 25d).

Example 26

DVLR1/CLEC5A is Involved in JEV-Mediated DAP12 Phosphorylation and TNF-α Secretion from Human Macrophages Like with DV, JEV follows a similar virus infection response pattern, which is believed to be the same or similar in all flaviviruses. As illustrated in FIG. 26a, interaction of DVLR1/CLEC5A.Fc. (1 μg), with JEV and DV (5×10$^6$ PFU), respectively, were determined by ELISA. DV interacts with human DVLR1/CLEC5A (187 amino acid in length) SEQ ID NO: 72, but not the alternatively spliced form sDVLR1/ CLEC5A (aa 43-65 is deleted). SEQ ID NO: 73. In contrast, JEV only interacts with sDVLR1/CLEC5A, but not full length DVLR1/CLEC5A. As illustrated in FIG. 26b, DV induces DAP12 phosphorylation (at 2 h p.i.) in human macrophages is shown. DAP12 in DV-infected macrophages were precipitated by anti-DAP12 mAb, blotted to nitrocellulose paper after fractionation on SDS-PAGE, followed by incubation with antibodies against phosphotyrosine and DAP12, respectively. JEV-induced DAP12 phosphorylation (m.o.i.=5) is inhibited by pLL3.7/DVLR1/CLEC5A. As illustrated in FIG. 26c, kinetics of TNF-α secretion from human macrophages in response to JEV infection (left) are shown. JEV-induced TNF-α secretion is inhibited by pLL3.5/ DVLR1/CLEC5A mAb (right). Data are expressed as the mean±s.d. of three independent experiments.

Example 27

Variable Heavy and Light Chain Sequence for mAB 3E12A2

The variable heavy chain sequence for mAb 3E12A2 is shown below (SEQ ID NO: 60):

```
  1  CAGGTGCAGC TCGAGGAGTC AGGACCTGAG CTGGTGAAAC CCGGGGCATC
     AGTGAAGCTG TCCTGCAAGG CTTCTGGCTA CACCTTCACT GAGTATATTA

101  TACACTGGGT AAAGCAGAGG TCTGGACAGG GTCTTGAGTG GATTGGGTGG
     TTTTACCCTG GAAGTGGTAG TATAAAGTAC AATGAGAAAT TCAAGGACAA

201  GGCCACATTG ACTGCGGACA AATCCTCCAG CACAGTCTAT ATGGAGCTTA
     GTGGATTGAC ATCTGAAGAC TCTGCGGTCT ATTTCTGTGC AAGACACGAT

301  GGTTACTCCT ACTTTGACTA CTGGGGCCAA GGCACCACTC TCACAGTCTC
     CTCAGCCAAA ACGACACCCC CATCTGTCTA TCCACTGCC  CCTGGATCTG

401  CTGCCCAAAC TAACTCCATG GTGACCCTGG GATGCCTGGT CAAGGGCTAT
     TTCCCTGAGC CAGTGACAGT GACCTGGAAC TCTGGATCCC TGTCCAGCGG

501  TGTGCACACC TTCCCAGCTG TCCTGCAGTC TGACCTCTAC ACTCTGAGCA
     GCTCAGTGAC TGTCCCCTCC AGCACCTGGC CAGCGAGAC  CGTCACCTGC

601  AACGTTGCCC ACCCGGCCAG CAGCACCAAG GTGGACAAGA AAATTGTGCC
     CAGGGATTGT ACTAGTAAGC CT
```

The variable light chain sequence for mAb 3E12A2 is shown below (SEQ ID NO: 61):

```
  1  CCAGTTCCGA GCTCGTGACA CAGTCTCCAT CCTCCCTGGC TGTGTCAGCA
     GGAGAGAAGG TCACTATGAG CTGCAAATCC AGTCAGAGTC TGCTCAACAG

101  TAGAACCCGA AAGAACTACT TGGCTTGGTA CCAGCAGAAA CCAGGGCAGT
     CTCCTAAACT GCTGATCTAC TGGGCATCCA CTAGGGAATC TGGGGTCCCT

201  GATCGCTTCA CAGGCAGTGG ATCTGGGACA GATTTCACTC TCACCATCAG
     CAGTGTGCAG GCTGAAGACC TGGCAGTTTA TTACTGCAAG CAATCTTATA

301  ATCTGTACAC GTTCGGAGGG GGGACCAAGC TGGAAATAAA ACGGGCTGAT
     GCTGCACCAA CTGTATCCAT CTTCCCACCA TCCAGTGAGC AGTTAACATC

401  TGGAGGTGCC TCAGTCGTGT GCTTCTTGAA CAACTTCTAC CCCAAAGACA
     TCAATGTCAA GTGGAAGATT GATGGCAGTG AACGACAAAA TGGCGTCCTG

501  AACAGTTGGA CTGATCAGGA CAGCAAAGAC AGCACCTACA GCATGAGCAG
     CACCCTCACG TTGACCAAGG ACGAGTATGA ACGACATAAC AGCTATACCT

601  GTGAGGCCAC TCACAAGACA TCAACTTCAC CCATTGTCAA GAGCTTCAAC
     AGGAATGAGT GTTAATTCTA GACGGCGC
```

Example 28

Variable Heavy and Light Chain Sequence for mAb 3E12G9

The variable heavy chain sequence for mAb 3E12G9 is shown below (SEQ ID NO: 62):

```
  1  CAGGTGCAGC TCGAGCAGTC AGGACCTGAG CTGGTGAAAC CCGGGGCATC
     AGTGAAGCTG TCCTGCAAGG CTTCTGGCTA CACCTTCACT GAGTATATTA

101  TACACTGGGT AAAGCAGAGG TCTGGACAGG GTCTTGAGTG GATTGGGTGG
     TTTTACCCTG GAAGTGGTAG TATAAAGTAC AATGAGAAAT TCAAGGACAA

201  GGCCACATTG ACTGCGGACA AATCCTCCAG CACAGTCTAT ATGGAGCTTA
     GTGGATTGAC ATCTGAAGAC TCTGCGGTCT ATTTCTGTGC AAGACACGAT

301  GGTTACTCCT ACTTTGACTA CTGGGGCCAA GGCACCACTC TCACAGTCTC
     CTCAGCCAAA ACGACACCCC CATCTGTCTA TCCACTGGCC CCTGGATCTG

401  CTGCCCAAAC TAACTCCATG GTGACCCTGG GATGCCTGGT CAAGGGCTAT
     TTCCCTGAGC CAGTGACAGT GACCTGGAAC TCTGGATCCC TGTCCAGCGG

501  TGTGCACACC TTCCCAGCTG TCCTGCAGTC TGACCTCTAC ACTCTGACCA
     GCTCAGTGAC TGTCCCCTCC AGCACCTGGC CCAGCGAGAC CGTCACCTGC

601  AACGTTGCCC ACCCGGCCAG CAGCACCAAG GTGGACAAGA AAATTGTGCC
     CAGGGATTGT ACTAGTAAGC CT
```

The variable light chain sequence for mAb 3E12G9 is shown below (SEQ ID NO: 63):

```
  1  CCAGTTCCGA GCTCGTGACA CAGTCTCCAT CCTCCCTGGC TGTGTCAGCA
     GGAGAGAAGG TCACTATGAG CTGCAAATCC AGTCAGAGTC TGCTCAACAG

101  TAGAACCCGA AAGAACTACT TGGCTTGGTA CCAGCAGAAA CCAGGGCAGT
     CTCCTAAACT GCTGATCTAC TGGGCATCCA CTAGGGAATC TGGGGTCCCT

201  GATCGCTTCA CAGGCAGTGG ATCTGGGACA GATTTCACTC TCACCATCAG
     CAGTGTGCAG GCTGAAGACC TGGCAGTTTA TTACTGCAAG CAATCTTATA

301  ATCTGTACAC GTTCGGAGGG GGGACCAAGC TGGAAATAAA ACGGGCTGAT
     GCTGCACCAA CTGTATCCAT CTTCCCACCA TCCAGTGAGC AGTTAACATC

401  TGGAGGTGCC TCAGTCGTGT GCTTCTTGAA CAACTTCTAC CCCAAAGACA
     TCAATGTCAA GTGGAAGATT GATGGCAGTG AACGACAAAA TGGCGTCCTG

501  AACAGTTGGA CTGATCAGGA CAGCAAAGAC AGCACCTACA GCATGAGCAG
     CACCCTCACG TTGACCAAGG ACGAGTATGA ACGACATAAC AGCTATACCT

601  GTGAGGCCAC TCACAAGACA TCAACTTCAC CCATTGTCAA GAGCTTCAAC
     AGGAATGAGT GTTAATTCTA GACGGCGC
```

Example 29

Variable Heavy and Light Chain Sequence for mAb 8H8F5

The variable heavy chain sequence for mAb 8H8F5 is shown below (SEQ ID NO: 64):

```
  1  GAGGTGAAGC TCGAGGAGTC TGGACGAGGC TTAGTGCAGC CTGGAGGGTC
     CCGGAAACTC TCCTGTGCAG CCTCTGGATT CACTTTCAGT ACCTCTGGAA

101  TGAAGGGCCG TGCACTGGGT TCGTCAGGCT CCAGAGAAGG GGCTGGAGTG
     GGTCGCATAC ATTAGTAGTG GCAGCACTAC CATCTACCAT GCAGACACAG

201  ATTCACCATC TCCAGAGACA ATCCCAAGAA CACCCTGTTC CTGCAAATGA
     CCAGTCTAAG GTCTGAGGAC ACGGCCATGT ATTACTGTGC AAGATCGGGT

301  CAGTTTGGTA ACTACTTTGA CTACTGGGGC CAAGGCACCA CTCTCACAGT
     CTCCTCAGCC AAAACGACAC CCCCATCTGT CTATCCACTG CCCCTGGATC

401  TGCTGCCCAA ACTAACTCCA TGGTGACCCT GGGATGCCTG GTCAAGGGCT
     ATTTCCCTGA GCCAGTGACA GTGACCTGGA ACTCTGGATC CCTGTCCAGC

501  GGTGTGCACA CCTTCCCAGC TGTCCTGCAG TCTGACCTCT ACACTCTGAG
     CAGCTCAGTG ACTGTCCCCT CCAGCACCTG GCCCAGCGAG ACCGTCACCT

601  GCAACGTTGC CCACCCGGCC AGCAGCACCA AGGTGGACAA GAAAATTGTG
     CCCAGGGATT GTACTAGTAA GCCT
```

The variable light chain sequence for mAb 8H8F5 is shown below (SEQ ID NO: 65):

```
  1  CCAGATGTGA GCTCGTCATG ACCCAGTCTC CAAAATTCCT GCTTGTATCA
     GCAGGAGACA GGGTTACCCT AACCTGCAAG GCCAGTCAGA GTGTGAATAA

101  TGATGTATAT TGGTACCAAC AGGAGCCAGG TCAGTCTCCT AAACTGCTGA
     TATACTATGC ATCCAATCGC TACACTGGAG TCCCTGATCG CTTCACTGGC

201  AGTGGATATG GGACGGATTT CACTTTCACC ATCAGCACTG TGCAGTCTGA
     AGACCTGGCA GTTTATTTCT GTCAGCACGA TTATAGCTCT CCGTACACGT

301  TCGGAGGGGG GACCAAGCTG GAAATAAAAC GGGCTGATGC TGCACCAACT
     GTATCCATCT TCCCACCATC CAGTGAGCAG TTAACATCTG GAGGTGCCTC

401  AGTCGTGTGC TTCTTGAACA ACTTCTACCC CAAAGACATC AATGTCAAGT
     GGAAGATTGA TGGCAGTGAA CGACAAAATG GCGTCCTGAA CAGTTGGACT

501  GATCAGGACA GCAAAGACAG CACCTACAGC ATGAGCAGCA CCCTCACGTT
     GACCAAGGAC GAGTATGAAC GACATAACAG CTATACCTGT GAGGCCACTC

601  ACAAGACATC AACTTCACCC ATTGTCAAGA GCTTCAACAG GAATGAGTGT
     TAATTCTAGA CGGCGC
```

Example 30

Comparison of Variable Heavy and Light Chain Sequence Alignment for mAb 8H8F5, 3E12A2, and 3E12G9

The comparison of the variable heavy chain alignment for mAb 8H8F5, 3E12A2, and 3E12G9 is shown below (SEQ ID NO: 66, 67, and 68, respectively):

```
              10         20         30 40         50
8H8F5 VH4 (-----ESGRG LVQPGGSRKL SCAASGFTFS TSGMHWVRQA PEKGLEWVAY

3E12A2 VH1 QVQLEESGPE LVKPGASVKL SCKASGYTFT EYIIHWVKQR SGQGLEWIGW

3E12G9 VH9 QVOLEOSGPE LVKPGASVKL SCKASGYTFT EYIIHWVKQR SGQGLEWIGW 60         70         80         90         100
8H8F5 VH4 (ISSGSTTIYH ADTVKGRFTI SRDNPKNTLF LQMTSLRSED TAMYYCARSG

3E12A2 VH1 FYPGSGSIKY NEKFKDKATL TADKSSSTVY MELSGLTSED SAVYFCARHD
```

```
3E12G9 VH9  FYPGSGSIKY  NEKFKDKATL  TADKSSSTVY  MELSGLTSED  SAVYFCARHD 110
                                                              (SEQ ID NO: 66)
8H8F5 VH4   (QFGNYFDYWG  QGTTLTVSS (SEQ ID NO: 67)
3E12A2 VH1  GYS-YFDYWG  QGTTLTV--

(SEQ ID NO: 68)
3E12G9 VH9  GYS-YFDYWG  QGTTLTV--
```

The comparison of the variable light chain alignment for mAb 8H8F5, 3E12A2, and 3E12G9 is shown below (SEQ ID NO: 69, 70, and 71, respectively):

```
            10          20          30 40       50

8H8F5 VL6   (MTQSPKFLLV  SAGDRVTLTC  KASQSVNND-  -----VYWYQ  QEPGQSPKLL

3E12A2 VL6  --QSPSSLAV   SAGEKVTMSC  KSSQSLLNSR  TRKNYLAWYQ  QKPGQSPKLL

3E12G9 VL2  --QSPSSLAV   SAGEKVTMSC  KSSQSLLNSR  TRKNYLAWYQ  QKPGQSPKLL 60          70       80          90          100

8H8F5 VL6   (IYYASNRYTG  VPDRFTGSGY  GTDFTFTIST  VQSEDLAVYF  CQHDYSSPYT

3E12A2 VL6  IYWASTRESG   VPDRFTGSGS  GTDFTLTISS  VQAEDLAVYY  CKQSYN-LYT

3E12G9 VL2  IYWASTRESG   VPDRFTGSGS  GTDFTLTISS  VQAEDLAVYY  CKQSYN-LYT 110
                                                              (SEQ ID NO: 69)
8H8F5 VL6   (FGGGTKLEIK  R (SEQ ID NO: 70)
3E12A2 VL6  FGGGTKLEIK  -

(SEQ ID NO: 71)
3E12G9 VL2  FGGGTKLEIK  -
```

DVLR1/CLEC5A interacts with the dengue virion directly and, thereby, leads to DAP12 phosphorylation. Blockade of DVLR1/CLEC5A-DV interaction suppresses the secretion of proinflammatory cytokines without affecting interferon-α release. Moreover, anti-DVLR1/CLEC5A monoclonal antibodies inhibit DV-induced plasma leakage, as well as subcutaneous and vital organ hemorrhaging, and reduce the incidence of DV infection by ~50% in STAT1-deficient mice. The results suggest that DV-triggered cytokine release from macrophages involves both DVLR1/CLEC5A and TLR7 pathways, while the blockade of DVLR1/CLEC5A-DV interactions attenuates inflammation without preventing the clearance of virus. However, the blockade of TLR7 (or MyD88) receptors inhibits secretion of both pro-inflammation cytokines, as well as viral clearance cytokines, which ultimately prevents the viral clearance as well as inflammation. Thus, effective treatment of dengue virus, as well as other flaviviruses such as Japanese encephamyelitis virus, requires attenuation of viral binding to DVLR1/CLEC5A, but not TLR7 or MyD88 receptors. Consequently, blocking of binding by dengue virus with anti-DVLR1/CLEC5A antibodies provides a therapy for severe dengue disease progression in DHF/DSS patients.

The foregoing written specification is considered to be sufficient to enable one skilled in the art to practice the invention. The present invention is not to be limited in scope by the hybridomas deposited, since the deposited embodiments are intended to illustrate only certain aspects of the invention and any antibodies that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that they represent. Indeed, various modifications of the invention in addition to those shown and described herein will become apparent to those skilled in the art from the foregoing description and fall within the scope of the appended claims.

The invention claimed is:

1. A method for reducing cytokine release from macrophages mediated by Japanese Encephalitis Virus (JEV) infection, comprising administering to a subject in need thereof an effective amount of a pharmaceutical composition including an anti-human DVLR1/CLEC5A receptor antibody and a pharmaceutically acceptable carrier, wherein the anti-human DVLR1/CLEC5A antibody includes (i) the heavy chain variable sequence (VH) of SEQ ID NO:66 and the light chain variable sequence (VL) of SEQ ID NO:69; (ii) the VH sequence of SEQ ID NO:67 and the VL sequence of SEQ ID NO:70; or (iii) the VH sequence of SEQ ID NO:68 and the VL sequence of SEQ ID NO:71.

2. The method of claim 1, wherein the anti-human DVLR1/CLEC5A antibody is a humanized antibody.

3. The method of claim 1, wherein the anti-human DVLR1/CLEC5A antibody comprises the heavy chain variable sequence (VH) of SEQ ID NO:66 and the light chain variable sequence (VL) of SEQ ID NO:69.

4. The method of claim 1, wherein the anti-human DVLR1/CLEC5A antibody comprises the VH sequence of SEQ ID NO:67 and the VL sequence of SEQ ID NO:70.

5. The method of claim 1, wherein the anti-human DVLR1/CLEC5A antibody comprises the VH sequence of SEQ ID NO:68 and the VL sequence of SEQ ID NO:71.

* * * * *

SEQUENCE LISTING

```
<160> NUMBER OF SEQ ID NOS: 73

<210> SEQ ID NO 1
<211> LENGTH: 27
```

```
<212> TYPE: DNA
<213> ORGANISM: Human

<400> SEQUENCE: 1
gaatcctttc agtactacca gctctcc                                    27

<210> SEQ ID NO 2
<211> LENGTH: 27
<212> TYPE: DNA
<213> ORGANISM: Human

<400> SEQUENCE: 2
gaattctcag tcaccttcgc ctaatgt                                    27

<210> SEQ ID NO 3
<211> LENGTH: 24
<212> TYPE: DNA
<213> ORGANISM: Human

<400> SEQUENCE: 3
ggatccctgg ggatttggtc tgtc                                       24

<210> SEQ ID NO 4
<211> LENGTH: 24
<212> TYPE: DNA
<213> ORGANISM: Human

<400> SEQUENCE: 4
gaattcttaa ggtagttggt ccac                                       24

<210> SEQ ID NO 5
<211> LENGTH: 24
<212> TYPE: DNA
<213> ORGANISM: Human

<400> SEQUENCE: 5
ggatcctctc agagtttatg cccc                                       24

<210> SEQ ID NO 6
<211> LENGTH: 24
<212> TYPE: DNA
<213> ORGANISM: Human

<400> SEQUENCE: 6 ggatccccccc attatcttag acat                                      24

<210> SEQ ID NO 7
<211> LENGTH: 30
<212> TYPE: DNA
<213> ORGANISM: Human

<400> SEQUENCE: 7
ggatcctttc aaaaatattc tcagcttctt                                 30

<210> SEQ ID NO 8
<211> LENGTH: 28
<212> TYPE: DNA
<213> ORGANISM: Human

<400> SEQUENCE: 8
gaattctcat aagtggatct tcatcatc                                   28

<210> SEQ ID NO 9
<211> LENGTH: 30
```

```
<212> TYPE: DNA
<213> ORGANISM: Human

<400> SEQUENCE: 9
ggatccttta tgtatagcaa aactgtcaag                                      30

<210> SEQ ID NO 10
<211> LENGTH: 30
<212> TYPE: DNA
<213> ORGANISM: Human

<400> SEQUENCE: 10
gaattcttat atgtagatct tcttcatctt                                      30

<210> SEQ ID NO 11
<211> LENGTH: 27
<212> TYPE: DNA
<213> ORGANISM: Human

<400> SEQUENCE: 11
ggatcccatc acaacttttc acgctgt                                         27

<210> SEQ ID NO 12
<211> LENGTH: 27
<212> TYPE: DNA
<213> ORGANISM: Human

<400> SEQUENCE: 12
gaattcctag ttcaatgttg ttccagg                                         27

<210> SEQ ID NO 13
<211> LENGTH: 29
<212> TYPE: DNA
<213> ORGANISM: Human

<400> SEQUENCE: 13
gaagatctac atttcgcatc tttcaaacc                                       29

<210> SEQ ID NO 14
<211> LENGTH: 27
<212> TYPE: DNA
<213> ORGANISM: Human

<400> SEQUENCE: 14
gaattcctag ttcaatgttg ttccagg                                         27

<210> SEQ ID NO 15
<211> LENGTH: 24
<212> TYPE: DNA
<213> ORGANISM: Human

<400> SEQUENCE: 15
ggatcccggt ttatgggcac cata                                            24

<210> SEQ ID NO 16
<211> LENGTH: 24
<212> TYPE: DNA
<213> ORGANISM: Human

<400> SEQUENCE: 16
ggatcctcac ggttctgatg ggac                                            24

<210> SEQ ID NO 17
<211> LENGTH: 26
```

```
<212> TYPE: DNA
<213> ORGANISM: Human

<400> SEQUENCE: 17
ggatccaagg tccccagctc cataag                                          26

<210> SEQ ID NO 18
<211> LENGTH: 23
<212> TYPE: DNA
<213> ORGANISM: Human

<400> SEQUENCE: 18
gaattcctac gcaggagggg ggt                                             23

<210> SEQ ID NO 19
<211> LENGTH: 25
<212> TYPE: DNA
<213> ORGANISM: Human

<400> SEQUENCE: 19
ggatccaagg tccccagctc cctaa                                           25

<210> SEQ ID NO 20
<211> LENGTH: 26
<212> TYPE: DNA
<213> ORGANISM: Human

<400> SEQUENCE: 20
gaattcctat tcgtctctga agcagg                                          26

<210> SEQ ID NO 21
<211> LENGTH: 26
<212> TYPE: DNA
<213> ORGANISM: Human

<400> SEQUENCE: 21
agatctagta acgatggttt caccac                                          26

<210> SEQ ID NO 22
<211> LENGTH: 27
<212> TYPE: DNA
<213> ORGANISM: Human

<400> SEQUENCE: 22
gaattcctgt gatcatttgg cattctt                                         27

<210> SEQ ID NO 23
<211> LENGTH: 24
<212> TYPE: DNA
<213> ORGANISM: Human

<400> SEQUENCE: 23
ggatccacat atggtgaaac tggc                                            24

<210> SEQ ID NO 24
<211> LENGTH: 24
<212> TYPE: DNA
<213> ORGANISM: Human

<400> SEQUENCE: 24
ggatccagct tctactcata ggta                                            24

<210> SEQ ID NO 25
<211> LENGTH: 27
```

<212> TYPE: DNA
<213> ORGANISM: Human

<400> SEQUENCE: 25
ggatccacca tggctatttg gagatcc                                          27

<210> SEQ ID NO 26
<211> LENGTH: 29
<212> TYPE: DNA
<213> ORGANISM: Human

<400> SEQUENCE: 26
gaattcttac attgaaaact tcttctcac                                        29

<210> SEQ ID NO 27
<211> LENGTH: 27
<212> TYPE: DNA
<213> ORGANISM: Human

<400> SEQUENCE: 27
ggatcctcca aatttcagag ggacctg                                          27

<210> SEQ ID NO 28
<211> LENGTH: 25
<212> TYPE: DNA
<213> ORGANISM: Human

<400> SEQUENCE: 28
gaattctcag tgactctcct ggctg                                            25

<210> SEQ ID NO 29
<211> LENGTH: 30
<212> TYPE: DNA
<213> ORGANISM: Human

<400> SEQUENCE: 29
ggatccgtaa ctttgaagat agaaatgaaa                                       30

<210> SEQ ID NO 30
<211> LENGTH: 28
<212> TYPE: DNA
<213> ORGANISM: Human

<400> SEQUENCE: 30
gaattctcat gcctccctaa aatatgta                                         28

<210> SEQ ID NO 31
<211> LENGTH: 23
<212> TYPE: DNA
<213> ORGANISM: Human

<400> SEQUENCE: 31
ggatcctcat gctccgggcc gcg                                              23

<210> SEQ ID NO 32
<211> LENGTH: 27
<212> TYPE: DNA
<213> ORGANISM: Human

<400> SEQUENCE: 32
gaattcgcta gcaatcacca atgctga                                          27

<210> SEQ ID NO 33
<211> LENGTH: 20

```
<212> TYPE: DNA
<213> ORGANISM: Human

<400> SEQUENCE: 33
agaggtgaca gaggatccca                                              20

<210> SEQ ID NO 34
<211> LENGTH: 24
<212> TYPE: DNA
<213> ORGANISM: Human

<400> SEQUENCE: 34
gaattcgtga tcccatcaca gtcc                                         24

<210> SEQ ID NO 35
<211> LENGTH: 22
<212> TYPE: DNA
<213> ORGANISM: Human

<400> SEQUENCE: 35
ggatcctgcc agggctccaa ct                                           22

<210> SEQ ID NO 36
<211> LENGTH: 19
<212> TYPE: DNA
<213> ORGANISM: Human

<400> SEQUENCE: 36
atgacagatc tgagggtca                                               19

<210> SEQ ID NO 37
<211> LENGTH: 19
<212> TYPE: DNA
<213> ORGANISM: Human

<400> SEQUENCE: 37
cagccttgga gacctgagt                                               19

<210> SEQ ID NO 38
<211> LENGTH: 17
<212> TYPE: DNA
<213> ORGANISM: Human

<400> SEQUENCE: 38
tagcctactc tggccgc                                                 17

<210> SEQ ID NO 39
<211> LENGTH: 18
<212> TYPE: DNA
<213> ORGANISM: Human

<400> SEQUENCE: 39
ttgttggaat gaccttat                                                18

<210> SEQ ID NO 40
<211> LENGTH: 27
<212> TYPE: DNA
<213> ORGANISM: Human

<400> SEQUENCE: 40
gaatcctttc agtactacca gctctcc                                      27

<210> SEQ ID NO 41
<211> LENGTH: 27
```

```
<212> TYPE: DNA
<213> ORGANISM: Human

<400> SEQUENCE: 41
gaatcccatc acaactttc acgctgt                                          27

<210> SEQ ID NO 42
<211> LENGTH: 25
<212> TYPE: DNA
<213> ORGANISM: Human

<400> SEQUENCE: 42
gcggaaagag attttcctt gttca                                            25

<210> SEQ ID NO 43
<211> LENGTH: 23
<212> TYPE: DNA
<213> ORGANISM: Human

<400> SEQUENCE: 43
agatctacag cagacaagac ctg                                             23

<210> SEQ ID NO 44
<211> LENGTH: 24
<212> TYPE: DNA
<213> ORGANISM: Human

<400> SEQUENCE: 44
agatctagcg ccaggagccc tctg                                            24

<210> SEQ ID NO 45
<211> LENGTH: 23
<212> TYPE: DNA
<213> ORGANISM: Human

<400> SEQUENCE: 45
ggatccccaa ggtccccagc tcc                                             23

<210> SEQ ID NO 46
<211> LENGTH: 30
<212> TYPE: DNA
<213> ORGANISM: Human

<400> SEQUENCE: 46
gaattcttac attgaaaact tcttctcaca                                      30

<210> SEQ ID NO 47
<211> LENGTH: 28
<212> TYPE: DNA
<213> ORGANISM: Human

<400> SEQUENCE: 47
gaatcctcat gcctccctaa aatatgta                                        28

<210> SEQ ID NO 48
<211> LENGTH: 20
<212> TYPE: DNA
<213> ORGANISM: Human

<400> SEQUENCE: 48
gcccagtgca cctactatag                                                 20

<210> SEQ ID NO 49
<211> LENGTH: 23
```

<212> TYPE: DNA
<213> ORGANISM: Human

<400> SEQUENCE: 49
gtgcactggg cctgtctggg tcc                                    23

<210> SEQ ID NO 50
<211> LENGTH: 20
<212> TYPE: DNA
<213> ORGANISM: Human

<400> SEQUENCE: 50
ggagtgctgt attcctaaac                                        20

<210> SEQ ID NO 51
<211> LENGTH: 25
<212> TYPE: DNA
<213> ORGANISM: Human

<400> SEQUENCE: 51
gaattcctgg cttttattga gatgg                                  25

<210> SEQ ID NO 52
<211> LENGTH: 21
<212> TYPE: DNA
<213> ORGANISM: Human

<400> SEQUENCE: 52
gaaggatgag gaagaccagg c                                      21

<210> SEQ ID NO 53
<211> LENGTH: 21
<212> TYPE: DNA
<213> ORGANISM: Human

<400> SEQUENCE: 53
catcggcagt tgacttgggt g                                      21

<210> SEQ ID NO 54
<211> LENGTH: 20
<212> TYPE: DNA
<213> ORGANISM: Human

<400> SEQUENCE: 54
agggtggcat ggagcctctc                                        20

<210> SEQ ID NO 55
<211> LENGTH: 24
<212> TYPE: DNA
<213> ORGANISM: Human

<400> SEQUENCE: 55
gaattccaca tgggcatcct cgaa                                   24

<210> SEQ ID NO 56
<211> LENGTH: 20
<212> TYPE: DNA
<213> ORGANISM: Human

<400> SEQUENCE: 56
cagccatggg cctcaccctg                                        20

<210> SEQ ID NO 57
<211> LENGTH: 25

```
<212> TYPE: DNA
<213> ORGANISM: Human

<400> SEQUENCE: 57
gaattcctgg ctgggttcca aaggg                                           25

<210> SEQ ID NO 58
<211> LENGTH: 25
<212> TYPE: DNA
<213> ORGANISM: Human

<400> SEQUENCE: 58
gaattcctgg ctgggttcca aaggg                                           25

<210> SEQ ID NO 59
<211> LENGTH: 25
<212> TYPE: DNA
<213> ORGANISM: Human

<400> SEQUENCE: 59
gaattcctgg tgcctgatgg agggc                                           25

<210> SEQ ID NO 60
<211> LENGTH: 672
<212> TYPE: DNA
<213> ORGANISM: Human

<400> SEQUENCE: 60
caggtgcagc tcgaggagtc aggacctgag ctggtgaaac ccggggcatc agtgaagctg      60
tcctgcaagg cttctggcta caccttcact gagtatatta cactgggt aaagcagagg     120 tctggacagg gtcttgagtg gattgggtgg ttttaccctg aagtggtag tataaagtac     180 aatgagaaat tcaaggacaa ggccacattg actgcggaca atcctccag cacagtctat     240 atggagctta gtggattgac atctgaagac tctgcggtct atttctgtgc aagacacgat     300
ggttactcct actttgacta ctggggccaa ggcaccactc tcacagtctc ctcagccaaa     360
acgacacccc catctgtcta tccactggcc cctggatctg ctgcccaaac taactccatg     420
gtgaccctgg gatgcctggt caagggctat ttccctgagc cagtgacagt gacctggaac     480
tctggatccc tgtccagcgg tgtgcacacc ttcccagctg tcctgcagtc tgacctctac     540
actctgagca gctcagtgac tgtcccctcc agcacctggc ccagcgagac cgtcacctgc     600
aacgttgccc acccggccag cagcaccaag gtggacaaga aaattgtgcc cagggattgt     660
actagtaagc ct                                                        672

<210> SEQ ID NO 61
<211> LENGTH: 678
<212> TYPE: DNA
<213> ORGANISM: Human

<400> SEQUENCE: 61
ccagttccga gctcgtgaca cagtctccat cctccctggc tgtgtcagca ggagagaagg      60
tcactatgag ctgcaaatcc agtcagagtc tgctcaacag tagaacccga agaactact     120 tggcttggta ccagcagaaa ccagggcagt ctcctaaact gctgatctac tgggcatcca     180
ctagggaatc tgggtccct gatcgcttca caggcagtgg atctgggaca gatttcactc     240
tcaccatcag cagtgtgcag gctgaagacc tggcagttta ttactgcaag caatcttata     300
atctgtacac gttcggaggg gggaccaagc tggaaataaa acgggctgat gctgcaccaa     360
ctgtatccat cttcccacca tccagtgagc agttaacatc tggaggtgcc tcagtcgtgt     420
```

```
gcttcttgaa caacttctac cccaaagaca tcaatgtcaa gtggaagatt gatggcagtg        480
aacgacaaaa tggcgtcctg aacagttgga ctgatcagga cagcaaagac agcacctaca        540
gcatgagcag caccctcacg ttgaccaagg acgagtatga acgacataac agctatacct        600
gtgaggccac tcacaagaca tcaacttcac ccattgtcaa gagcttcaac aggaatgagt        660
gttaattcta gacggcgc                                                     678

<210> SEQ ID NO 62
<211> LENGTH: 672
<212> TYPE: DNA
<213> ORGANISM: Human

<400> SEQUENCE: 62
caggtgcagc tcgagcagtc aggacctgag ctggtgaaac ccggggcatc agtgaagctg         60
tcctgcaagg cttctggcta caccttcact gagtatatta tacactgggt aaagcagagg        120
tctggacagg gtcttgagtg gattgggtgg ttttaccctg aagtggtag tataaagtac         180 aatgagaaat tcaaggacaa ggccacattg actgcggaca atcctccag cacagtctat         240 atggagctta gtgattgac atctgaagac tctgcggtct atttctgtgc aagacacgat         300
ggttactcct actttgacta ctggggccaa ggcaccactc tcacagtctc ctcagccaaa        360
acgacacccc catctgtcta tccactggcc cctggatctg ctgcccaaac taactccatg        420
gtgaccctgg gatgcctggt caagggctat tccctgagc cagtgacagt gacctggaac        480
tctggatccc tgtccagcgg tgtgcacacc ttcccagctg tcctgcagtc tgacctctac        540
actctgagca gctcagtgac tgtcccctcc agcacctggc ccagcgagac cgtcacctgc        600
aacgttgccc accggccag cagcaccaag gtggacaaga aaattgtgcc cagggattgt        660
actagtaagc ct                                                           672

<210> SEQ ID NO 63
<211> LENGTH: 678
<212> TYPE: DNA
<213> ORGANISM: Human

<400> SEQUENCE: 63
ccagttccga gctcgtgaca cagtctccat cctccctggc tgtgtcagca ggagagaagg         60
tcactatgag ctgcaaatcc agtcagagtc tgctcaacag tagaacccga agaactact        120 tggcttggta ccagcagaaa ccagggcagt ctcctaaact gctgatctac tgggcatcca        180
ctagggaatc tggggtccct gatcgcttca caggcagtgg atctgggaca gatttcactc        240
tcaccatcag cagtgtgcag gctgaagacc tggcagttta ttactgcaag caatcttata        300
atctgtacac gttcggaggg gggaccaagc tggaaataaa acgggctgat gctgcaccaa        360
ctgtatccat cttcccacca tccagtgagc agttaacatc tggaggtgcc tcagtcgtgt        420
gcttcttgaa caacttctac cccaaagaca tcaatgtcaa gtggaagatt gatggcagtg        480
aacgacaaaa tggcgtcctg aacagttgga ctgatcagga cagcaaagac agcacctaca        540
gcatgagcag caccctcacg ttgaccaagg acgagtatga acgacataac agctatacct        600
gtgaggccac tcacaagaca tcaacttcac ccattgtcaa gagcttcaac aggaatgagt        660
gttaattcta gacggcgc                                                     678

<210> SEQ ID NO 64
<211> LENGTH: 674
<212> TYPE: DNA
<213> ORGANISM: Human
```

<400> SEQUENCE: 64

```
gaggtgaagc tcgaggagtc tggacgaggc ttagtgcagc tggagggtc ccggaaactc         60
tcctgtgcag cctctggatt cactttcagt acctctggaa tgcactgggt tcgtcaggct        120
ccagagaagg ggctggagtg ggtcgcatac attagtagtg gcagcactac catctaccat       180
gcagacacag tgaagggccg attcaccatc tccagagaca atcccaagaa caccctgttc       240
ctgcaaatga ccagtctaag gtctgaggac acggccatgt attactgtgc aagatcgggt       300
cagtttggta actactttga ctactggggc caaggcacca ctctcacagt ctcctcagcc       360
aaaacgacac ccccatctgt ctatccactg cccctggatc tgctgcccaa actaactcca       420
tggtgaccct gggatgcctg gtcaagggct atttccctga ccagtgaca gtgacctgga       480
actctggatc cctgtccagc ggtgtgcaca ccttcccagc tgtcctgcag tctgacctct       540
acactctgag cagctcagtg actgtcccct ccagcacctg cccagcgag accgtcacct       600
gcaacgttgc ccaccggcc agcagcacca aggtggacaa gaaaattgtg cccagggatt       660
gtactagtaa gcct                                                          674
```

<210> SEQ ID NO 65
<211> LENGTH: 666
<212> TYPE: DNA
<213> ORGANISM: Human

<400> SEQUENCE: 65

```
ccagatgtga gctcgtcatg acccagtctc caaaattcct gcttgtatca gcaggagaca         60
gggttaccct aacctgcaag gccagtcaga gtgtgaataa tgatgtatat tggtaccaac        120
aggagccagg tcagtctcct aaactgctga tatactatgc atccaatcgc tacactggag       180
tccctgatcg cttcactggc agtggatatg ggacggattt cactttcacc atcagcactg       240
tgcagtctga agacctggca gtttatttct gtcagcacga ttatagctct ccgtacacgt       300
tcggagggg gaccaagctg gaaataaaac gggctgatgc tgcaccaact gtatccatct       360
tcccaccatc cagtgagcag ttaacatctg gaggtgcctc agtcgtgtgc ttcttgaaca       420
acttctaccc caaagacatc aatgtcaagt ggaagattga tggcagtgaa cgacaaaatg       480
gcgtcctgaa cagttggact gatcaggaca gcaaagacag cacctacagc atgagcagca       540
ccctcacgtt gaccaaggac gagtatgaac acataacag ctatacctgt gaggccactc       600
acaagacatc aacttcaccc attgtcaaga gcttcaacag gaatgagtgt taattctaga       660
cggcgc                                                                  666
```

<210> SEQ ID NO 66
<211> LENGTH: 115
<212> TYPE: PRT
<213> ORGANISM: Human

<400> SEQUENCE: 66

```
Glu Ser Gly Arg Gly Leu Val Gln Pro Gly Gly Ser Arg Lys Leu Ser
  1               5                  10                  15

Cys Ala Ala Ser Gly Phe Thr Phe Ser Thr Ser Gly Met His Trp Val
             20                  25                  30

Arg Gln Ala Pro Glu Lys Gly Leu Glu Trp Val Ala Tyr Ile Ser Ser
         35                  40                  45

Gly Ser Thr Thr Ile Tyr His Ala Asp Thr Val Lys Gly Arg Phe Thr
     50                  55                  60
```

```
Ile Ser Arg Asp Asn Pro Lys Asn Thr Leu Phe Leu Gln Met Thr Ser
 65                  70                  75                  80

Leu Arg Ser Glu Asp Thr Ala Met Tyr Tyr Cys Cys Ala Arg Ser Gly
             85                  90                  95

Gln Phe Gly Asn Tyr Phe Asp Tyr Trp Gly Gln Gly Thr Thr Leu Thr
            100                 105                 110

Val Ser Ser
        115

<210> SEQ ID NO 67
<211> LENGTH: 116
<212> TYPE: PRT
<213> ORGANISM: Human

<400> SEQUENCE: 67

Gln Val Gln Leu Glu Glu Ser Gly Pro Glu Leu Val Lys Pro Gly Ala
  1               5                  10                  15

Ser Val Lys Leu Ser Cys Lys Ala Ser Gly Tyr Thr Phe Thr Glu Tyr
             20                  25                  30

Ile Ile His Trp Val Lys Gln Arg Ser Gly Gln Gly Leu Glu Trp Ile
         35                  40                  45

Gly Trp Phe Tyr Pro Gly Ser Gly Ser Ile Lys Tyr Asn Glu Lys Phe
     50                  55                  60

Lys Asp Lys Ala Thr Leu Thr Ala Asp Lys Ser Ser Ser Thr Val Tyr
 65                  70                  75                  80

Met Glu Leu Ser Gly Leu Thr Ser Glu Asp Ser Ala Val Tyr Phe Cys
             85                  90                  95

Ala Arg His Asp Gly Tyr Ser Tyr Phe Asp Tyr Trp Gly Gln Gly Thr
            100                 105                 110

Thr Leu Thr Val
        115

<210> SEQ ID NO 68
<211> LENGTH: 117
<212> TYPE: PRT
<213> ORGANISM: Human

<400> SEQUENCE: 68

Gln Val Gln Leu Glu Gln Ser Gly Pro Glu Leu Val Lys Pro Gly Ala
  1               5                  10                  15

Ser Val Lys Leu Ser Cys Lys Ala Ser Gly Tyr Thr Phe Thr Glu Tyr
             20                  25                  30

Ile Ile His Trp Val Lys Gln Arg Ser Gly Gln Gly Leu Glu Trp Ile
         35                  40                  45

Gly Trp Phe Tyr Pro Gly Ser Gly Ser Ile Lys Tyr Asn Glu Lys Phe
     50                  55                  60

Lys Asp Lys Ala Thr Leu Thr Ala Asp Lys Ser Ser Ser Thr Val Tyr
 65                  70                  75                  80

Met Glu Leu Ser Gly Leu Thr Ser Glu Asp Ser Ala Val Tyr Phe Cys
             85                  90                  95

Ala Arg His Asp Gly Tyr Ser Tyr Phe Asp Tyr Trp Gly Gln Gly Gly
            100                 105                 110

Thr Thr Leu Thr Val
        115

<210> SEQ ID NO 69
<211> LENGTH: 104
<212> TYPE: PRT
```

<213> ORGANISM: Human

<400> SEQUENCE: 69

Met Thr Gln Ser Pro Lys Phe Leu Leu Val Ser Ala Gly Asp Arg Val
1               5                   10                  15

Thr Leu Thr Cys Lys Ala Ser Gln Ser Val Asn Asn Asp Val Tyr Trp
            20                  25                  30

Tyr Gln Gln Glu Pro Gly Gln Ser Pro Lys Leu Leu Ile Tyr Trp Ala
        35                  40                  45

Ser Thr Arg Glu Ser Gly Val Pro Asp Arg Phe Thr Gly Ser Gly Ser
    50                  55                  60

Gly Thr Asp Phe Thr Leu Thr Ile Ser Ser Val Gln Ala Glu Asp Leu
65                  70                  75                  80

Ala Val Tyr Tyr Cys Lys Gln Ser Tyr Asn Leu Tyr Thr Phe Gly Gly
                85                  90                  95

Gly Thr Lys Leu Glu Ile Lys Arg
            100

<210> SEQ ID NO 70
<211> LENGTH: 106
<212> TYPE: PRT
<213> ORGANISM: Human

<400> SEQUENCE: 70

Gln Ser Pro Ser Ser Leu Ala Val Ser Ala Gly Glu Lys Val Thr Met
1               5                   10                  15

Ser Cys Lys Ser Ser Gln Ser Leu Leu Asn Ser Arg Thr Arg Lys Asn
            20                  25                  30

Tyr Leu Ala Trp Tyr Gln Gln Lys Pro Gly Gln Ser Pro Lys Leu Leu
        35                  40                  45

Ile Tyr Trp Ala Ser Thr Arg Glu Ser Gly Val Pro Asp Arg Phe Thr
    50                  55                  60

Gly Ser Gly Ser Gly Thr Asp Phe Thr Leu Thr Ile Ser Ser Val Gln
65                  70                  75                  80

Ala Glu Asp Leu Ala Val Tyr Tyr Cys Lys Gln Ser Asn Leu Tyr Thr
                85                  90                  95

Phe Gly Gly Gly Thr Lys Leu Glu Ile Lys
            100                 105

<210> SEQ ID NO 71
<211> LENGTH: 107
<212> TYPE: PRT
<213> ORGANISM: Human

<400> SEQUENCE: 71

Gln Ser Pro Ser Ser Leu Ala Val Ser Ala Gly Glu Lys Val Thr Met
1               5                   10                  15

Ser Cys Lys Ser Ser Gln Ser Leu Leu Asn Ser Arg Thr Arg Lys Asn
            20                  25                  30

Tyr Leu Ala Trp Tyr Gln Gln Lys Pro Gly Gln Ser Pro Lys Leu Leu
        35                  40                  45

Ile Tyr Trp Ala Ser Thr Arg Glu Ser Gly Val Pro Asp Arg Phe Thr
    50                  55                  60

Gly Ser Gly Ser Gly Thr Asp Phe Thr Leu Thr Ile Ser Ser Val Gln
65                  70                  75                  80

Ala Glu Asp Leu Ala Val Tyr Tyr Cys Lys Gln Ser Tyr Asn Leu Tyr
                85                  90                  95

```
Thr Phe Gly Gly Gly Thr Lys Leu Glu Ile Lys
                100                 105
```

<210> SEQ ID NO 72
<211> LENGTH: 187
<212> TYPE: PRT
<213> ORGANISM: Human

<400> SEQUENCE: 72

```
Met Asn Trp His Met Ile Ile Ser Gly Leu Ile Val Val Leu Lys
1               5                   10                  15

Val Val Gly Met Thr Leu Phe Leu Leu Tyr Phe Pro Gln Ile Phe Asn
            20                  25                  30

Lys Ser Asn Asp Gly Phe Thr Thr Arg Ser Tyr Gly Thr Val Ser
            35                  40                  45

Gln Ile Phe Gly Ser Ser Ser Pro Ser Pro Asn Gly Phe Ile Thr Thr
        50                  55                  60

Arg Ser Tyr Gly Thr Val Cys Pro Lys Asp Trp Glu Phe Tyr Gln Ala
65                  70                  75                  80

Arg Cys Phe Phe Leu Ser Thr Ser Glu Ser Ser Trp Asn Glu Ser Arg
                85                  90                  95

Asp Phe Cys Lys Gly Lys Gly Ser Thr Leu Ala Ile Val Asn Thr Pro
            100                 105                 110

Glu Lys Leu Phe Leu Gln Asp Ile Thr Asp Ala Glu Lys Tyr Phe Ile
            115                 120                 125

Gly Leu Ile Tyr His Arg Glu Glu Lys Arg Trp Arg Trp Ile Asn Asn
        130                 135                 140

Ser Val Phe Asn Gly Asn Val Thr Asn Gln Asn Gln Asn Phe Asn Cys
145                 150                 155                 160

Ala Thr Ile Gly Leu Thr Lys Thr Phe Asp Ala Ala Ser Cys Asp Ile
                165                 170                 175

Ser Tyr Arg Arg Ile Cys Glu Lys Asn Ala Lys
            180                 185
```

<210> SEQ ID NO 73
<211> LENGTH: 164
<212> TYPE: PRT
<213> ORGANISM: Human

<400> SEQUENCE: 73

```
Met Asn Trp His Met Ile Ile Ser Gly Leu Ile Val Val Leu Lys
1               5                   10                  15

Val Val Gly Met Thr Leu Phe Leu Leu Tyr Phe Pro Gln Ile Phe Asn
            20                  25                  30

Lys Ser Asn Asp Gly Phe Thr Thr Arg Ser Tyr Gly Thr Val Cys
            35                  40                  45

Pro Lys Asp Trp Glu Phe Tyr Gln Ala Arg Cys Phe Phe Leu Ser Thr
        50                  55                  60

Ser Glu Ser Ser Trp Asn Glu Ser Arg Asp Phe Cys Lys Gly Lys Gly
65                  70                  75                  80

Ser Thr Leu Ala Ile Val Asn Thr Pro Glu Lys Leu Phe Leu Gln Asp
                85                  90                  95

Ile Thr Asp Ala Glu Lys Tyr Phe Ile Gly Leu Ile Tyr His Arg Glu
            100                 105                 110

Glu Lys Arg Trp Arg Trp Ile Asn Asn Ser Val Phe Asn Gly Asn Val
            115                 120                 125
```

```
                                    -continued
Thr Asn Gln Asn Gln Asn Phe Asn Cys Ala Thr Ile Gly Leu Thr Lys
    130             135             140

Thr Phe Asp Ala Ala Ser Cys Asp Ile Ser Tyr Arg Arg Ile Cys Glu
145                 150             155                 160

Lys Asn Ala Lys
```